(12) United States Patent
Abrantes et al.

(10) Patent No.: US 12,351,602 B2
(45) Date of Patent: Jul. 8, 2025

(54) METHODS OF INACTIVATING VIRAL CONTAMINANTS

(71) Applicant: Ichnos Sciences SA, La Chaux-de-Fonds (CH)

(72) Inventors: Filipa Abrantes, La Chaux-de-Fonds (CH); Sonia Letestu, La Chaux-de-Fonds (CH); Laure Cahuzac, La Chaux-de-Fonds (CH); Lionel Duarte, La Chaux-de-Fonds (CH)

(73) Assignee: Ichnos Sciences SA., La Chaux-de-Fonds (CH)

( * ) Notice: Subject to any disclaimer, the term of this patent is extended or adjusted under 35 U.S.C. 154(b) by 1158 days.

(21) Appl. No.: 16/641,281

(22) PCT Filed: Aug. 27, 2018

(86) PCT No.: PCT/IB2018/056502
§ 371 (c)(1),
(2) Date: Aug. 5, 2020

(87) PCT Pub. No.: WO2019/038742
PCT Pub. Date: Feb. 28, 2019

(65) Prior Publication Data
US 2020/0369747 A1 Nov. 26, 2020

(30) Foreign Application Priority Data
Aug. 25, 2017 (EP) .................................. 17188012

(51) Int. Cl.
| | | |
|---|---|---|
| C07K 16/06 | (2006.01) |
| A61K 39/395 | (2006.01) |
| C07K 1/18 | (2006.01) |
| C07K 1/22 | (2006.01) |
| C07K 1/34 | (2006.01) |
| C07K 1/36 | (2006.01) |
| C07K 16/00 | (2006.01) |

(52) U.S. Cl.
CPC .............. *C07K 1/22* (2013.01); *A61K 39/395* (2013.01); *A61K 39/39591* (2013.01); *C07K 1/18* (2013.01); *C07K 1/34* (2013.01); *C07K 1/36* (2013.01); *C07K 16/00* (2013.01); *C07K 16/065* (2013.01); *C07K 2317/14* (2013.01); *C07K 2317/31* (2013.01)

(58) Field of Classification Search
CPC ..... C07K 16/00; C07K 16/065; A61K 39/395
See application file for complete search history.

(56) References Cited

U.S. PATENT DOCUMENTS

| | | | |
|---|---|---|---|
| 4,749,783 A | 6/1988 | Robert et al. | |
| 5,728,821 A * | 3/1998 | Yelton .................... | C07K 16/30 |
| | | | 435/328 |
| 2004/0137000 A1 * | 7/2004 | Lynn ....................... | A61P 31/18 |
| | | | 435/339.1 |
| 2015/0098897 A1 * | 4/2015 | Brahmbhatt ........... | A61K 39/44 |
| | | | 424/1.17 |
| 2017/0274299 A1 * | 9/2017 | Coutard ................... | C07K 1/36 |
| 2020/0369747 A1 | 11/2020 | Abrantes et al. | |

FOREIGN PATENT DOCUMENTS

| | | | | |
|---|---|---|---|---|
| CN | 106749660 A | | 5/2017 | |
| EP | 3446710 A1 | | 2/2019 | |
| WO | WO-9809660 A1 * | 3/1998 | ........... A61L 2/0088 |
| WO | WO 2010048192 A2 | | 4/2010 | |
| WO | WO-2011130119 A2 * | 10/2011 | ............... C12N 7/00 |
| WO | WO 2012082931 A1 | | 6/2012 | |
| WO | WO 2012131555 A2 | | 10/2012 | |
| WO | WO-2016034726 A1 * | 3/2016 | ......... B01D 15/3809 |
| WO | WO-2019038742 A1 | | 2/2019 | |

OTHER PUBLICATIONS

Burdick et al (Journal of Visualized Experiments, 2014, vol. 83, article e51023) (Year: 2014).*
BioRad Proteus A Handbook, "Protein A Antibody Purification Handbook—Mini & Midi spin columns," Issue 5, pp. 1-50, accessed at https://www.bio-rad-antibodies.com/static/2015/proteus/protein-a-handbook.pdf on May 18, 2020 (May 2016).
Streicher, H., and Sharon, N., "Recombinant plant lectins and their mutants," Methods in Enzymology 363—Recognition of Carbohydrates in Biological Systems, Part B: Specific Applications, Lee, Y.C., and Lee, R.T., eds., pp. 47-77, Academic Press, United States (2003).
Singh, A., et al., "Protein recovery from inclusion bodies of *Escherichia coli* using mild solubilization process," Microbial Cell Factories 14:41, BioMed Central, United Kingdom (2015).
Farshid M., "Assessment of Viral Clearance Studies," Presentica. com, accessed at http://www.presentica.com/ppt-presentation/assessment-of-viral-clearance-studies, accessed on Jun. 3, 2020, 20 pages.
Hsieh Y.T., et al. "Single-use technology for solvent/detergent virus inactivation of industrial plasma products." Transfusion 56(6):1384-1393. (2016).
International Search Report and Written Opinion for International Application No. PCT/IB2018/056502, European Patent Office, Netherlands, mailed on Nov. 6, 2018, 9 pages.
Liu HF et al., "Recovery and Purification Process Development for Monoclonal Antibody Production," MAbs.; 2(5):480-499, (2010).
Roberts P.L. et al., "Virus elimination during the purification of monoclonal antibodies by column chromatography and additional steps." Biotechnol Prog. 30(6):1341-1347. (2014).
Shukla AA et al., "Viral clearance for biopharmaceutical downstream processes," Pharm. Bioprocess. 3(2): 127-138, (2015).
World Health Organization, "Guidelines on viral inactivation and removal procedures intended to assure the viral safety of human blood plasma products," Presentica.com, accessed at http://www.presentica.com/ppt-presentation/assessment-of-viral-clearance-studies, accessed on Jun. 3, 2020, 75 pages.

* cited by examiner

*Primary Examiner* — Karen A. Canella
(74) *Attorney, Agent, or Firm* — Sterne, Kessler, Goldstein & Fox P.L.L.C.

(57) ABSTRACT

The present invention relates to a method for preparing an antibody-containing solution free viral contaminants starting from cultured cells are described. The method include a step of subjecting the antibody containing solution to a mix of solvent and detergent or to high pH.

Figure 1:
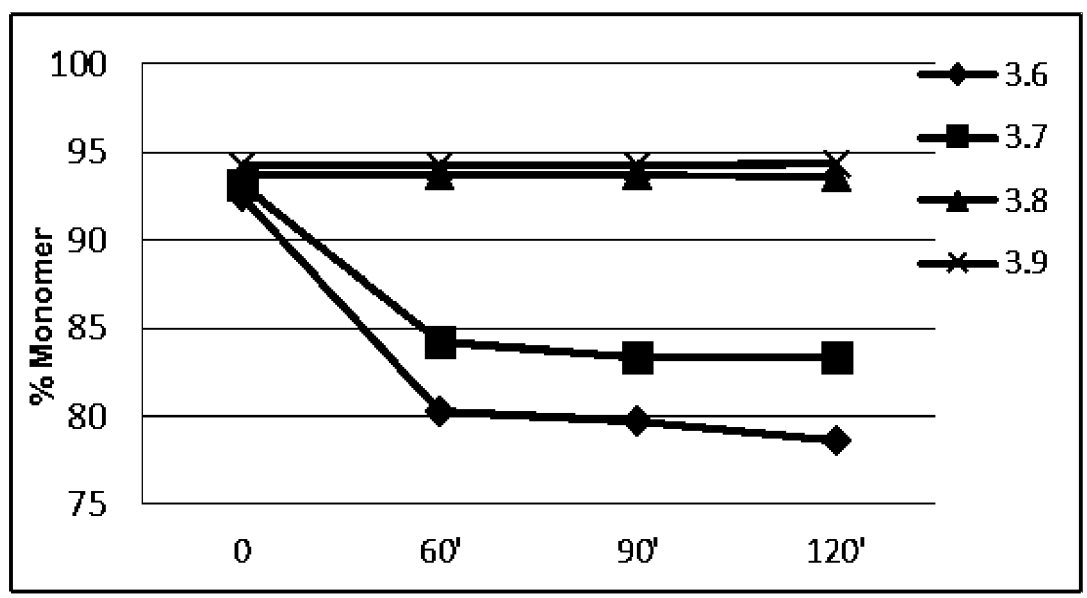

12 Claims, 24 Drawing Sheets
Specification includes a Sequence Listing.

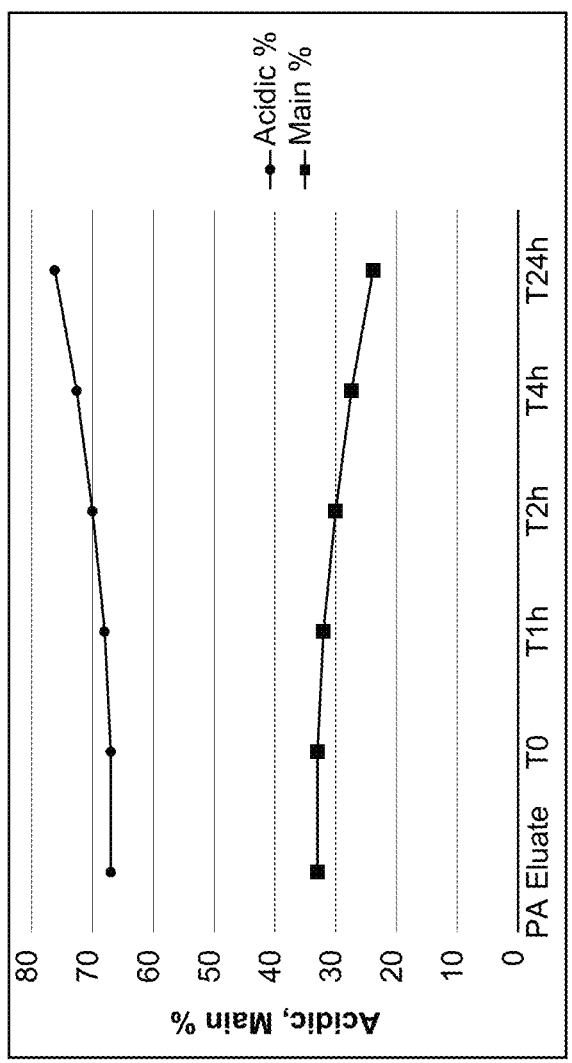
FIG. 13
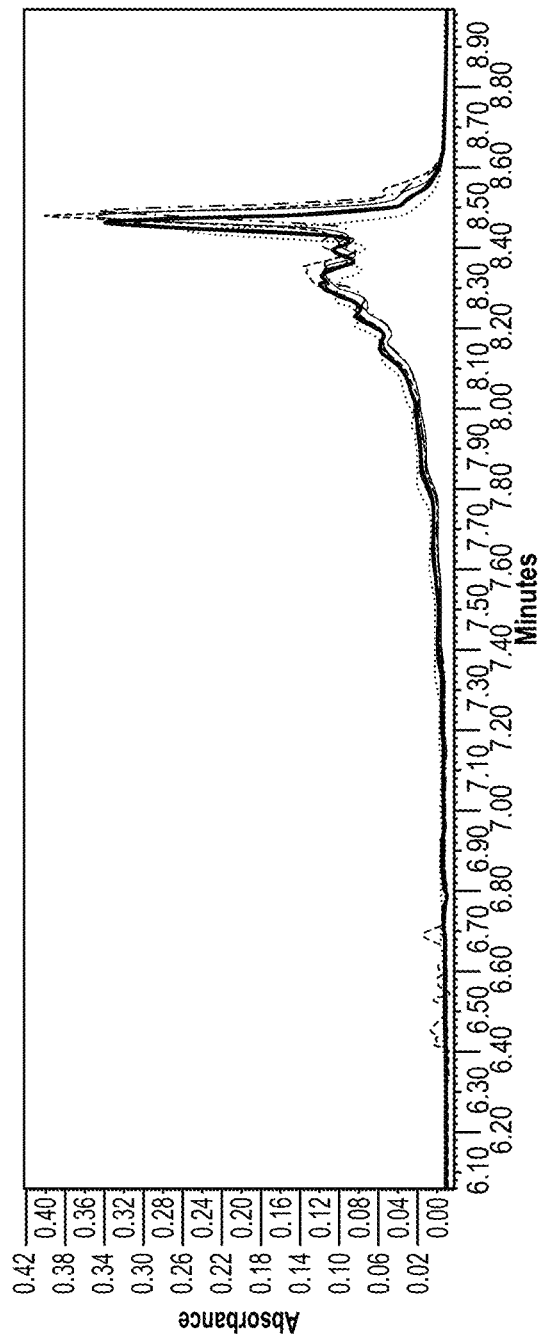

SEQUENCE LISTING

```
<160> NUMBER OF SEQ ID NOS: 8

<210> SEQ ID NO 1
<211> LENGTH: 234
<212> TYPE: PRT
<213> ORGANISM: Artificial Sequence
<220> FEATURE:
<223> OTHER INFORMATION: Light chain sequence (hum9G7_VL_cK)

<400> SEQUENCE: 1

Met Arg Ser Pro Ala Gln Leu Leu Phe Leu Leu Leu Trp Ile Pro
1               5                   10                  15

Gly Thr Asn Ala Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Val Ile Thr Ser Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Gln Gln His Tyr
            100                 105                 110

Thr Ile Pro Leu Thr Phe Gly Gln Gly Thr Lys Leu Glu Ile Lys Arg
        115                 120                 125
```

```
Thr Val Ala Pro Ser Val Phe Ile Phe Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230
```

<210> SEQ ID NO 2
<211> LENGTH: 470
<212> TYPE: PRT
<213> ORGANISM: Artificial Sequence
<220> FEATURE:
<223> OTHER INFORMATION: Heavy chain sequence (h9G7 1133 BTA LALA FTO
      (dA))

<400> SEQUENCE: 2

```
Met Arg Ser Pro Ala Gln Leu Leu Phe Leu Leu Leu Leu Trp Ile Pro
1               5                   10                  15

Gly Thr Asn Ala Gln Val Thr Leu Lys Glu Ser Gly Pro Thr Leu Val
                20                  25                  30

Lys Pro Thr Gln Thr Leu Thr Leu Thr Cys Thr Phe Ser Gly Leu Ser
            35                  40                  45

Leu Ser Thr Ser Gly Lys Gly Val Gly Trp Ile Arg Gln Pro Pro Gly
        50                  55                  60

Lys Ala Leu Glu Trp Leu Ala His Ile Trp Trp Asp Asp Lys Arg
65                  70                  75                  80

Tyr Asn Pro Ala Leu Lys Ser Arg Leu Thr Ile Thr Lys Asp Thr Ser
                85                  90                  95

Lys Asn Gln Val Val Leu Thr Met Thr Asn Met Asp Pro Val Asp Thr
            100                 105                 110

Ala Thr Tyr Tyr Cys Ala Arg Ile Glu Leu Gly Arg Ser Tyr Val Met
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240
```

```
Pro Lys Ser Cys Asp Lys Thr His Thr Cys Pro Pro Cys Pro Ala Pro
            245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Gln Phe Lys Trp Tyr Val Asp
            290                 295                 300

Gly Val Glu Val His Asn Ala Lys Thr Lys Pro Arg Glu Glu Gln Tyr
305                 310                 315                 320

Asn Ser Thr Phe Arg Val Val Ser Val Leu Thr Val Leu His Gln Asp
            325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Thr Lys Gly Gln Pro Arg
            355                 360                 365

Glu Pro Ala Val Tyr Thr Leu Pro Pro Ser Arg Glu Glu Met Thr Lys
            370                 375                 380

Asn Gln Val Lys Leu Val Cys Leu Val Thr Gly Phe Tyr Pro Ser Asp
385                 390                 395                 400

Ile Ala Val Glu Trp Glu Ser Ser Gly Gln Pro Glu Asn Asn Tyr Tyr
            405                 410                 415

Thr Thr Pro Pro Met Leu Asp Ser Asp Gly Ser Phe Ser Leu Val Ser
            420                 425                 430

Trp Leu Asn Val Asp Lys Ser Arg Trp Gln Gln Gly Asn Ile Phe Ser
            435                 440                 445

Cys Ser Val Met His Glu Ala Leu His Asn Arg Phe Thr Gln Lys Ser
            450                 455                 460

Leu Ser Leu Ser Pro Gly
465                 470

<210> SEQ ID NO 3
<211> LENGTH: 501
<212> TYPE: PRT
<213> ORGANISM: Artificial Sequence
<220> FEATURE:
<223> OTHER INFORMATION: scFv-Fc sequence: hSP34_H3K21_W100eY/T29E-W91F-
      L95T (hSP34v.3) scFv_11_BTB_D401Q_LALA

<400> SEQUENCE: 3

Met Arg Ser Pro Ala Gln Leu Leu Phe Leu Leu Leu Leu Trp Ile Pro
1               5                   10                  15

Gly Thr Asn Ala Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
            35                  40                  45

Phe Asn Thr Tyr Ala Met Asn Trp Val Arg Gln Ala Pro Gly Lys Gly
        50                  55                  60

Leu Glu Trp Val Ala Arg Ile Arg Ser Lys Tyr Asn Asn Tyr Ala Thr
65              70                  75                  80

Tyr Tyr Ala Asp Ser Val Lys Gly Arg Phe Thr Ile Ser Arg Asp Asp
            85                  90                  95

Ser Lys Asn Thr Leu Tyr Leu Gln Met Asn Ser Leu Arg Ala Glu Asp
            100                 105                 110
```

```
Thr Ala Val Tyr Tyr Cys Val Arg His Gly Asn Phe Gly Asn Ser Tyr
            115                 120                 125
Val Ser Tyr Phe Ala Tyr Trp Gly Gln Gly Thr Thr Val Thr Val Ser
        130                 135                 140
Ser Gly Gly Gly Ser Gly Gly Gly Ser Gly Gly Gly Gly Ser
145                 150                 155                 160
Glu Ile Val Val Thr Gln Ser Pro Ala Thr Leu Ser Val Ser Pro Gly
                165                 170                 175
Glu Arg Ala Thr Leu Ser Cys Arg Ser Ser Thr Gly Ala Val Thr Glu
            180                 185                 190
Ser Asn Tyr Ala Asn Trp Val Gln Glu Lys Pro Gly Gln Ala Phe Arg
        195                 200                 205
Gly Leu Ile Gly Gly Ala Asn Lys Arg Ala Pro Gly Val Pro Ala Arg
    210                 215                 220
Phe Ser Gly Ser Leu Ser Gly Asp Glu Ala Thr Leu Thr Ile Ser Ser
225                 230                 235                 240
Leu Gln Ser Glu Asp Phe Ala Val Tyr Tyr Cys Ala Leu Phe Tyr Ser
                245                 250                 255
Asn Thr Trp Val Phe Gly Gln Gly Thr Lys Leu Glu Ile Lys Gly Gly
            260                 265                 270
Gly Gly Thr Asp Lys Thr His Thr Cys Pro Pro Cys Pro Ala Pro Glu
        275                 280                 285
Ala Ala Gly Gly Pro Ser Val Phe Leu Phe Pro Pro Lys Pro Lys Asp
    290                 295                 300
Thr Leu Met Ile Ser Arg Thr Pro Glu Val Thr Cys Val Val Val Asp
305                 310                 315                 320
Val Ser His Glu Asp Pro Glu Val Lys Phe Asn Trp Tyr Val Asp Gly
                325                 330                 335
Val Glu Val His Asn Ala Lys Thr Lys Pro Arg Glu Glu Gln Tyr Asn
            340                 345                 350
Ser Thr Tyr Arg Val Val Ser Val Leu Thr Val Leu His Gln Asp Trp
        355                 360                 365
Leu Asn Gly Lys Glu Tyr Lys Cys Lys Val Ser Asn Lys Ala Leu Pro
    370                 375                 380
Ala Pro Ile Glu Lys Thr Ile Ser Lys Ala Lys Gly Gln Pro Arg Glu
385                 390                 395                 400
Pro Glu Val Ala Thr Phe Pro Pro Ser Arg Asp Glu Leu Thr Lys Asn
                405                 410                 415
Gln Val Thr Leu Val Cys Leu Val Thr Gly Phe Tyr Pro Ser Asp Ile
            420                 425                 430
Ala Val Glu Trp Glu Ser Asn Gly Gln Pro Glu Asn Asn Tyr Lys Thr
        435                 440                 445
Asp Pro Pro Leu Leu Glu Ser Gln Gly Ser Phe Ala Leu Ser Ser Arg
    450                 455                 460
Leu Arg Val Asp Lys Ser Arg Trp Gln Gln Gly Asn Val Phe Ser Cys
465                 470                 475                 480
Ser Val Met His Glu Ala Leu His Asn His Tyr Thr Gln Lys Ser Leu
                485                 490                 495
Ser Leu Ser Pro Gly
            500

<210> SEQ ID NO 4
<211> LENGTH: 723
```

<212> TYPE: PRT
<213> ORGANISM: Artificial Sequence
<220> FEATURE:
<223> OTHER INFORMATION: SF3_scFV_Hc sequence

<400> SEQUENCE: 4

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Asn Thr Tyr Ala Met Asn Trp Val Arg Gln Ala Pro Gly Lys Gly
    50                  55                  60

Leu Glu Trp Val Ala Arg Ile Arg Ser Lys Tyr Asn Asn Tyr Ala Thr
65                  70                  75                  80

Tyr Tyr Ala Asp Ser Val Lys Ser Arg Phe Thr Ile Ser Arg Asp Asp
                85                  90                  95

Ser Lys Asn Thr Leu Tyr Leu Gln Met Asn Ser Leu Arg Ala Glu Asp
            100                 105                 110

Thr Ala Val Tyr Tyr Cys Val Arg His Gly Asn Phe Gly Asn Ser Tyr
        115                 120                 125

Val Ser Tyr Phe Ala Tyr Trp Gly Gln Gly Thr Thr Val Thr Val Ser
    130                 135                 140

Ser Gly Gly Gly Gly Ser Gly Gly Gly Ser Gly Gly Gly Gly Ser
145                 150                 155                 160

Glu Ile Val Val Thr Gln Ser Pro Ala Thr Leu Ser Val Ser Pro Gly
                165                 170                 175

Glu Arg Ala Thr Leu Ser Cys Arg Ser Ser Thr Gly Ala Val Thr Glu
            180                 185                 190

Ser Asn Tyr Ala Asn Trp Val Gln Glu Lys Pro Gly Gln Ala Phe Arg
        195                 200                 205

Gly Leu Ile Gly Gly Ala Asn Lys Arg Ala Pro Gly Val Pro Ala Arg
    210                 215                 220

Phe Ser Gly Ser Leu Ser Gly Asp Glu Ala Thr Leu Thr Ile Ser Ser
225                 230                 235                 240

Leu Gln Ser Glu Asp Phe Ala Val Tyr Tyr Cys Ala Leu Phe Tyr Ser
                245                 250                 255

Asn Thr Trp Val Phe Gly Gln Gly Thr Lys Leu Glu Ile Lys Gly Gly
            260                 265                 270

Gly Gly Thr Gln Val Gln Leu Gln Glu Ser Gly Pro Gly Leu Val Lys
        275                 280                 285

Pro Ser Glu Thr Leu Ser Leu Thr Cys Thr Val Ser Gly Gly Ser Val
    290                 295                 300

Ser Ser Gly Asp Tyr Tyr Trp Thr Trp Ile Arg Gln Ser Pro Gly Lys
305                 310                 315                 320

Gly Leu Glu Trp Ile Gly His Ile Tyr Tyr Ser Gly Asn Thr Asn Tyr
                325                 330                 335

Asn Pro Ser Leu Lys Ser Arg Leu Thr Ile Ser Ile Asp Thr Ser Lys
            340                 345                 350

Thr Gln Phe Ser Leu Lys Leu Ser Ser Val Thr Ala Ala Asp Thr Ala
        355                 360                 365

Ile Tyr Tyr Cys Val Arg Asp Arg Val Thr Gly Ala Phe Asp Ile Trp
    370                 375                 380

-continued

```
Gly Gln Gly Thr Met Val Thr Val Ser Ser Ala Ser Thr Lys Gly Pro
385                 390                 395                 400

Ser Val Phe Pro Leu Ala Pro Ser Ser Lys Ser Thr Ser Gly Gly Thr
            405                 410                 415

Ala Ala Leu Gly Cys Leu Val Lys Asp Tyr Phe Pro Glu Pro Val Thr
        420                 425                 430

Val Ser Trp Asn Ser Gly Ala Leu Thr Ser Gly Val His Thr Phe Pro
    435                 440                 445

Ala Val Leu Gln Ser Ser Gly Leu Tyr Ser Leu Ser Ser Val Val Thr
450                 455                 460

Val Pro Ser Ser Leu Gly Thr Gln Thr Tyr Ile Cys Asn Val Asn
465                 470                 475                 480

His Lys Pro Ser Asn Thr Lys Val Asp Lys Lys Val Glu Pro Lys Ser
                485                 490                 495

Cys Asp Lys Thr His Thr Cys Pro Pro Cys Pro Ala Pro Glu Ala Ala
            500                 505                 510

Gly Gly Pro Ser Val Phe Leu Phe Pro Pro Lys Pro Lys Asp Thr Leu
        515                 520                 525

Met Ile Ser Arg Thr Pro Glu Val Thr Cys Val Val Val Asp Val Ser
    530                 535                 540

His Glu Asp Pro Glu Val Gln Phe Lys Trp Tyr Val Asp Gly Val Glu
545                 550                 555                 560

Val His Asn Ala Lys Thr Lys Pro Arg Glu Glu Gln Tyr Asn Ser Thr
                565                 570                 575

Phe Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
        595                 600                 605

Ile Glu Lys Thr Ile Ser Lys Thr Lys Gly Gln Pro Arg Glu Pro Ala
    610                 615                 620

Val Tyr Thr Leu Pro Pro Ser Arg Glu Glu Met Thr Lys Asn Gln Val
625                 630                 635                 640

Lys Leu Val Cys Leu Val Thr Gly Phe Tyr Pro Ser Asp Ile Ala Val
                645                 650                 655

Glu Trp Glu Ser Ser Gly Gln Pro Glu Asn Asn Tyr Tyr Thr Thr Pro
            660                 665                 670

Pro Met Leu Asp Ser Asp Gly Ser Phe Ser Leu Val Ser Trp Leu Asn
        675                 680                 685

Val Asp Lys Ser Arg Trp Gln Gln Gly Asn Ile Phe Ser Cys Ser Val
    690                 695                 700

Met His Glu Ala Leu His Asn Arg Phe Thr Gln Lys Ser Leu Ser Leu
705                 710                 715                 720

Ser Pro Gly

<210> SEQ ID NO 5
<211> LENGTH: 234
<212> TYPE: PRT
<213> ORGANISM: Artificial Sequence
<220> FEATURE:
<223> OTHER INFORMATION: SF3_Lc

<400> SEQUENCE: 5

Met Arg Ser Pro Ala Gln Leu Leu Phe Leu Leu Leu Leu Trp Ile Pro
1               5                   10                  15
```

Gly Thr Asn Ala Asp Ile Gln Met Thr Gln Ser Pro Ser Ser Leu Ser
                20                  25                  30

Ala Ser Val Gly Asp Arg Val Thr Ile Thr Cys Gln Ala Ser Gln Asp
            35                  40                  45

Ile Ser Asn Tyr Leu Asn Trp Tyr Gln Gln Lys Pro Gly Lys Ala Pro
    50                  55                  60

Lys Leu Leu Ile Tyr Asp Ala Ser Asn Leu Glu Thr Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Phe Cys Gln His Phe Asp
            100                 105                 110

His Leu Pro Leu Ala Phe Gly Gly Gly Thr Lys Val Glu Ile Lys Arg
    115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
    195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 6
<211> LENGTH: 246
<212> TYPE: PRT
<213> ORGANISM: Artificial Sequence
<220> FEATURE:
<223> OTHER INFORMATION: SF3_Fc

<400> SEQUENCE: 6

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Glu Val Ala Thr Phe Pro Pro Ser Arg Asp Glu Leu Thr Lys
145                 150                 155                 160

Asn Gln Val Thr Leu Val Cys Leu Val Thr Gly Phe Tyr Pro Ser Asp
            165                 170                 175

Ile Ala Val Glu Trp Glu Ser Asn Gly Gln Pro Glu Asn Asn Tyr Lys
            180                 185                 190

Thr Asp Pro Pro Leu Leu Glu Ser Asp Gly Ser Phe Ala Leu Ser Ser
            195                 200                 205

Arg Leu Arg Val Asp Lys Ser Arg Trp Gln Gln Gly Asn Val Phe Ser
        210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 7
<211> LENGTH: 469
<212> TYPE: PRT
<213> ORGANISM: Artificial Sequence
<220> FEATURE:
<223> OTHER INFORMATION: IgG1 heavy chain sequence

<400> SEQUENCE: 7

Met Glu Ser Pro Ala Gln Leu Leu Phe Leu Leu Leu Leu Trp Leu Pro
1               5                   10                  15

Asp Gly Val His Ala Gln Val Thr Leu Lys Glu Ser Gly Pro Ala Leu
            20                  25                  30

Val Lys Pro Thr Gln Thr Leu Thr Leu Thr Cys Ser Phe Ser Gly Phe
        35                  40                  45

Ser Leu Ser Thr Ser Gly Met Gly Val Gly Trp Ile Arg Gln Pro Pro
    50                  55                  60

Gly Lys Ala Leu Glu Trp Ile Ala His Ile Trp Trp Asp Asp Asp Lys
65                  70                  75                  80

Tyr Tyr Asn Thr Ala Leu Lys Thr Arg Leu Thr Ile Ser Lys Asp Thr
                85                  90                  95

Ser Lys Asn Gln Val Val Leu Thr Met Thr Asn Met Asp Pro Val Asp
            100                 105                 110

Thr Ala Thr Tyr Tyr Cys Ala Arg Ile Asp Trp Asp Gly Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

```
Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly Lys
465

<210> SEQ ID NO 8
<211> LENGTH: 234
<212> TYPE: PRT
<213> ORGANISM: Artificial Sequence
<220> FEATURE:
<223> OTHER INFORMATION: IgG1 light chain sequence

<400> SEQUENCE: 8

Met Glu Ser Pro Ala Gln Leu Leu Phe Leu Leu Leu Leu Trp Leu Pro
1               5                   10                  15

Asp Gly Val His Ala Glu Ile Val Leu Thr Gln Ser Pro Ala Thr Leu
                20                  25                  30

Ser Leu Ser Pro Gly Glu Arg Ala Thr Leu Ser Cys Arg Ala Ser Ser
            35                  40                  45

Ser Val Ser Tyr Met His Trp Tyr Gln Gln Lys Pro Gly Gln Ala Pro
        50                  55                  60

Arg Pro Trp Ile Tyr Ala Thr Ser Asn Arg Ala Thr Gly Ile Pro Ala
65                  70                  75                  80

Arg Phe Ser Gly Ser Gly Ser Gly Thr Asp Tyr Thr Leu Thr Ile Ser
                85                  90                  95

Ser Leu Glu Pro Glu Asp Phe Ala Val Tyr Tyr Cys Gln Gln Trp Ser
                100                 105                 110

Ser Asn Pro Trp Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
        130                 135                 140
```

```
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165             170                 175

Gly Asn Ser Gln Glu Ser Val Thr Glu Gln Asp Ser Lys Asp Ser Thr
            180             185                 190

Tyr Ser Leu Ser Ser Thr Leu Thr Leu Ser Lys Ala Asp Tyr Glu Lys
        195             200             205

His Lys Val Tyr Ala Cys Glu Val Thr His Gln Gly Leu Ser Ser Pro
    210             215             220

Val Thr Lys Ser Phe Asn Arg Gly Glu Cys
225                 230
```

METHODS OF INACTIVATING VIRAL CONTAMINANTS

REFERENCE TO SEQUENCE LISTING SUBMITTED ELECTRONICALLY

The content of the electronically submitted sequence listing (Name 3305_0250001_Seqlisting_ST25; Size: 27,887 bytes; and Date of Creation: Feb. 20, 2020) is incorporated herein by reference in its entirety.

TECHNICAL FIELD

The present invention relates to methods of viral inactivation. In particular, the present invention relates to the production of a virus-free solution containing therapeutic antibodies. The present invention also relates to methods for the production of a bulk drug substance comprising steps of purification of the therapeutic antibody and a viral inactivation treatment.

BACKGROUND

When biomolecules like proteins are used as pharmaceuticals for the treatment of diseases, the production process is designed to assure human health. Cell cultures and other biological materials, typically used for the production of therapeutic proteins, can be contaminated by viruses, either present in the source material or introduced during the production process. If not removed or irreversibly inactivated, the viral contaminates represent a risk to the health of the individuals using the drug. Therefore, to manufacture pharmaceuticals safe for use in humans, the produced proteins are required to be free of active viral contaminates (CPMP/ICH/295/95).

To produce therapeutic proteins, a purification process is carried out to isolate them from the rest of the starting mixed biological material. Steps of the purification, like chromatography and filtration, contribute to virus removal, and are combined with specific viral inactivation techniques to assure viral clearance. Methods for virus inactivation are well known in the art. A way to assure viral inactivation in plasma products consists in treating said plasma products with a solvent/detergent (S/D) mix that impairs viral activity by solubilizing the virus lipid envelope, as established by the World Health Organization (WHO) Technical report, Annex 4 guidelines. Optimizations of this treatment have been carried out to allow S/D treatment of plasma product in a single-use bag system (Hsieh, Y T. et al. Transfusion. 2016 June; 56(6):1384-93); and to treat recombinant Factor VIII in lower temperature and shorter time conditions compared to the ones indicated by WHO Technical report, Annex 4 guidelines (WO2012082931). Additionally, in non-commercial, research scale S/D treatment has been applied as additional virus elimination step of an Anti-D antibody containing sample from human hybridoma cell line (Roberts P L, Biotechnol Prog. 2014 November-December; 30(6): 1341-7). Inactivation can also be achieved by treatment with low pH (Shukla A A at al., Pharm. Bioprocess., 2015, 3(2): 127-138) or high temperatures (Pasteurization) (U.S. Pat. No. 4,749,783) that lead to viral proteins denaturation. These treatments are effective against enveloped and non-enveloped viruses, but they may not be compatible with all therapeutic proteins as these can also be susceptible to denaturation.

An important class of therapeutic proteins are monoclonal antibodies, which can have a natural structure, like the one of the antibodies produced by an animal body, and those which have been engineered to enhance their properties in multiple ways. Antibodies can be used as drugs for the treatment and diagnosis of a variety of diseases including different types of cancer and disorders of the immune system. Monoclonal antibodies are normally produced commercially using transfected cell lines, comprising the coding sequence of the antibody, which are grown at large scale under controlled cell culture conditions and then harvested. Following harvest, the antibody is purified and in the purification process a standard procedure for viral inactivation includes the incubation of the sample at low pH (WO2010048192; Liu H F et al. MAbs. 2010 September-October; 2(5):480-99).

Antibodies can be susceptible to non-physiological conditions such as low pH and when engineered to have enhanced effector function or to preferentially form heterodimers rather than homo-dimers, they can be more prone to degradation. As antibody-based therapeutics continue to expand and as the complexity of these products also expands, the development of new viral inactivation strategies is required.

Additionally, the purification process of a therapeutic protein, such as an antibody, may be not compatible with the low pH commonly used for viral inactivation, therefore making available alternative virus inactivation methods would facilitate the development and improvement of the purification process.

The present invention relates to new methods of viral inactivation for antibodies produced commercially, for which existing viral inactivation approaches do not work or lead to degradation of the antibody product or to some other unwanted outcomes or are not compatible the antibody purification process.

SUMMARY

The present invention is related to new methods of viral inactivation adopted in the purification process of therapeutic proteins, such as antibodies. The classical method used in the process of antibody purification is the incubation of the antibody-containing solution at low pH. Nevertheless, the optimization of the purification process may lead to the development of steps which are not compatible with low pH. Additionally, it has been observed that for low pH-liable antibodies, this method is not suitable since impairs the stability of the antibody. The new methods of viral inactivation presented in this invention allow overcoming these problems.

Particularly, the present invention relates to methods for preparing an antibody solution free of viral contaminations during the process of antibody purification, where the preparation of said virus-free antibody solution starts from a culture of transfected cells expressing the antibody and includes the steps of (i) harvesting antibody material produced by transfected cells and (ii) treating the antibody harvest material by solvent detergent or high pH.

More in particular, the present invention relates to a method of preparing a virus-inactivated antibody solution, comprising the steps of (i) harvesting antibody material produced by transfected cells comprising the coding sequences of said antibody, which have undergone cell culture, (ii) a viral inactivation treatment upon said harvested antibody material, selected from the group consisting of incubation with a mixture of a solvent and a detergent or incubation at high pH.

In one embodiment the harvested antibody material of the present invention is produced in non-human mammalian cells.

In another embodiment, the harvested antibody material of the present invention comprises a monoclonal antibody. In a more specific embodiment the monoclonal antibody is a recombinant antibody. In a specific aspect, said recombinant antibody is multispecific.

In one embodiment of the present invention, the harvested antibody material is incubates with a mixture of a solvent and a detergent, wherein said solvent is TnBP and, wherein said detergent is selected from the group consisting of Triton X-100, Polysorbate 80 and Polysorbate 20.

In a more specific embodiment, the concentration of said TnBP is equal to or greater than about 0.1% (w/w), and equal to or less than about 1% (w/w), in particular the concentration of said TnBP is selected from the group comprising: about 0.1% (w/w), about 0.3% (w/w), about 0.5% (w/w) and about 1% (w/w).

In another specific embodiment, the concentration of said Polysorbate 80 or said Polysorbate 20 is equal to or greater than about 0.1% (w/w), and equal to or less than about 2% (w/w), in particular the concentration of said Polysorbate 80 or said Polysorbate 20 is selected from the group comprising: about 0.2%, about 0.5% (w/w), about 0.75% (w/w), about 1% (w/w), about 1.25% (w/w).

In a more specific embodiment, said mixture of a solvent and a detergent is selected from the group consisting of mixture of 0.3% (w/w) TnBP and 0.5% (w/w) Polysorbate 80 and mixture of 0.3% (w/w) TnBP and 1% (w/w) Polysorbate 80.

In an even more specific, said harvested antibody material is incubated with a mixture of 0.3% (w/w) TnBP and 1% (w/w) Polysorbate 80 for at least 5 minutes.

In a particular embodiment, said harvested antibody material is first subjected to protein A chromatography, and wherein the resulting protein A eluate is incubated with a mixture of 0.3% (w/w) TnBP and 1% (w/w) Polysorbate 80 for at least 10 minutes at room temperature.

In another particular embodiment, said harvested antibody material is the clarified harvest and is incubated with a mixture of 0.3% (w/w) TnBP and 1% (w/w) Polysorbate 80 for about 60 minutes, under agitation, at room temperature.

In one embodiment of the present invention, the harvested antibody material is incubates with high pH, wherein high pH a pH at or above 9 and at or below 12.5. More specifically, said high pH is at least 10.5. Even more specifically said high pH is about 11.

In a specific embodiment, the harvested antibody material according to the present invention is first subjected to protein A chromatography, and the resulting A eluate is incubated at said high pH.

In one aspect of the present invention, said protein A eluate is titrated with a buffer selected from the group of: Tris, Histidine L-Arginine, phosphate and NaOH to the target high pH and incubated.

In a more specific aspect of the present invention said protein A eluate is titrated with NaOH 0.5M to target pH 11, for about 60 min at room temperature.

In one embodiment, the method of the present invention comprises a further step (iii) of testing a portion of the virus-inactivated antibody solution with a viral inactivation assay.

The present invention also relates to a method of production of a bulk drug substance comprising the steps of:
(a) Viral inactivation of the harvested antibody material by solvent detergent treatment as in claim 13.
(b) Protein A chromatography of the resulting viral inactivated solution.
(c) Neutralization of the protein A eluate to pH 6.0, followed by 0.2 μm filtration.
(d) Cation exchange chromatography of the neutralized protein A eluate, followed by 0.2 μm filtration.
(e) Concentration of the cation exchange chromatography eluate by ultrafiltration and continuous diafiltration, followed by 0.2 μm filtration.
(f) Purification of the product by anion exchange chromatography in flow through mode, using membrane adsorption, followed by 0.2 μm filtration.
(g) Virus nanofiltration.
(h) Concentration of the product by ultrafiltration and continuous diafiltration into pre-formulation buffer, followed by 0.2 um filtration.
(i) Excipient addition to target 6 mg/mL of the product in the final formulation buffer, by mixing 5 mM Citrate, 15% Sucrose, 0.06% Polysorbate 80 at pH 5.9, followed by 0.2 μm filtration.
(j) Filling of the product into sterile bags, followed by freezing and storage at −80±20° C.

Also disclosed by the present invention is a method of production of a bulk drug substance comprising the steps of:
(a) Protein A chromatography of the harvested antibody material.
(b) Incubation of the resulting PA eluate at high pH.
(c) Neutralization of the resulting viral inactivated solution to pH5.5, followed by 0.2 μm filtration.
(d) Cation exchange chromatography of the neutralized viral inactivated protein A eluate, followed by 0.2 μm filtration.
(e) Concentration of the cation exchange chromatography eluate by ultrafiltration and continuous diafiltration, followed by 0.2 μm filtration.
(f) Purification of the product by anion exchange chromatography in flow through mode, using membrane adsorption, followed by 0.2 μm filtration.
(g) Virus nanofiltration.
(h) Concentration of the product by ultrafiltration and continuous diafiltration into pre-formulation buffer, followed by 0.2 um filtration.
(i) Excipient addition to target 6 mg/mL of the product in the final formulation buffer, by mixing 5 mM L-Histidine, 150 mM L-Arginine Monohydrochloride, 15% Sucrose, 0.06% Polysorbate 80, pH 6.0, followed by 0.2 μm filtration.
(j) Filling of the product into sterile bags, followed by freezing and storage at −80±20° C.

Also disclosed by the present invention is a liquid pharmaceutical formulation comprising a monoclonal antibody, a buffer, a surfactant, and a stabilizing agent, wherein said monoclonal antibody is present in said pharmaceutical formulation at a concentration equal to or greater than about 0.01 mg/mL and equal to or less than about 100 mg/mL, preferably at a concentration of about 6 mg/mL, said buffer is Citrate present in said pharmaceutical formulation at concentration of about 5 mM, said surfactant is Polysorbate present in said pharmaceutical formulation at a percentage of about 0.06%, and said stabilizing agent is Sucrose present in said pharmaceutical formulation at a percentage of about 15%, and wherein said pharmaceutical formulation has a pH of about 5.9.

Also disclosed by the present invention is a liquid pharmaceutical formulation comprising a monoclonal antibody, a buffer, a surfactant, and stabilizing agents, wherein said monoclonal antibody is present in said pharmaceutical formulation at a concentration equal to or greater than about 0.01 mg/mL and equal to or less than about 100 mg/mL, preferably at a concentration of about 6 mg/mL, said buffer is L-Histidine, present in said pharmaceutical formulation at concentration of about 5 mM, said surfactant is Polysorbate present in said pharmaceutical formulation at a percentage of about 0.06%, and said stabilizing agents are Sucrose present in said pharmaceutical formulation at a percentage of about 15% and L-Arginine Monohydrochloride present in said pharmaceutical formulation at a concentration of about 120 mM and wherein said pharmaceutical formulation has a pH of about 6.0.

Additionally, the present invention relates to a method of removal of impurities from a cell harvest material comprising the step of treating said cell harvest with high pH followed by a filtration step.

In the present invention, the term "antibody" and the term "immunoglobulin" are used interchangeably. The term "antibody" as referred to herein, includes the full-length antibody and antibody fragments. Antibodies are glycoproteins produced by plasma cells that play a role in the immune response by recognizing and inactivating antigen molecules. In mammals, five classes of immunoglobulins are produced: IgM, IgD, IgG, IgA and IgE. In the native form, immunoglobulins exist as one or more copies of a Y-shaped unit composed of four polypeptide chains: two identical heavy (H) chains and two identical light (L) chains. Covalent disulfide bonds and non-covalent interactions allow interchain connections; particularly heavy chains are linked to each other, while each light chain pairs with a heavy chain. Both heavy chain and light chain comprise an N-terminal variable (V) region and a C-terminal constant (C) region. In the heavy chain, the variable region is composed of one variable domain (VH), and the constant region is composed of three or four constant domains (CH1, CH2, CH3 and CH4), depending on the antibody class; while the light chain comprises a variable domain (VL) and a single constant domain (CL). The variable regions contain three regions of hypervariability, termed complementarity determining regions (CDRs). These form the antigen binding site and confer specificity to the antibody. CDRs are situated between four more conserved regions, termed framework regions (FRs) that define the position of the CDRs. Antigen binding is facilitated by flexibility of the domains position; for instance, immunoglobulin containing three constant heavy domains present a spacer between CH1 and CH2, called "hinge region" that allows movement for the interaction with the target. Starting from an antibody in its intact, native form, enzymatic digestion can lead to the generation of antibody fragments. For example, the incubation of an IgG with the endopeptidase papain, leads to the disruption of peptide bonds in the hinge region and to the consequent production of three fragments: two antibody binding (Fab) fragments, each capable of antigen binding, and a cristallizable fragment (Fc). Digestion by pepsin instead yields one large fragment, F(ab')2, composed by two Fab units linked by disulfide bonds, and many small fragments resulting from the degradation of the Fc region. Depending on their nature, antibodies and antibody fragments can be monomeric or multimeric, monovalent or multivalent, monospecific or multispecific.

The term "full-length antibody" as used herein, includes antibodies in their native intact structure that comprises at least two pairs of heavy and light chains.

The term "antibody fragments" as used herein, includes one or more portion(s) of a full-length antibody. Non limiting examples of antibody fragments include: (i) the fragment crystallizable (Fc) composed by two constant heavy chain fragments which consist of CH2 and CH3 domains, in IgA, IgD and IgG, and of CH2, CH3 and CH4 domains, in IgE and IgM, and which are paired by disulfide bonds and non-covalent interactions; (ii) the fragment antigen binding (Fab), consisting of VL, CL and VH, CH1 connected by disulfide bonds; (iii) Fab', consisting of VL, CL and VH, CH1 connected by disulfide bonds, and of one or more cysteine residues from the hinge region; (iv) Fab'-SH, which is a Fab' fragment in which the cysteine residues contain a free sulfhydryl group; (v) F(ab')2 consisting of two Fab fragments connected at the hinge region by a disulfides bond; (vi) the variable fragments (Fv), consisting of VL and VH chains, paired together by non-covalent interactions; (vii) the single chain variable fragments (scFv), consisting of VL and VH chains paired together by a linker; (ix) the bispecific single chain Fv dimers, (x) the scFv-Fc fragment; (xi) a Fd fragment consisting of the VH and CH1 domains; (xii) the single domain antibody, dAb, consisting of a VH domain or a VL domain; (xiii) diabodies, consisting of two scFv fragments in which VH and VL domains are connected by a short peptide that prevent their pairing in the same chain and allows the non-covalent dimerization of the two scFvs; (xiv) the trivalent 10 triabodies, where three scFv, with VH and VL domains connected by a short peptide, form a trimer. (xv) half-IgG, comprising a single heavy chain and a single variable chain.

The term "homo-dimeric antibody" or "homo-dimeric fragment" or "homo-dimer" as used herein includes an immunoglobulin molecule or part of comprising at least a first and a second polypeptide, like a first and a second domain, wherein the second polypeptide is identical in amino acid sequence to the first polypeptide. Preferably, a homo-dimeric immunoglobulin comprises two polypeptide chains, wherein the first chain has at least one identical domain to the second chain, and wherein both chains assemble, i.e. interact through their identical domains. Specifically, a homo-dimeric immunoglobulin comprises at least two identical domains and wherein both domains assemble, i.e. interact through their protein-protein interfaces. Preferably, a homo-dimeric immunoglobulin fragment comprises at least two domains, wherein the first domain is identical to the second domain, and wherein both domains assemble, i.e. interact through their protein-protein interfaces.

The term "hetero-dimeric antibody" or "hetero-dimeric fragment" or "hetero-dimer" as used herein includes an immunoglobulin molecule or part of comprising at least a first and a second polypeptide, like a first and a second domain, wherein the second polypeptide differs in amino acid sequence from the first polypeptide. Preferably, a hetero-dimeric immunoglobulin comprises two polypeptide chains, wherein the first chain has at least one non identical domain to the second chain, and wherein both chains assemble, i.e. interact through their non-identical domains. Specifically, a hetero-dimeric immunoglobulin comprises at least two domains, wherein the first domain is non identical to the second domain, and wherein both domains assemble, i.e. interact through their protein-protein interfaces. More preferably the hetero-dimeric immunoglobulin, has binding specificity for at least two different ligands, antigens or binding sites, i.e. is bispecific.

The term "valence" as used herein, refers to the number of binding sites in the antibody. An antibody that has more than one valence is called multivalent; non-limiting examples of multivalent antibodies are: bivalent antibody, characterized by two biding sites, trivalent antibody, characterized by three binding sites, and tetravalent antibody, characterized by four binding sites.

The term "monospecific antibody" as used herein, refers to any antibody or fragment having one or more binding sites, all binding the same epitope.

The term "multispecific antibody" as used herein, refers to any antibody or fragment having more than one binding site that can bind different epitopes of the same antigen, or different antigens. A non-limiting example of multispecific antibodies are bispecific antibody.

The term "bispecific antibody" refers to any antibody having two binding sites that can bind two different epitopes of the same antigen, or two different antigens.

The term "antigen" as used herein, refers to any molecule to which an antibody can specifically bind. Examples of antigens include polypeptides, proteins, polysaccharides and lipid molecules. In the antigen one or more epitopes can be present. The term "epitope" or "antigenic determinant" as used herein, refers to the portion of the antigen that makes the direct chemical interaction with the antibody.

The term "monoclonal antibody" as used herein, refers to antibodies that are produced by clone cells all deriving from the same single cell, and that specifically bind the same epitope of the target antigen. When therapeutic antibodies are produced, the generation of monoclonal antibodies is preferred over polyclonal antibodies. In fact, while monoclonal antibodies are produced by cells originating from a single clone and bind all the same epitope, polyclonal antibodies are produced by different immune cells and recognize multiple epitopes of a certain antigen. Monoclonal antibodies assure batch to batch homogeneity, reduced cross-reactivity and high specificity toward the target. Monoclonal antibodies can be expressed, for instance in host cells, using recombinant DNA, giving rise to a recombinant antibody.

The term "recombinant antibody" as used herein, refers to an antibody that has been produced by any process involving the use of recombinant DNA. A recombinant antibody can be engineered in such a way to improve characteristics such as immunogenicity, binding affinity, molecular size, specificity, half-life, and format. Examples of recombinant antibodies include, but are not limited to engineered antibodies, chimeric antibodies, CDRs grafted antibodies (such as humanized antibodies), fully human antibodies, antibody fragments, Fc-engineered antibodies, multispecific antibody (such as bispecific, trispecific, tetraspecific antibody), monomeric and multimeric antibodies (such as homo-dimeric and hetero-dimeric antibodies).

The term "chimeric antibody" as used herein, refers to an antibody in which the variable region is derived from one species and it is fused to a constant region derived from another species; a non-limiting example of chimeric antibody is an antibody in which a murine variable region is fused to a human constant region.

The term "CDRs grafted antibody" as used herein, refers to an antibody in which CDRs derived from one species are grafted in the framework region of another species; a non-limiting example of CDRs grafted antibody is a humanized antibody in which CDRs from a mammalian species, such as mouse, are grafted in a human framework region.

The term "cell transfection" refers to the introduction of foreign genetic material into eukaryotic cells. When the protein codified by the artificially introduced nucleic acid is expressed by the cells, it provides the genetically modified cells with properties different than the respective wild type form. The introduced nucleic acid can be DNA or RNA. Examples of techniques commonly used for introducing exogenous nucleic acid into the host cells include chemical-based methods, where the transfection is mediated by transfection reagents such calcium-phosphate, liposomes, cationic polymers or dendrimers; physical-based method such as electroporation and microinjection; and virus-based methods where virus infection mediates gene delivery. Using these techniques, transient or stable transfection can be achieved. In the transient transfection the nucleic acid sequence does not integrate into the genome of the host cell, therefore the expression of the protein codified by the exogenous genetic material is limited in time, while stable transfection is achieved when the cells integrate the foreign genetic material in their genome, giving rise to a stable transfected cell line.

The term "host cells" refers to all the cells in which the protein codified by the transfected nucleic acid material is expressed, including those cells in which the foreign nucleic acid is directly introduced and their progeny. Cell lines suitable for the expression of the antibody include and are not limited to bacteria, mammalian, insect, plant and yeast cells. Cell lines often used for the expression and production of therapeutic antibodies are mammalian cells lines such as Chinese hamster ovary (CHO) cells, NSO mouse myeloma cells, human cervical carcinoma (HeLa) cells and human embryonic kidney (HEK) cells. Host cells are cultured in conditions that aid their growth and the expression of the antibody. Optimal culturing conditions are obtained by the control and adjustment of several parameters including: the formulation of the cell culture medium, the bioreactor operating parameters, the nutrient supply modality and the culturing time period. The formulation of the culturing medium has to be optimized to favorite cell vitality and reproduction; examples of constituents of the cell culture medium include but are not limited to essential amino acids, salts, glucose, growth factors and antibiotics. Important bioreactor operating parameters are: temperature, pH, agitation speed, oxygenation and carbon dioxide levels. Nutrients can be supplied in different ways: in the batch mode culture all the necessary nutrients are present in the initial base medium and are used till exhausted while wastes accumulate; in the fed-batch culture additional feed medium is supplied to prevent nutrient depletion and prolong the culture; differently, in the perfusion modality, cells in culture are continuously supplemented with fresh medium containing nutrients that flows in the bioreactor removing cell wastes. The culturing period is important as it needs to be long enough to let the cells produce a consistent amount of product but it cannot be too long to impair cell viability.

The term "harvested antibody material", refers to the material, obtained by the cell culture, containing the antibody expressed by the host cells. The harvested antibody material may be produced by first harvesting the host cell culture and then subjecting the harvest to a process of clarification which allows the removal of cell debris through steps of centrifugations and/or filtrations.

The term "viral clearance" refers to any treatment that effectively remove and/or inactivate viruses which could contaminate the material of interest. When applied in the purification process of a therapeutic antibody, virus clearance refers to any method that lead to viral inactivation or viral removal from an antibody-containing material.

The term "viral inactivation" refers to any treatment that makes a virus unable to infect biological samples or to replicate. Viral inactivation can be achieved by different techniques such as the incubation of the biological sample with solvents and detergents (S/D), which causes viral inactivation trough the solubilization of the viral envelope; the incubation in low or high pH, which leads to the denaturation of the viral proteins; the pasteurization treatment, in which viral protein denaturation is achieved by high temperatures.

The term "incubation" refers to the operation of keeping a material in certain conditions, comprising conditions for which the material undergoes modifications. In the process of viral inactivation, the incubation of a material with a solution having chemical characteristics that cause viral inactivation, leads to the generation of a material free of active viral contaminants.

The term "solvent detergent treatment" refers to the incubation of the harvested antibody material with a solvent, such as an organic solvent or with an organic solvent and a detergent.

The term "high pH treatment" refers to the incubation of the harvested antibody material with a buffer solution with pH greater than 7.

The term "virus removal" refers to any treatment that allows the physical separation of the viral particles from the treated sample. In the process of therapeutic protein purification, virus removal is accomplished by filtration steps. Additionally other phases of the purification process, such as chromatography steps, aid the removal of viral particles.

The term "filtration" refers to the operation of separating the solids from a fluid.

The term "chromatography" refers to the operation of separating compounds of a mixture based on their capability to interact with a stationary phase of a chromatography column, from which they can be retained or eluted.

The terms "viral inactivation assay" and "viral removal validation (VRV)" as used herein are interchangeable and refer to a procedure for testing the effective virus reduction. To perform viral inactivation assays, the viral presence in the samples is measured before and after spiking with a known quantity of stock virus and by comparing the output viral titre against the respective load viral titre. A $\log_{10}$ reduction factor (RF) may be then determined according to the following formula: RF=$\log_{10}${Input virus titre X Input volume/ Output virus titre X Output volume. The inactivation/removal of viruses can be described as: "effective", when RF is greater than 4 $\log_{10}$; "moderately effective", when RF is included between 2 $\log_{10}$ and 4 $\log_{10}$; "contributing to virus reduction", RF is included between 1 $\log_{10}$ and 2 $\log_{10}$; and "ineffective", when RF is less than 1 $\log_{10}$.

In the present invention, the starting antibody harvest material comprises a monoclonal antibody. Preferably the monoclonal antibody is recombinant. In a specific embodiment of the present invention, the monoclonal recombinant antibody is a hetero-dimeric bispecific antibody.

In the present invention, the hetero-dimeric bispecific antibody may be generated by BEAT® technology (WO2012131555). In one embodiment of this invention, the bispecific antibody, referred to as BEAT® 1, binds the cluster of differentiation 3 (CD3) expressed by T-cells and the human epidermal growth factor receptor 2 (HER2), often overexpressed in breast cancer cells. In another embodiment, the monoclonal bispecific antibody, referred to as BEAT®2 (SEQ ID NOs: 1, 2 and 3), binds CD3 and the cluster of differentiation 38 (CD38), overexpressed in multiple myeloma cells. In another embodiment, the monoclonal bispecific antibody is BEAT®3 (SEQ ID NOs: 4, 5 and 6), which binds to CD3 and EGFR, known to be a target in different types of cancers, including colorectal cancer. In another embodiment, the monoclonal antibody, referred to as Ab1 (SEQ ID NOs: 7 and 8) is an IgG1 that targets OX40 receptor, involved in autoimmune and inflammatory disorders.

The antibody of the present invention is expressed in host cells upon cell transfection. Cell transfection methods adopted in this invention include but are not limited to chemical-based methods exploiting a transfection reagent. Transfection reagents suitable for this invention include but are not limited to calcium-phosphate, liposome, cationic polymers and dendrimers. In one embodiment of this invention, cell transfection is carried out by a cationic polymers. Non limiting examples of a cationic polymer are diethylethanolamine and polyethylenimine. In a specific embodiment of this invention, the cation polymer is polyethylenimine.

In accordance with a particular aspect of the present invention, the host cell lines utilized for antibody production include but are not limited to eukaryotic cell lines. In one embodiment of this invention, the host cell lines are mammalian cell lines. In a more specific embodiment, the mammalian cell line is a non-human cell line. In an even more specific embodiment of this invention, the mammalian cell line is CHO cell line, particularly CHO-S cell line.

The host cells of the present invention, may be cultured in a 250 L working volume single use bioreactor containing animal derived component free (ADCF) medium, where the dissolved $O_2$ is maintained at 40% of air saturation and the temperature is maintained at 37° C. The culture may be a feed-batch culture, where feeds are initiated at day 3 post inoculation. Daily boluses of feeds are added to the bioreactor. The culture is harvested either 11 days post-feed initiation or when the cell viability reaches 80% or 85%.

In the present invention the virus-inactivated antibody solution may be prepared starting from a harvested antibody material. Particularly, the harvested antibody material is the product of the clarification of the bulk harvest of the host cell culture. In a specific embodiment of the present invention, the harvested antibody material is prepared by clarifying the bulk harvest through filtration steps including "dead end" depth filtration, followed by aseptically filtration through a 0.2 μm filter.

The harvested antibody material may be loaded onto a chromatography column. In certain embodiments of this invention the harvested antibody material is loaded into a protein A (PA) chromatography. The harvested antibody material loaded onto a protein A chromatography is also called "PA load". The collected solution is called "PA eluate". In this invention, the resin of protein A chromatography is first equilibrated to pH 7.4 with phosphate buffered saline (PBS). In a certain embodiment of this invention, the column is then washed (for instance by Tris and/or Acetate) and the antibody is eluted from the column using elution buffers such as Glycine or Acetate. In one aspect of the present invention the protein A eluate is neutralized to a pH equal to or greater than about 5 and equal to or less than 7; more specifically to a pH equal to or greater than 5.5 and equal to or less than 6.5.

In a preferred embodiment of this invention, viral inactivation is carried out by solvent detergent treatment. Organic solvents useful in the method disclosed herein include dialkylphosphates like tri-(n-butyl) phosphate (TnBP). The concentration of the organic solvent may be equal to or greater than about 0.1% (w/w) and equal to or less than about 1% (w/w). In particular the concentration of the organic solvent is selected from the group consisting of: about 0.1% (w/w), about 0.2% (w/w), about 0.3% (w/w), about 0.4% (w/w), about 0.5% (w/w), about 0.6% (w/w), about 0.7% (w/w), about 0.8% (w/w), about 0.9% (w/w) or about 1% (w/w). More in particular, the concentration the organic solvent is at least about 0.1% (w/w), at least about 0.3% (w/w), at least about 0.5% (w/w), or at least about 1% (w/w). In certain preferred embodiments, the concentration of the organic solvent is equal to or greater than about 0.2% (w/w) and equal to or less than about 0.4% (w/w). In particular, the concentration of the organic solvent is about 0.2% (w/w), or about 0.3% (w/w), or about 0.4% (w/w). More preferably the concentration of the organic solvent is about 0.3% (w/w). The present invention also includes the concentrations of the organic solvent at intervals of 0.1% (w/w), 0.2% (w/w), 0.3% (w/w), 0.4% (w/w), 0.5% (w/w), 0.6% (w/w), 0.7% (w/w), 0.8% (w/w), 0.9% (w/w) or 1% (w/w) between the above cited concentrations.

Detergents useful in the method disclosed herein include non-ionic surfactants like polyoxeethylene glycol sorbitan alkyl esters, including polysorbates such as Polysorbate 20 (such as Tween 20®), Polysorbate 40 (such as Tween 40®), Polysorbate 60 (such as Tween 60®), and Polysorbate 80 (such as Tween 80®); and polyoxyethylene octyl phenyl ether (such as Triton® X-100). The terms "Polysorbate" and "Tween" as used herein are iterchangable. The concentration of the detergent is equal to or greater than about 0.1% (w/w) and equal to or less than about 2% (w/w); in particular the concentration of the detergent is equal to or greater than 0.2% (w/w) and equal to or less than 1.5% (w/w). I a more specific embodiment of the present invention, the concentration of the detergent is equal to or greater than 0.75% (w/w) and equal to or less than 1.25% (w/w). More specifically, the concentration of the detergent is selected from the group consisting of: about 0.1% (w/w), about 0.2% (w/w), about 0.3% (w/w), about 0.4% (w/w), about 0.5% (w/w), about 0.6% (w/w), about 0.7% (w/w), about 0.8% (w/w), about 0.9% (w/w), about 1% (w/w), about 1.2% (w/w), about 1.5% (w/w), about 1.7% (w/w), or about 2% (w/w). More in particular, the concentration the organic solvent is at least about 0.2% (w/w), at least about 0.5% (w/w), at least about 0.75% (w/w), at least about 1% (w/w), or at least about 1.25% (w/w). In certain preferred embodiments, the concentration of the detergent is about 0.75% (w/w), or about 1% (w/w), or about 1.25% (w/w). In a more preferred embodiment the concentration of the detergent is about 1% (w/w). The present invention also includes the concentrations of the organic solvent at intervals of 0.05% (w/w), 0.1% (w/w), 0.2% (w/w), 0.3% (w/w) 0.4% (w/w) 0.5% (w/w), 0.6% (w/w), 0.7% (w/w), 0.8% (w/w), 0.9% (w/w) or 1% (w/w) between the above cited concentrations.

In one aspect of the present invention, the antibody-containing material is incubated with a solvent, or a detergent, or a mixture of solvent and detergent for an incubation time equal to or greater than about 5 minute and equal to or less than about 120 minutes. Specifically, the incubation time is selected from the group comprising about 5 minutes, about 10 minutes, about 20 minutes, about 30 minutes, about 60 minutes, about 90 minutes and about 120 minutes. More specifically, said incubation time is at least about 5 minutes, at least about 10 minutes, at least about 20 minutes, at least about 30 minutes, at least about 60 minutes, at least about 90 minutes and at least about 120 minutes. Even more specifically, the incubation time is equal to or greater than 30 minutes and equal to or less than 90 minutes, preferably the incubation time is 60 minutes. The present invention also includes the solvent and detergent incubation time at intervals of 1, 2, 5, 10, 15, 30, 60, 75 or 90 minutes between the above cited incubation intervals.

In one embodiment of this invention, the antibody-containing solution is treated with TnBP and Triton X-100 such that the final concentration is about 0.3% (w/w) TnBP and about 0.2% (w/w) to about 1% (w/w) Triton X-100. In another aspect of this embodiment, the solution containing the antibody is treated with TnBP and Polysorbate 80 such that the final concentration is about 0.3% (w/w) TnBP and about 0.2% (w/w) to about 1% (w/w) Polysorbate 80. In another aspect of this embodiment, the antibody-containing solution is treated with TnBP and Polysorbate 20 such that the final concentration is about 0.3% (w/w) TnBP and about 0.2% (w/w) to about 1% (w/w) Polysorbate 20.

In an aspect of this invention, the solution containing the antibody is the PA eluate. In a specific aspect, the PA eluate is treated with about 0.1% (w/w) TnBP, or about 0.3% (w/w) TnBP, or about 0.5% (w/w) TnBP, or about 1% (w/w) TnBP, or about 0.3% (w/w) TnBP and about 0.2% (w/w) Triton X-100, or about 0.3% (w/w) TnBP and about 0.5% (w/w) Triton X-100, or about 0.3% (w/w) TnBP and about 1% (w/w) Triton X-100, or about 0.3% (w/w) TnBP and about 0.2% (w/w) Polysorbate 80, or about 0.3% (w/w) TnBP and about 0.5% (w/w) Polysorbate 80, or about 0.3% (w/w) TnBP and about 1% (w/w) Polysorbate 80, or about 0.3% (w/w) TnBP and about 0.2% (w/w) Polysorbate 20, or about 0.3% (w/w) TnBP and about 0.5% (w/w) Polysorbate 20, or about 0.3% (w/w) TnBP and about 1% (w/w) Polysorbate 20. In a more specific aspect, the PA eluate is treated with about 0.3% (w/w) TnBP in combination with about 0.2% (w/w) Triton X-100 or about 0.5% (w/w) Triton X-100 or about 0.5% (w/w) Polysorbate 80, or about 1% (w/w) Polysorbate 80, or about 0.2% (w/w) Polysorbate 20, or about 0.5% (w/w) Polysorbate 20, or about 1% (w/w) Polysorbate 20.

In a more specific aspect of the present invention, the solution containing the antibody is the PA eluate and the PA eluate is incubated with a mixture of 0.3% (w/w) TnBP and 1% (w/w) Polysorbate 80 for at least 10 minutes at room temperature, preferably for about 60 minutes at room temperature.

In another aspect of this invention, the solution containing the antibody is the PA load and the PA load is treated with about 0.3% (w/w) TnBP in combination with about 1% (w/w) Triton X-100, or about 1% (w/w) Polysorbate 80, or about 1% (w/w) Polysorbate 20.

In a particular aspect of the present invention the PA load is incubated with a solvent, or a detergent, or a mixture of solvent and detergent for an incubation time as previously specified.

Additionally said PA load incubated with said solvent, or said detergent, or said mixture of solvent and detergent is loaded onto the PA chromatography column and the loading duration is equal to or less than about 7 hours. In a certain embodiment the loading duration is about 3 hours. Preferably the sum of the incubation time and the loading duration is equal or less than 7 hours.

In a more specific aspect of this invention, the solution containing the antibody is the PA load and the PA load is incubated with a mixture of 0.3% (w/w) TnBP and 1% (w/w) Polysorbate 80 for at least 5 minutes, preferably for about 60 minutes at room temperature before being loaded onto a PA chromatography column.

In another embodiment of this invention, the method of viral inactivation is high pH treatment. Buffer solutions useful in the method disclosed herein include alkaline solution including, but not limited to acetate, citrate, Tris, Histidine, L-Arginine, phosphate, NaOH. The pH of the buffer solution may be equal to or greater than about 7.5 and equal to or less than about 14. In particular, the pH of the buffer solution is selected from the group of about 7.5, about 8, about 8.5, about 9, about 9.5, about 10, about 10.5, about 11, about 11.5, about 12, about 12.5, or about 13, or about 13.5, or about 14. In a more specific embodiment the pH of the buffer solution is equal to or greater than about 10 and equal to or less than about 12; more specifically the pH of the buffer solution is equal to or greater than about 10.5 and equal to or less than about 11.5. Specifically, the pH of the buffer solution is at least 10.5; more specifically the pH of the buffer solution is about 11.5; more preferably about 11.2; even more preferably about 11. The present invention also includes the pH values at intervals of 0, 1, 0.2, 0.3, 0.4, 0.5, 0.6, 0.7, 0.8, 0.9 or 1 between the above cited pH values. In a specific aspect of this embodiment, the solution containing the antibody is the PA eluate and the PA eluate is treated with Phosphate 250 mM, NaOH 0.1 M and NaOH 0.5 M.

In one embodiment of the present invention, the antibody-containing material is incubated at high pH for an incubation time equal to or greater than about 1 minute and equal to or less than about 4 hours. Specifically, the incubation time is selected from the group comprising about 1 minute, about 5 minutes, about 10 minutes, about 30 minutes, about 45 minutes, about 60 minutes, about 90 minutes, about 2 hours, about 3 hours and about 4 hours. More specifically, said incubation time is at least about 1 minute, at least about 5 minutes, at least about 10 minutes, at least about 30 minutes, at least about 45 minutes, at least about 60 minutes, at least about 90 minutes, at least about 2 hours, at least about 3 hours and at least about 4 hours. Even more specifically, the incubation time is equal to or greater than 30 minutes and equal to or less than 90 minutes, preferably the incubation time is 60 minutes. The present invention also includes the high pH incubation time at intervals of 1, 5, 10, 15, 30, 60, 75, 90 or 120 minutes between the above cited incubation intervals.

Following protein A chromatography and viral inactivation treatment, or following viral inactivation treatment and protein A chromatography the solution containing the antibody may be further treated by other chromatography and filtration steps to further purify and concentrate the antibody for producing a bulk drug substance containing the therapeutic antibody. In an aspect of the present invention, methods of production of a bulk drug substance are disclosed. The method of production of a bulk drug substance may comprise the consequent steps of (a) viral inactivation by solvent detergent treatment, (b) protein A chromatography purification, (c) cation exchange chromatography (CEX), (d) ultrafiltration/diafiltration (UF/DF), (e) anion exchange membrane absorber, (f) virus nanofiltration, (g) UF/DF, (h) excipient addition and concentration adjustment; or the consequent steps of (a') protein A chromatography purification, (b') viral inactivation by solvent detergent treatment, (c') CEX, (d') UF/DF, (e') anion exchange membrane absorber, (f') virus nanofiltration, (g') UF/DF, (h') excipient addition and concentration adjustment; or the consequent steps of (a") protein A chromatography purification, (b") high pH treatment, (c") CEX, (d") UF/DF, (e") anion exchange membrane absorber, (f") virus nanofiltration, (g") UF/DF, (h") excipient addition and concentration adjustment.

In a more specific aspect of this invention, the method of production of a bulk drug substance consists of firstly performing viral inactivation of the harvested antibody material by solvent detergent treatment with TnBP 0.3% (w/w) and Polysorbate 80 1% (w/w) for 60 min under agitation. Then, protein A chromatography of the viral inactivated solution is performed and the resulting PA eluate is neutralized to pH 6.0 and 0.2 μm filtered; next the neutralized intermediate PA eluate is loaded onto a cation exchange chromatography column and the product is passed through a 0.2 μm filter. The antibody is then concentrated to a target of 25 mg/mL and dialyzed with a 50 mM Histidine pH 6.5 by an ultrafiltration/diafiltration (UF/DF) system. The product is then 0.2 μm filtered and purified on a positively-charged NatriFlo single-use membrane for anion exchange (AEX) chromatography in flow-through mode. The eluate is subsequently 0.2 μm filtered. Next, the product is nanofiltered through a Virosart® HF connected aseptically to a single use mixing bag in order to physically remove viruses. A second UF/DF step is performed for buffer exchange into the 0.2 filtered pre-formulation buffer, 5 mM Citrate pH 6.0. The resulting product is then filtered through a 0.2 um filter. To achieve a final concentration of 6 mg/mL in the final formulation buffer, the product is mixed with calculated quantity of 5 mM Citrate, 15% Sucrose, 0.06% Polysorbate 80 pH 5.9, and 0.2 μm filtered. The resulting product is then filtered through a 0.2 um filter before being filled into sterile bags composed of a Polyolefin monolayer film, frozen and stored −80±20° C.

In another specific embodiment of this invention, the method of production of a bulk drug substance consists of firstly passing the clarified harvest through a protein A chromatography, followed by the incubation of the PA eluate at high pH (target pH=11) for an incubation time of 60 min at room temperature. Next the viral inactivated solution is neutralized to pH 5.5 and 0.2 μm filtered. Then the neutralized intermediate PA eluate is loaded onto a cation exchange chromatography column and the product is passed through a 0.2 μm filter. The antibody is then concentrated to a target of 25 mg/mL and dialyzed with a 50 mM Histidine pH 6.5 by an ultrafiltration/diafiltration (UF/DF) system. The product is then 0.2 μm filtered and purified on a positively-charged NatriFlo single-use membrane for anion exchange (AEX) chromatography in flow-through mode. The eluate is subsequently 0.2 μm filtered. Next, the product is nanofiltered through a Virosart® HF connected aseptically to a single use mixing bag in order to physically remove viruses. A second UF/DF step is performed for buffer exchange into the 0.2 um filtered pre-formulation buffer, 5 mM Histidine, 150 mM Arginine Monohydrochloride, pH 6.0. To achieve a final concentration of 6 mg/mL in the final formulation buffer, the product is mixed with calculated quantity of 5 mM L-Histidine, 150 mM L-Arginine Monohydrochloride, 15% Sucrose, 0.06% Polysorbate 80, pH 6.0. The resulting product is then filtered through a 0.2 um filter before being filled into sterile bags composed of a Polyolefin monolayer film, frozen and stored −80±20° C.

In certain embodiments of the present invention, a liquid pharmaceutical formulation comprising a monoclonal antibody, a buffer, a surfactant, and a stabilizing agent is disclosed As used herein, a "liquid" formulation is one that has been prepared in a liquid format. Such a formulation may be suitable for direct administration to a subject or, alternatively, can be packaged for storage either in a liquid form, in a frozen state or in a dried form (e.g. lyophilized) for later reconstitution into a liquid form or other forms suitable for administration to a subject.

The term "buffer" as used herein refers to a buffered solution that resists changes in pH by the action of its acid-base conjugate components. A buffer of this invention has a pH in the range from about 5.0 to about 7.0; and preferably is 6.0±0.5. Examples of buffers that can control the pH in this range include acetate (e.g. sodium acetate), succinate (such as sodium succinate), gluconate, histidine (e.g. L-Histidine), citrate, phosphate and other organic acid buffers.

Examples of a typical surfactant include: non-ionic surfactants (HLB 6 to 18) such as sorbitan fatty acid esters (e.g. sorbitan monocaprylate, sorbitan monolaurate, sorbitan monopalmitate), glycerine fatty acid esters (e.g. glycerine monocaprylate, glycerine monomyristate, glycerine monostearate), poly glycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxy ethylene polyoxypropylene alkyl ethers (e.g. polyoxyethylene polyoxypropylene glycol ether, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearyl amide); anionic surfactants such as Cio-Cis alkyl sulfates salts (e.g. sodium cetyl sulfate, sodium lauryl sulfate, sodium oleyl sulfate), polyoxyethylene Cio-Cis alkyl ether sulfates salts with an average of 2-4 moles of ethylene oxide (e.g. sodium polyoxyethylene lauryl sulfate), and Cs-Cis alkyl sulfosuccmate ester salts (e.g. sodium lauryl sulfosuccmate ester); and natural surfactants such as lecithin, glycerophospho lipid, sphingophospho lipids (e.g. sphingomyelin) and sucrose esters of C 12-C 18 fatty acids. Preferably, the surfactant is selected from polyoxyethylene sorbitan fatty acid esters. Particularly preferably the surfactant is Polysorbate 20, 21, 40, 60, 65, 80, 81 and 85, most preferably Polysorbate 80.

A stabilizing agent may be added to the formulation to stabilize the protein. Said stabilizing is selected from the group comprising sodium acetate, sodium bicarbonate, sodium carbonate, sodium chloride, potassium acetate, potassium bicarbonate, potassium carbonate, potassium chloride, sucrose, polyols, sugars, amino acids such as histidine, arginine, L-arginine hydrochloride, L-arginine monohydrochloride, glycine, methionine, proline, lysine, glutamic acid, amines and trehalose.

In a particular embodiment of the present invention, the disclosed liquid pharmaceutical formulation comprising a monoclonal antibody, a buffer, a surfactant, and a stabilizing agent, wherein said monoclonal antibody is present in said pharmaceutical formulation at a concentration equal to or greater than about 0.01 mg/mL and equal to or less than about 100 mg/mL, preferably at a concentration of about 6 mg/mL, said buffer is Citrate present in said pharmaceutical formulation at concentration of about 5 mM, said surfactant is Polysorbate present in said pharmaceutical formulation at a percentage of about 0.06%, and said stabilizing agent is Sucrose present in said pharmaceutical formulation at a percentage of about 15%, and wherein said pharmaceutical formulation has a pH of about 5.9.

In another embodiment of the present invention, the disclosed liquid pharmaceutical formulation comprising a monoclonal antibody, a buffer, a surfactant, and stabilizing agents, wherein said monoclonal antibody is present in said pharmaceutical formulation at a concentration equal to or greater than about 0.01 mg/mL and equal to or less than about 100 mg/mL, preferably at a concentration of about 6 mg/mL, said buffer is L-Histidine, present in said pharmaceutical formulation at concentration of about 5 mM, said surfactant is Polysorbate present in said pharmaceutical formulation at a percentage of about 0.06%, and said stabilizing agents are Sucrose present in said pharmaceutical formulation at a percentage of about 15% and L-Arginine Monohydrochloride present in said pharmaceutical formulation at a concentration of about 120 mM and wherein said pharmaceutical formulation has a pH of about 6.0.

Viral inactivation assays are necessary to test the purity of the antibody solution and assure viral safety. In a preferred embodiment of this invention the antibody-containing solution is spiked with a model virus and the viral presence in the samples is measured before and after spiking. Model viruses include but are not limited to murine leukemia virus (MLV), Murine Minute Virus (MMV), Pseudorabies Virus (PRV).

The present invention propose methods of viral inactivation that can be used as alternative of the classically adopted low pH treatment. These alternatives are particularly advantageous when the therapeutic antibody to purify is low pH-liable and/or low pH is not compatible with the purification process.

FIG. 1: Viral inactivation by low pH, run 1, % of monomer HPLC-SE

Figure 2:
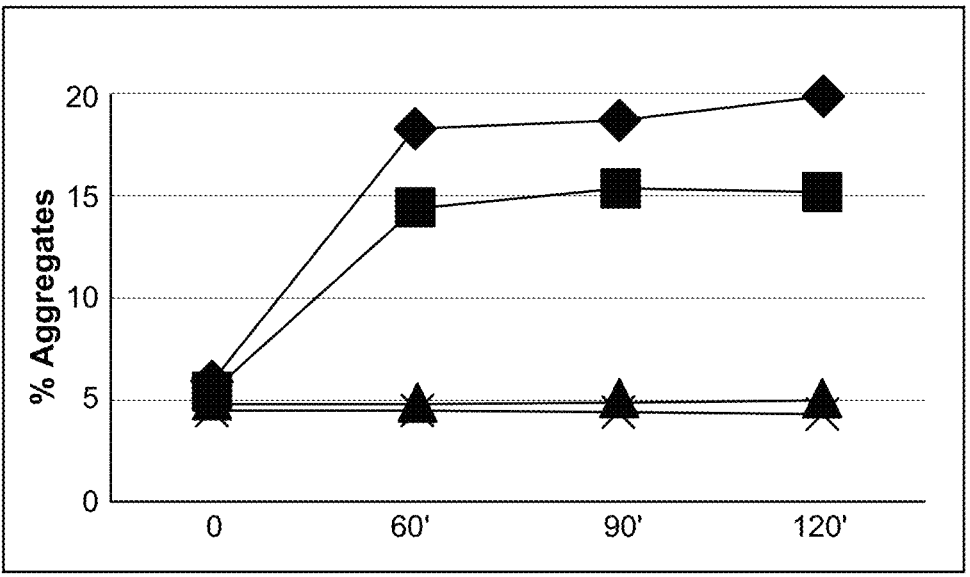
Figure 2:
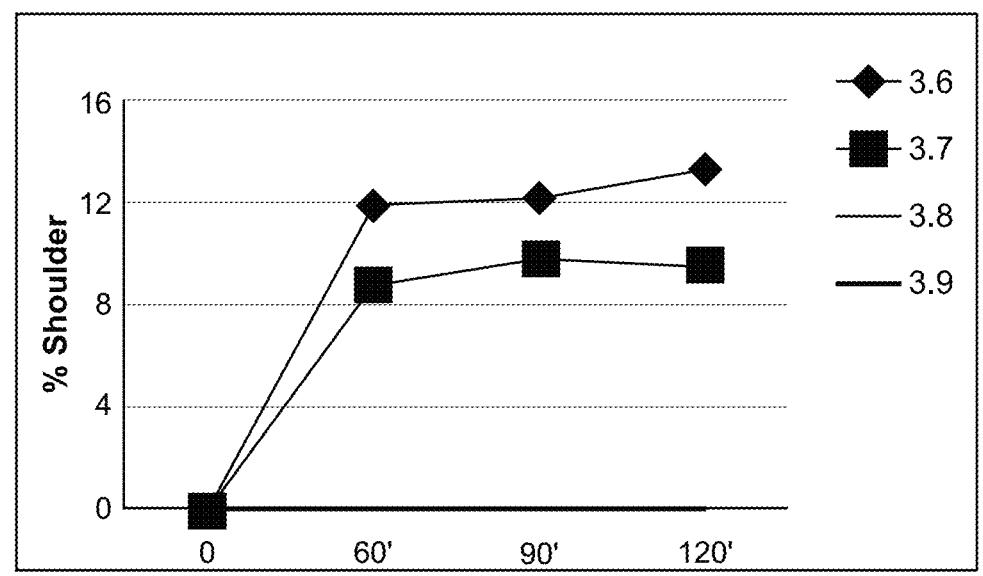
Figure 5:
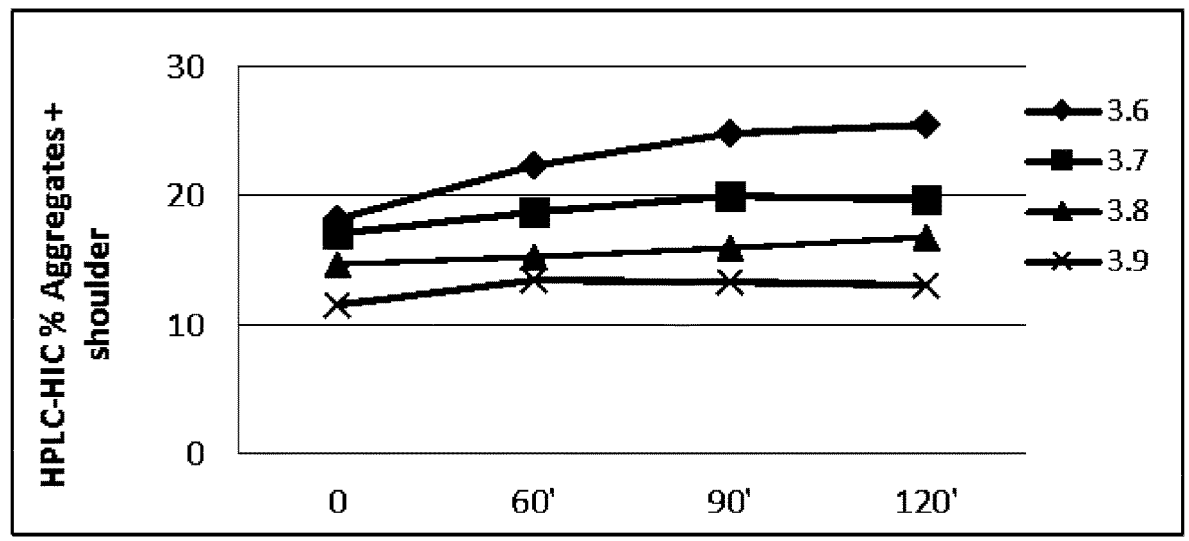
Figure 6:
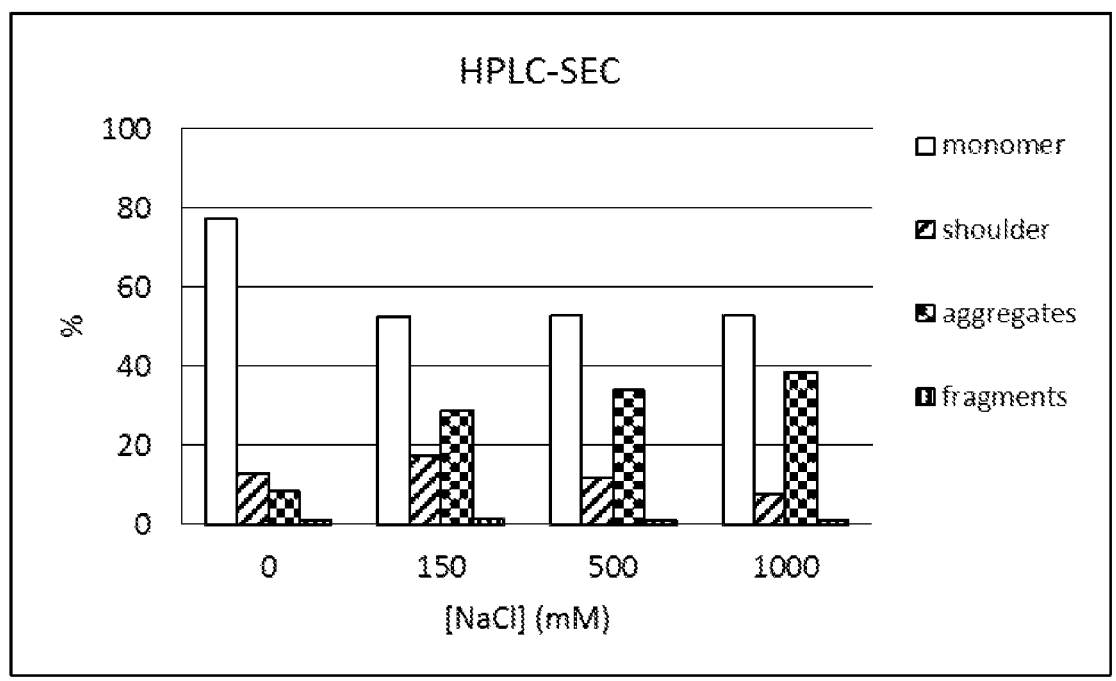
Figure 8:
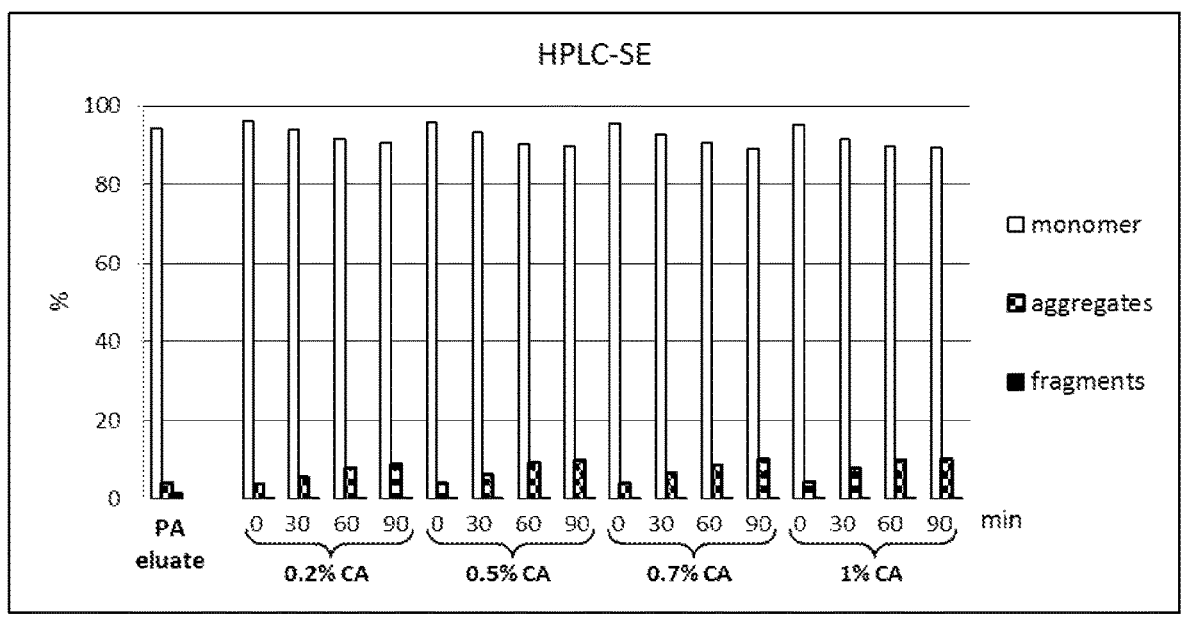
Figure 9:
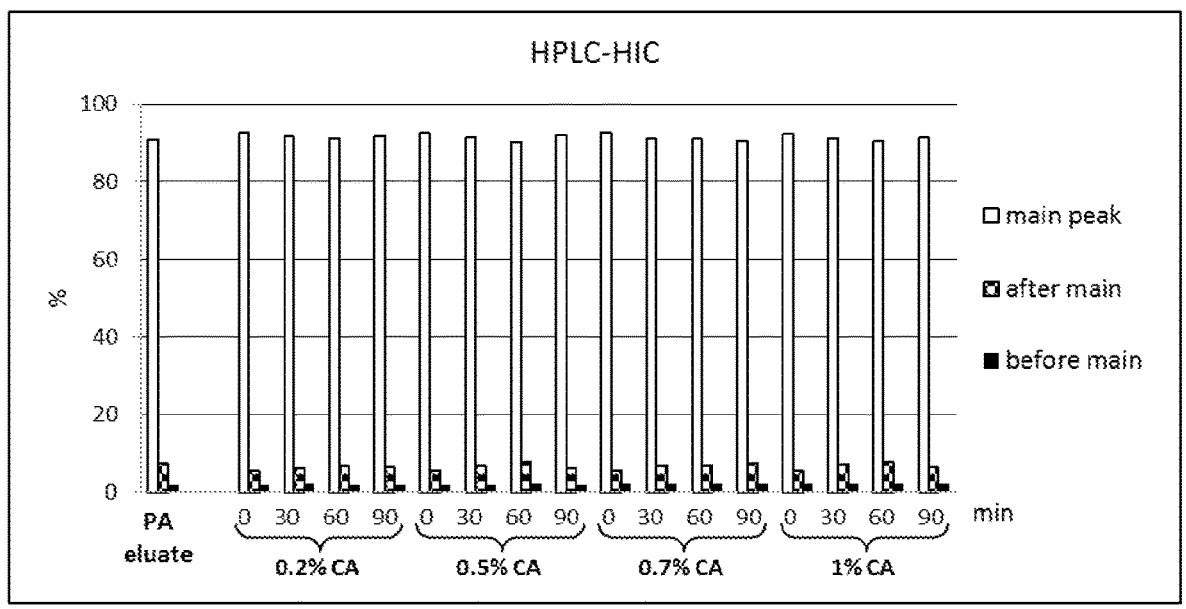
Figure 18:
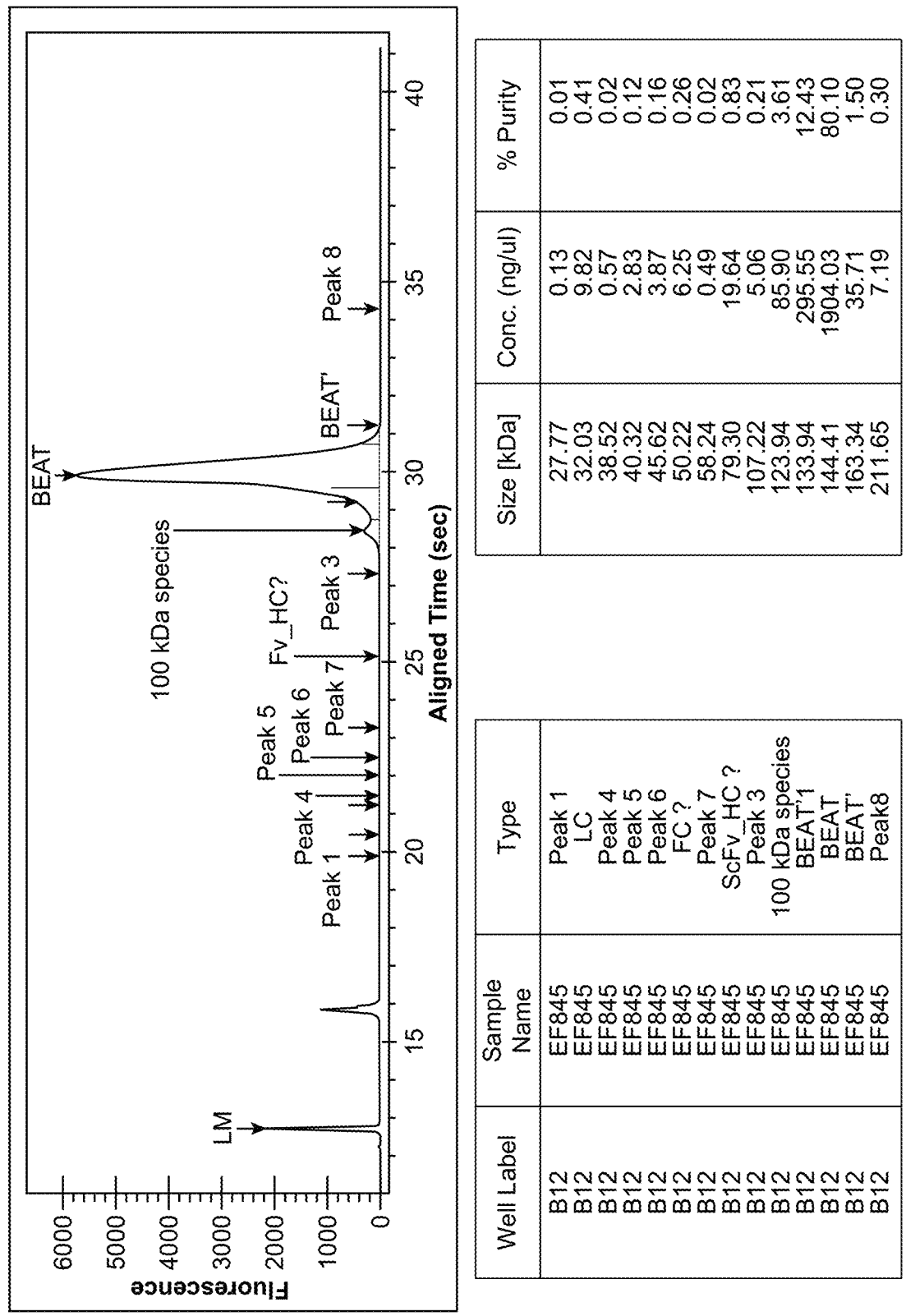
Figure 19:
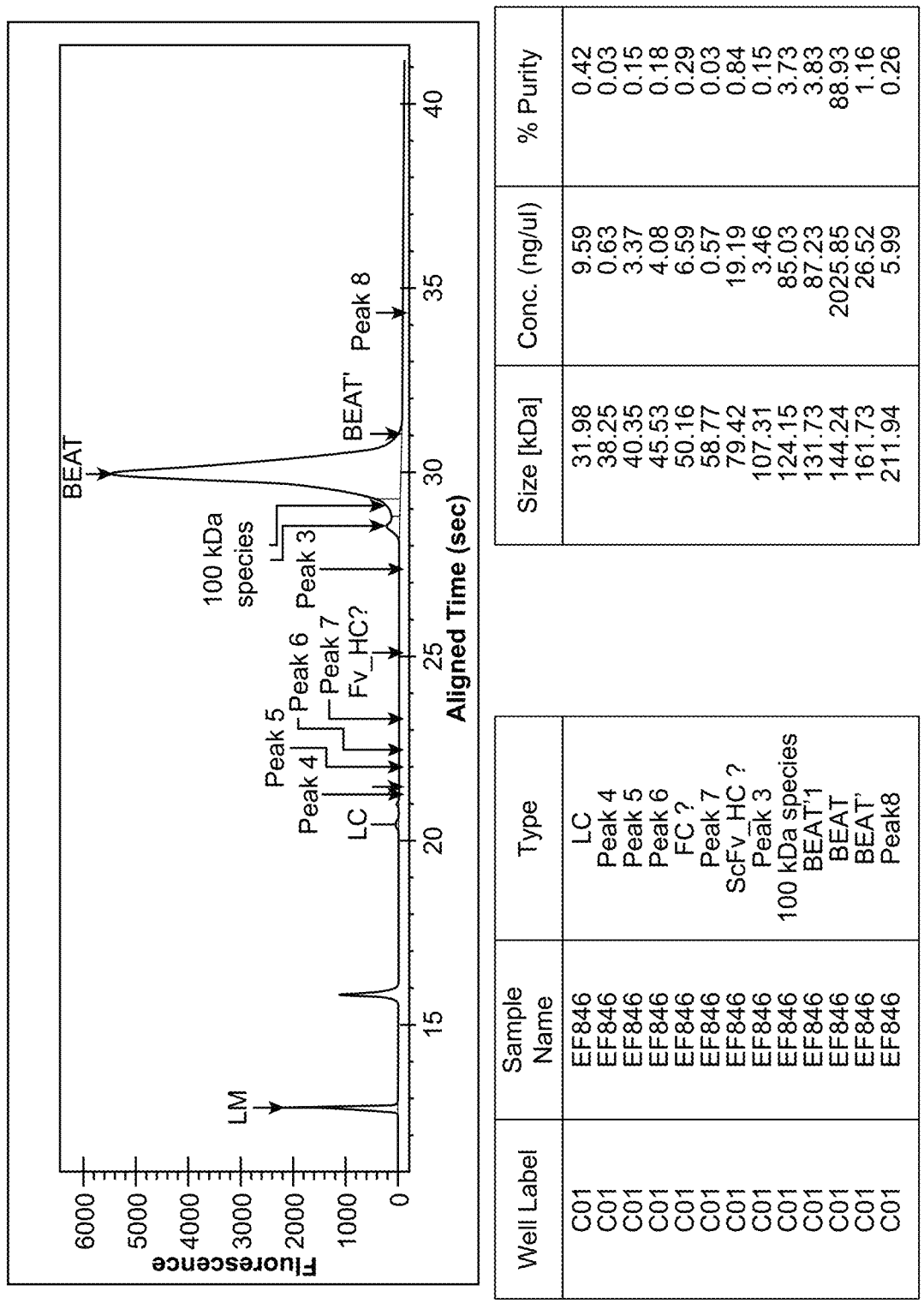
Figure 20:
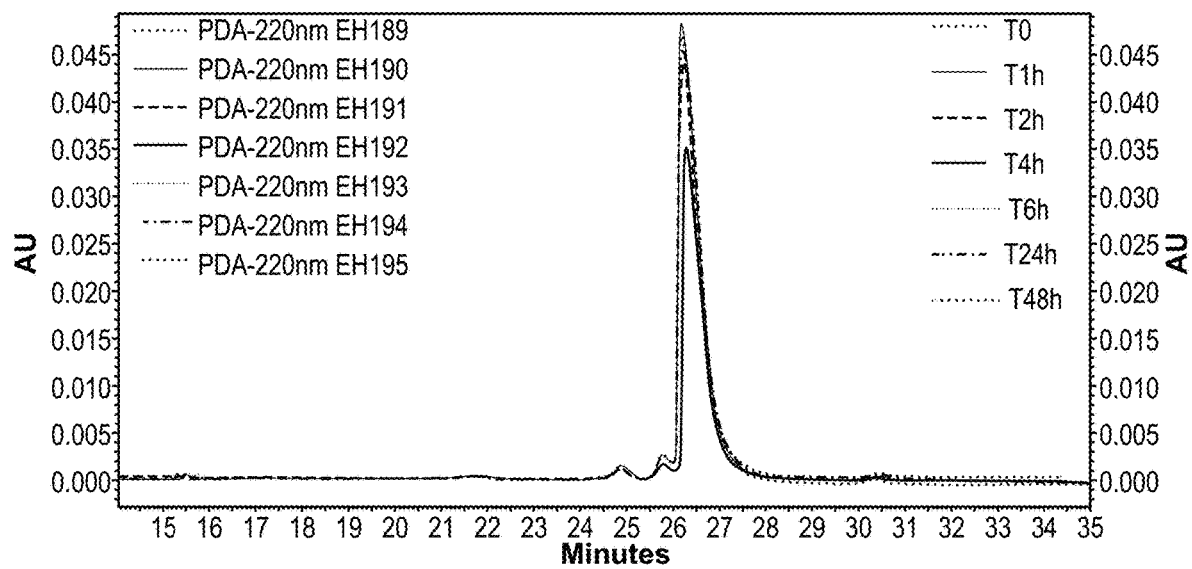
Figure 22:
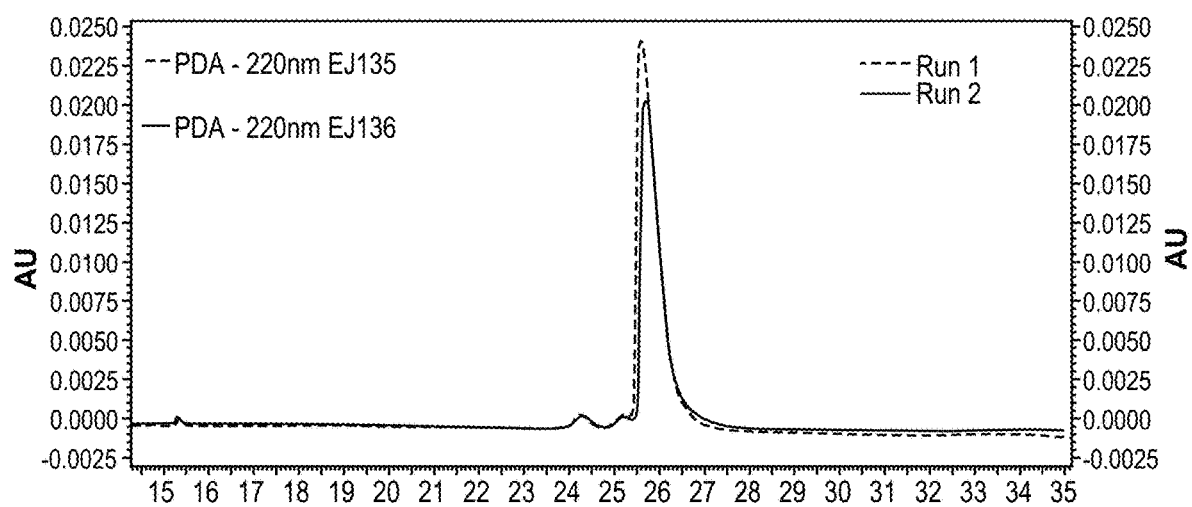
Figure 23:
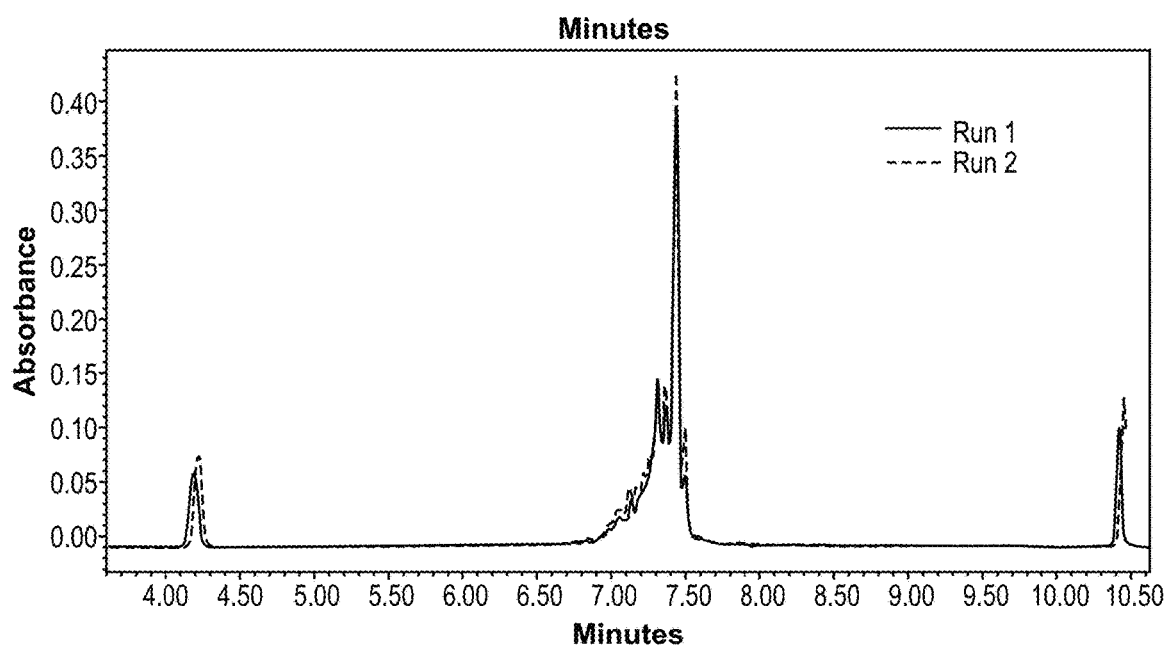

FIG. 2: Viral inactivation by low pH, run 1; (A) aggregates and (B) shoulder by HPLC-SE FIG. 3: HPLC-SE profile of degraded sample post low pH treatment FIG. 4: HPLC-HIC results post low pH treatment, % main peak FIG. 5: HPLC-HIC results post low pH treatment, % aggregates+shoulder FIG. 6: Viral inactivation at low pH+NaCl spike: HPLC-SE results FIG. 7: Viral inactivation at low pH+NaCl spike: CGE results FIG. 8: Caprylic acid incubation: HPLC-SE results FIG. 9: Caprylic acid incubation: HPLC-HIC results FIG. 10: BEAT®2 High pH hold time impact—SE-HPLC FIG. 11: BEAT®2 High pH hold time impact—NR CGE FIG. 12: BEAT®2 High pH hold time impact—Reduced CGE FIG. 13: BEAT®2 High pH hold time impact—ICE FIG. 14: Dose response curve and EC50 values FIG. 15: Monomer % by HPLC-SE after low pH incubation FIG. 16: Shoulder species and Aggregates % by HPLC-SE after low pH incubation FIG. 17: HPLC-SE profile of degraded sample post low pH incubation FIG. 18: Caliper CGE non-reduced profile of sample t0 post low pH incubation FIG. 19: Caliper CGE non-reduced profile of sample T48h post low pH incubation FIG. 20: Comparison of CGE non-reduced profiles for different high pH incubation times FIG. 21: Comparison of ICE profiles for different high pH incubation times FIG. 22: Comparison of CGE non-reduced profiles for VI high pH runs at pilot scale FIG. 23: Comparison of ICE profiles for VI high pH runs at pilot scale FIG. 24: Dose response curve and EC50 according to high pH treatment durations FIG. 25: High pH treatment kinetics FIG. 26: Ab1 High pH hold time impact—SE-HPLC FIG. 27: Ab1 High pH hold time impact—NR CGE FIG. 28: Ab1 High pH hold time impact—Reduced CGE FIG. 29: Ab1 High pH hold time impact—ICE FIG. 30: Dose response curve and EC50 values EXAMPLE 1: LOW pH TREATMENT, COMMONLY USED AS VIRAL INACTIVATION STEP IN THE PURIFICATION PROCESS OF THERAPEUTIC PROTEINS, IMPAIRS THE STABILITY OF LOW pH-LIABLE ANTIBODIES The technique commonly used to inactivate viruses in the process of therapeutic protein purification consists of incubating the protein-containing solution at low pH. Here, the capacity of low pH treatment to inactivate viruses and its effect on the stability of monoclonal hetero-dimeric antibodies was investigated. The results of this investigation suggests that low pH conditions, at which viral inactivation is effective and antibody stability is generally preserved, like in the case of BEAT®1 antibody, are not appropriate for low pH-liable antibodies, such as BEAT® 2. To overcome this problem, additional studies have been carried out to test the effect of alternative methods of viral inactivation on the stability and activity of BEAT® 2. This example illustrates (a) viral removal validation (VRV) studies on low pH treatment of BEAT® 1-containing protein A (PA) chromatography eluate; (b) the impact of effective low pH levels on BEAT®2 stability; studies on (c) BEAT®2 stability and (d) activity carried out when alternative viral inactivation techniques are used.

a. VRV Studies on Low pH Treatment of PA Eluate Containing BEAT®1 Molecules

Firstly, the efficacy of viral inactivation by the incubation of BEAT®1-containing PA eluate at low pH was investigated as step of the purification process of BEAT®1 antibodies.

Materials, Methods and Equipment

The model virus used for this VRV study was Murine Leukemia Virus (MLV), a relevant model of endogenous virus. The main characteristics of this viral model are given in Table 1.

TABLE 1

Properties of MLV model virus

| Virus | Family | Structure, Genome | Size (nm) | Physico-chemical resistance |
|---|---|---|---|---|
| MLV | Retro viridae | Enveloped, ssRNA | 80-110 | Low |

Low pH treatment was applied on PA eluate containing BEAT®1 molecules. Starting materials used during the VRV studies conducted on BEAT®1 purification process are shown in Table 2.

TABLE 2

Intermediate load material

| Study | Description | Concentration (g/L) |
|---|---|---|
| Low pH inactivation | PA eluate | 5.8 |

For the VRV study, test samples were taken before low pH treatment and analyzed for viral titer. The sample was spiked with a known quantity of stock virus; the output viral titre was compared with the respective load viral titre to calculate the reduction factor. This was performed under "worst case" conditions as shown in Table 3.

TABLE 3

"Worst case" conditions

| Virus Reducing Process Step | Worst case | Temperature |
|---|---|---|
| Low pH inactivation | 16° C., pH setpoint + 0.2 | 16 ± 1° C. |

This step was performed in duplicate with 3 different pH conditions (set point, +0.2 and −0.2), as shown in Table 4. The temperature (T) specification for the low pH inactivation step is 20° C.-25° C. However, the temperature targeted during the run was 16° C. to have worst case scenario data:

TABLE 4

Summary of pH and temperature conditions for low pH viral inactivation

| pH Conditions | Temperature |
|---|---|
| 3.5 ± 0.1 (targeting pH 3.5) | 16 ± 1° C. (targeting 16° C.) |
| 3.7 ± 0.1 (targeting pH 3.7) | 16 ± 1° C. (targeting 16° C.) |
| 3.9 ± 0.1 (targeting pH 3.9) | 16 ± 1° C. (targeting 16° C.) |

Log reduction factors is calculated with respect to the Neutralized Load (L) sample; samples are drawn after different incubation time (t) points, 5, 10, 30, and 60 minutes and subsequently neutralized at pH 6.0-8.0 using 0.25 M Histidine pH 12.0, to have kinetics of the different low pH treatment. Samples are then placed on ice immediately prior to titration. The Load Hold (H) sample is held at 16° C.±1° C. for the duration of the process and collected with the t=60 min sample. In addition to the standard titration, large volume plating (LVP) has been performed for t=60 min sample. A summary of the assays performed during the low pH inactivation step is shown in Table 5:

TABLE 5

Summary of the assays performed during spiking study for low pH viral inactivation

| Virus | Standard Titration | LVP |
|---|---|---|
| MLV | L, H, t = 5 min, t = 10 min, t = 30 min, t = 60 min | t = 60 min |

Results and Conclusions

If no statistically significant variation were observed in virus titre (note: less than 1 $\log_{10}$ difference is deemed non-significant) between the Load sample and the Load Hold sample, this was the load sample used to calculate the reduction factors or the load 2 sample where there has been an additional filtration performed (only for VRF step). No significant variation in virus titre was observed between the Load and the Load Hold results whatever the step (except for VRF where an additional filtration was performed) and hence, the load result was used to do the $\log_{10}$ reduction factor.

The low pH viral inactivation step BEAT®1 was evaluated for its efficiency on MLV clearance at pH 3.5, pH 3.7, and pH 3.9 using PA eluate. Table 6 shows the $\log_{10}$ values obtained for the different low pH levels and the $\log_{10}$ reduction factor calculated for each run.

TABLE 6

$\log_{10}$ virus reduction value for MLV for low pH inactivation (standard assay)

| | $\log_{10}$ total virus | | | | | |
|---|---|---|---|---|---|---|
| | pH 3.5 | | pH 3.7 | | pH 3.9 | |
| Sample | Run 1 | Run 2 | Run 1 | Run 2 | Run 1 | Run 2 |
| Actual pH | 3.50 | 3.47 | 3.69 | 3.70 | 3.86 | 3.85 |
| Load | 6.02 | 6.37 | 6.37 | 6.02 | 6.54 | 6.54 |
| 5 min | 3.57 | 1.73 | 5.23 | 5.49 | 5.58 | 5.67 |
| 10 min | 2.40 | 1.73 | 4.88 | 5.49 | 5.76 | 5.49 |
| 30 min | 1.28 | 1.73 | 4.62 | 5.23 | 5.49 | 5.58 |
| 60 min | 0.08 | 1.66 | 4.18 | 4.27 | 5.49 | 5.49 |
| $\log_{10}$ reduction factor | 5.94 | 4.71 | 2.19 | 1.75 | 1.05 | 1.05 |
| Load Hold | 6.28 | 6.02 | 6.37 | 6.19 | 6.37 | 6.37 |

Viral inactivation studies show that:

Low pH inactivation at pH 3.5 leads to reduction factors of 5.94 and 4.71 $\log_{10}$ for run 1 and run 2 respectively, which means that low pH inactivation was effective for MLV at pH 3.5. The results presented in Table 6 demonstrate however, that the variation between run 1 and 2 was significant with more than 1 $\log_{10}$ difference (0.08 $\log_{10}$ for run 1 and 1.66 $\log_{10}$ for run 2 respectively) and hence the results were not comparable between the repeat runs. The low pH inactivation at pH 3.5 was however performed only for providing data on the MLV inactivation behavior at pH 3.5 and hence, these results were not used for the overall log reduction factor calculation.

Low pH inactivation at pH 3.7 contributed to the inactivation of MLV viruses, as determined in standard assay (LVP performed for the t=60 min time point). Reduction factors of 2.19 and 1.75 $\log_{10}$ (run 1 and run 2, respectively) were obtained from low pH inactivation runs. The results presented in Table 6 demonstrate that the variation between run 1 and 2 was not significant with 4.18 $\log_{10}$ for run 1 and 4.27 $\log_{10}$ for run 2 and hence the results are comparable between the repeat runs.

Low pH inactivation at pH 3.9 contributed to the inactivation of MLV viruses, as determined in standard assay (LVP performed for the t=60 min time point). Reduction factors of 1.05 and 1.05 $\log_{10}$ (run 1 and run 2, respectively) were obtained from low pH inactivation runs. The results presented in Table 6 demonstrate that the variation between run 1 and 2 was not significant with 5.49 $\log_{10}$ for both runs 1 and 2 and hence the results are comparable between the repeated runs.

Based on the obtained results, low pH inactivation at pH 3.5 was shown to be effective in the inactivation of MLV viruses, with minimum reduction factor of 4.71 $\log_{10}$. Low pH inactivation at pH 3.7 was shown to contribute to the inactivation of MLV viruses, with minimum reduction factor of 1.75 $\log_{10}$. Low pH inactivation at pH 3.9 was shown to contribute to the inactivation of MLV viruses, with minimum reduction factor of 1.05 $\log_{10}$.

These results indicate that low pH treatment, classically used for the inactivation of virus in the process of production of monoclonal antibodies, can effectively inactivate MLV virus at pH 3.5.

b. Stability Study on BEAT®2 Subjected to Low pH

Next, studies on the stabilities of other antibodies were carried out to evaluate the effect of low pH treatment. Particularly, BEAT®2 was incubated at low pH.

Materials, Methods and Equipment

The starting material used in this study was PA eluate obtained from affinity chromatography using the KanCapA resin from Kaneka.

Cell cultures were typically terminated when viability was lower than 80% and cell debris were removed by dead-end depth filtration followed by a filtration on a 0.2 µm filter. The cell culture supernatants were from CHO cells.

Different starting materials were used for this study coming from non-representative bulk harvests (two clones, clone 1 and clone 2 coming from small scale bioreactor or wave bag cultures) and from a representative bulk harvest (selected clone 1, Single Use Bioreactor 250 L).

In-process 0.2 µm filtration steps were typically performed using TPP 250 mL filter-tops, Steriflip (Millipore) or Sartopore 2 filters (Sartorius). 0.2 µm filtration steps were performed for all buffers and all intermediates unless those intermediates were further processed immediately. Buffers were stored at room temperature and the process intermediates were typically stored at +5±3° C. For viral inactivation studies, only magnetic agitators and pH meter were used.

PA eluate used as starting material was coming from Protein A small scale chromatography development runs performed on ÄKTA Explorer and ÄKTA Purifier systems (GE Healthcare) using 1.1 cm diameter Vantage L columns (Millipore).

Harvest titers were determined using PA-HPLC. PA eluates were analyzed by HPLC-SE to estimate the percentage of aggregates and fragments. However, SE-HPLC was not sufficient to assess the remaining percentage of homodimer impurities. Therefore PA eluate samples were also analyzed by CGE non-reduced in routine. For some runs using PA eluate as starting material, the yield of the viral inactivation step was calculated measuring the concentrations before and after treatment with a Nanodrop equipment (Nanodrop 2000 spectrophotometer, Thermo Scientific) at 280 nm. The molar extinction coefficient of the BEAT®2 is 1.52. The HPLC-HIC and iCE3 were used to analyze some experiments, to look if there was any effect of the treatment on the hydrophobic species and for the charge variants.

Results and Conclusions

Small volumes of PA eluates (around 3 mL) from clone 1 and clone 2 cell culture were acidified to pH 3.6, 3.7, 3.8 and 3.9 using HCl 3.7%. BEAT®2 was incubated at low pH for 60 to 120 minutes at room temperature (RT) under agitation. To stop the reaction, the pH was increased to pH 6.0 or 5.5 using 250 mM Histidine pH 12.0. This experiment was repeated several times to confirm the results. To observe if the salt had a protector effect on the molecule, the same study was performed by first spiking PA eluate with NaCl before incubation at low pH. Different concentrations of NaCl were tested: 150 mM, 500 mM and 1 M combined with acidification at pH 3.7 for 90 minutes. The product was then analyzed by HPLC-SE, HPLC-HIC and by CGE (non-reduced). In Table 7 is shown the summary of the conditions tested on low pH incubation.

TABLE 7

Low pH incubation conditions

| pH target | 3.6-3.7-3.8-3.9 |
|---|---|
| Incubation time (min) | 0-60-90-120 |
| NaCl spike (mM) | 0-150-500-1000 |

PA Eluate without NaCl

Figure 3:
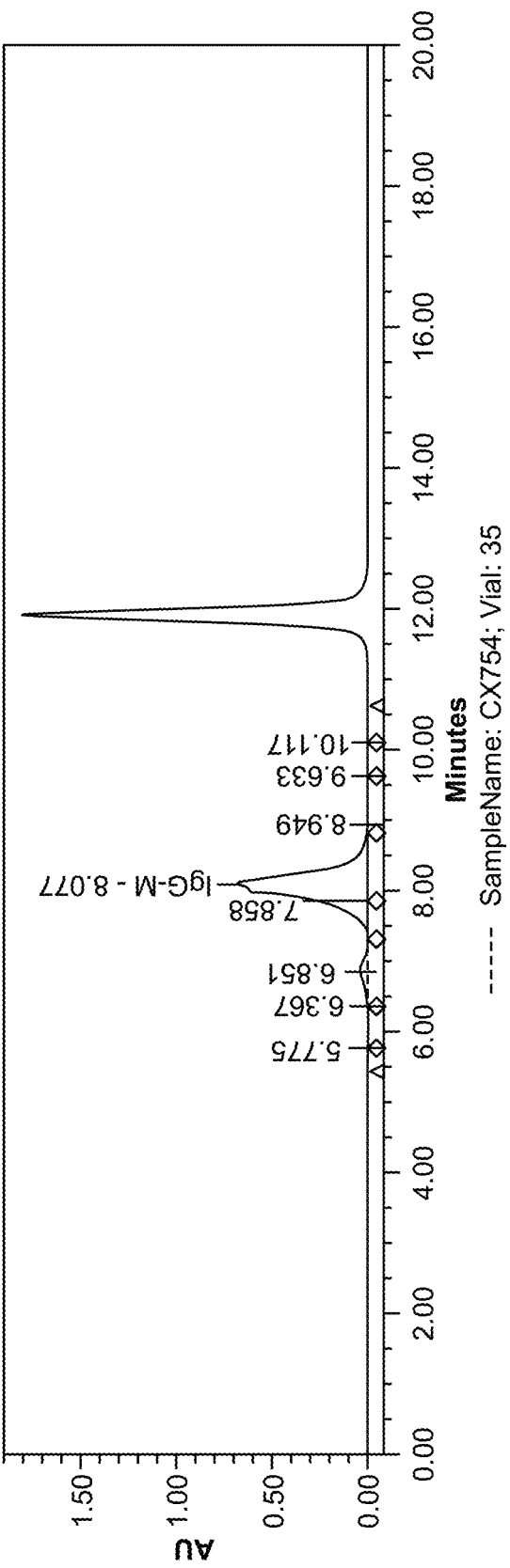

Only the results obtained with clone 1 are shown since the experiments performed with clone 2 gave similar results. Four repeated low pH experiments were performed on PA eluate, the results were similar and comparable for all of them. The percentage of monomer by HPLC-SE at different pH for different time points is illustrated in FIG. 1. As shown in the graph, the most acidic condition at pH 3.6 leads to a significant decrease of monomer percentage, which drops from 95% to 80% after 60 minutes of incubation. The treatment at pH 3.7 had also a negative effect on the stability of the BEAT® 2. Only the less acidic conditions at pH 3.8 and 3.9 had no negative effect on the antibody. FIG. 2 shows the increase of other species during the degradation of the monomer, the aggregates and the "shoulder" species. The shoulder specie was appearing in front the main peak of monomer. In FIG. 3 is shown an example of the profile by HPLC-SE containing an important amount (13%) of "shoulder" specie. CGE (non-reduced) results of two different low pH treatment runs is listed below in Table 8, where neutralization was done to pH 6.0 or pH 5.5.

TABLE 8

HPLC-SE profile degraded sample post low pH treatment:

| | Run 2 Neutralization pH 6.0 | | | | | Run 4 Neutralization pH 5.5 | | | | |
|---|---|---|---|---|---|---|---|---|---|---|
| | pH 3.6 t0 | pH 3.6 t120 | pH 3.7 t120 | pH 3.8 t120 | pH 3.9 t120 | pH 3.6 t0 | pH 3.6 t120 | pH 3.7 t120 | pH 3.8 t120 | pH 3.9 t120 |
| LC % | 0.7 | 0.6 | 0.6 | 0.6 | 0.7 | 0.5 | 0.6 | 0.5 | 0.6 | 0.5 |
| Unknown % | 0.1 | 0.1 | 0.1 | 0.1 | 0.1 | 0.1 | 0.1 | 0.1 | 0.1 | 0.1 |
| HC % | 0.8 | 0.8 | 0.9 | 1 | 0.7 | 0.7 | 0.7 | 0.6 | 0.6 | 0.7 |
| Unknown % | 0.2 | 0.3 | 0.2 | 0 | 0 | 0.7 | 0.7 | 0.6 | 0.5 | 0.6 |
| Fragment 75 kDa % | 0 | 0 | 0 | 0 | 0 | 0 | 0.1 | 0.1 | 0.1 | 0.1 |
| Fragment 80 kDa % | 0.4 | 0.5 | 0.3 | 0.4 | 0.4 | 0.2 | 0.2 | 0.2 | 0.2 | 0.3 |
| Fragment 100 kDa % | 6.7 | 6.9 | 6.6 | 6.4 | 6.4 | 5.6 | 5.7 | 5.7 | 5.5 | 5.6 |
| BEAT' % | 3.5 | 3.7 | 3.1 | 3.3 | 3.3 | 3.8 | 3.6 | 3.6 | 3.6 | 3.6 |
| BEAT % | 83 | 80.8 | 82.7 | 82.2 | 83.7 | 84 | 84.5 | 84.4 | 84.6 | 84.7 |
| Total BEAT % | 86.5 | 84.5 | 85.8 | 85.5 | 87 | 87.8 | 88.1 | 88.0 | 88.2 | 88.3 |
| BEAT" % | 4.2 | 5.6 | 4.4 | 4.8 | 4.2 | 3.2 | 3.2 | 3.8 | 3.8 | 3.3 |
| IgG % | 0.4 | 0.7 | 1 | 1.3 | 0.5 | 0.3 | 0.3 | 0.3 | 0.4 | 0.5 |
| Aggregates % | 0.2 | 0 | 0.1 | 0 | 0 | 0.3 | 0.3 | 0 | 0 | 0 |

Figure 4:
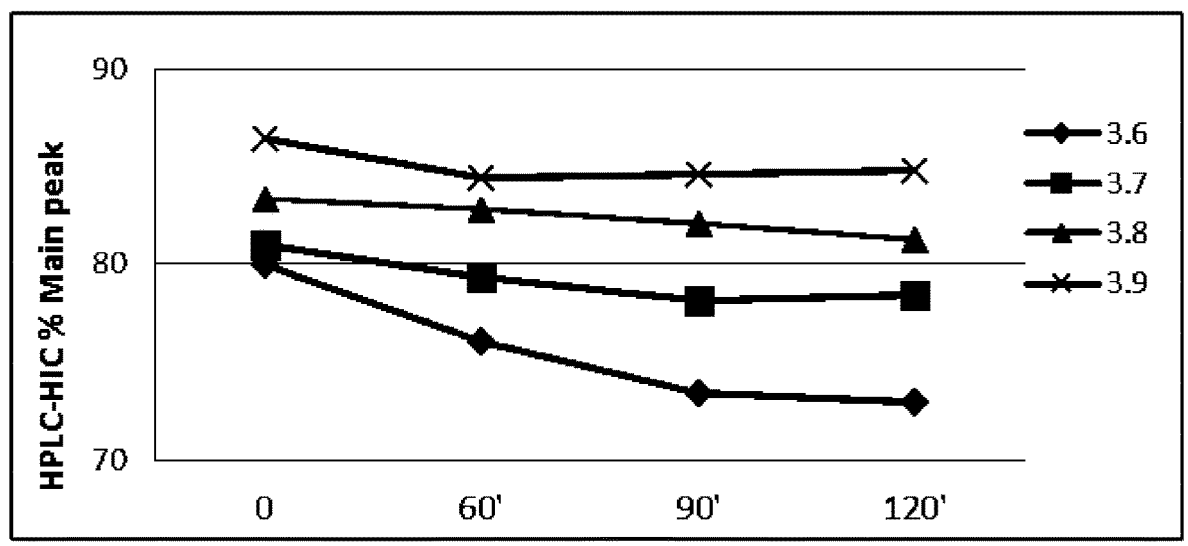

CGE data show that pH and time of incubation do not effect on the amount of BEAT®2 as the percentage of fragments and others species were similar for all conditions. Neutralization at pH 5.5 was better compared to neutralization at pH 6.0 as the BEAT®2 was 1% inferior. Degradation was observed by HPLC-HIC, as shown in FIG. 4 and in FIG. 5 the main peak percentage was decreased at more acidic pH over the time with an increasing of the aggregates species. These results show that BEAT®2 is stable only for the condition at pH 3.9; nevertheless previous experiments on BEAT®1 showed that this pH is not acidic enough to have an effective viral inactivation action.

PA Eluate with NaCl

Figure 7:
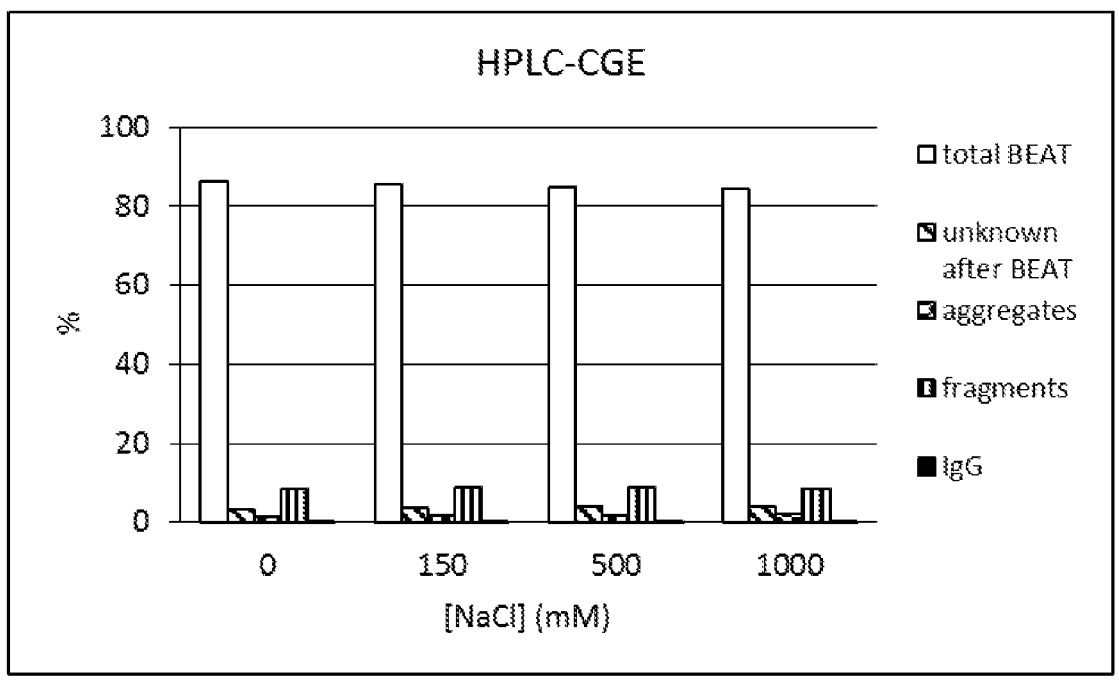

Salt was used to increase the stability of the proteins, one experiment was done with different concentrations of NaCl before treatment at low pH to see if BEAT®2 stability under low pH treatment was improved. Different concentrations were tested, from 0.15 M to 1 M NaCl before the acidification at pH 3.7 for 90 minutes, HPLC-SE and CGE non-reduced are showed in FIG. 6 and FIG. 7, respectively. The results show that BEAT®2 is not stable at low pH even when spiked with NaCl. By HPLC-HIC, not listed, degradation was observed, the main peak decreased from 82% to 60% after 90 minutes of incubation for all the salt conditions. In FIG. 7, no variation was observed by CGE.

The results of these experiments indicate that low pH treatment is not a suitable viral inactivation step for the process of BEAT®2 antibody purification.

c. Testing the Stability of BEAT®2 when Subjected to Alternative Viral Inactivation Treatments Given that low pH treatment impairs the stability of BEAT®2, other methods of viral inactivation were tested and their effect on the stability of the antibody was investigated. The tested treatments include: pasteurization treatment of PA eluate, caprylic acid (CA) treatment of PA eluate, Arginine treatment of PA eluate, solvent and detergent (S/D) treatment of PA eluate, S/D treatment of clarified harvest and high pH treatment of PA eluate.

Materials, Methods and Equipment

Materials, methods and equipment used for the following BEAT®2 stability are the same described in "b. Stability study on BEAT®2 subjected to low pH". Additionally, heating block was used for pasteurization.

Results and Conclusions

Pasteurization Treatment of PA Eluate

Pasteurization, commonly used in commercial processes for viral inactivation, was tested as alternative to low pH treatment. PA eluate from clone 1 and from clone 2 were used to test the effect of pasteurization on BEAT®2 antibody stability. PA eluates were neutralized to pH 6.0 using 250 mM Histidine pH 12.0. Different conditions of incubation were tested, including incubation at room temperature (RT) and at 60° C. for 30 and 60 minutes using a water bath. After the experiment, the product was analyzed by HPLC-SE, HPLC-HIC and by CGE (non-reduced).

Precipitation was observed for all conditions. In Table 9, the summary of the results after the treatment are presented.

TABLE 9

HPLC-SE, HPLC-HIC and CGE post pasteurization

| | | Clone 1 | | |
|---|---|---|---|---|
| | | RT | T60° C., 30 min | T60° C., 60 min |
| HPLC-SE | Aggregates % | 4.53 | 39.52 | 54.04 |
| | Monomer % | 94.55 | 43.39 | 13.16 |
| | Fragments % | 0.9 | 17.09 | 32.8 |
| HPLC-HIC | before main % | 2.2 | 16.1 | 12.9 |
| | Main peak % | 88.1 | 13.3 | 4.9 |
| | after peak % | 9.7 | 70.6 | 82.2 |
| CGE non-reduced | Unknown % | 0.0 | 0.0 | 0.5 |
| | LC % | 0.7 | 0.6 | 0.7 |
| | unknown % | 0.1 | 0.1 | 0.1 |
| | HC % | 0.6 | 0.5 | 0.7 |
| | unknown % | 0.1 | 0.1 | 0.2 |
| | Fragment 75 kDa % | 0.1 | 0.1 | 0.1 |
| | Fragment 80 kDa % | 0.4 | 0.3 | 0.3 |
| | Fragment 100 kDa % | 6.6 | 6.3 | 10.3 |
| | BEAT' % | 3.2 | 3.1 | 3.5 |
| | BEAT % | 81.0 | 86.0 | 77.5 |

TABLE 9-continued

HPLC-SE, HPLC-HIC and CGE post pasteurization

| | | Clone 1 | | |
|---|---|---|---|---|
| | | RT | T60° C., 30 min | T60° C., 60 min |
| | BEAT" % | 6.2 | 2.5 | 2.8 |
| | IgG % | 1.0 | 0.5 | 0.4 |
| | Aggregates % | 0.0 | 0.0 | 2.9 |

HPLC-SE and HPLC-HIC results show that BEAT®2 is not stable at high temperature with an important decrease of the main peak percentage for both analyses even after 30 minutes (from 94.6 to 43.4% in HPLC-SE and 88.1 to 13.3 in HIC-HPLC).

Based on these results, pasteurization was not selected for further investigations and developments.

Caprylic Acid Treatment of PA Eluate

Caprylic acid is a precipitation agent that can be used for viral inactivation for precipitating viral proteins. PA eluate from clone 1 was used to test the effect of the caprylic acid on the stability of BEAT®2 antibody. Several concentrations of caprylic acid were used to reach a final amount of 0.2%, 0.5%, 0.7% and 1%. PA eluate after elution (around pH 4.3) or neutralized at pH 5.5 (using 250 mM Histidine pH 12.0 buffer) was used as starting material. The incubation times applied were 30, 60 and 90 minutes. To stop the reaction, diatomaceous earth (DE) was used with a ratio of 0.5 g DE for 2 mL of PA eluate product. A 0.2 µm steriflip filter was used to purify the product through the DE. After the treatment, the product was analyzed by HPLC-SE, HPLC-HIC and by CGE (non-reduced). In Table 10 the summary of the conditions tested for caprylic acid treatment is given.

TABLE 10

| Caprylic acid treatment conditions | |
|---|---|
| Caprylic acid % | 0.2-0.5-0.7-1.0 |
| Incubation time (min) | 0-30-60-90 |
| Starting material pH | 4.3-5.5 |

The results at pH 5.5 are not illustrated because of the precipitation observed for above 0.2% of caprylic acid. The results of pH 4.3 are reported in FIG. 8, FIG. 9 and in Table 11. HPLC-SE results show a degradation over time comparing the t=0 to t=30, t=60 and t=90 minutes, with decrease of the monomer (about 6%) and increase of aggregates.

TABLE 11

Caprylic acid treatment: CGE results

| | PA eluate run 1 | PA eluate pH4.3 + CA 0.2% | | PA eluate pH4.3 + CA 0.5% | | PA eluate pH4.3 + CA 0.7% | | PA eluate pH4.3 + CA 1% | |
|---|---|---|---|---|---|---|---|---|---|
| Incubation time (min) | | 0 | 90 | 0 | 90 | 0 | 90 | 0 | 90 |
| LC % | 0.6 | 0.6 | 0.6 | 0.6 | 0.5 | 0.5 | 0.5 | 0.6 | 0.6 |
| Unknown after LC % | 0.1 | 0.1 | 0.1 | 0.1 | 0.1 | 0.1 | 0.1 | 0.1 | 0.1 |
| HC % | 0.8 | 0 | 0.7 | 0 | 0.9 | 0 | 1.0 | 0.1 | 1.0 |
| Unknown after HC % | 0.7 | 0 | 0.8 | 0 | 0.8 | 0 | 0.7 | 0.2 | 0.9 |
| Fragment 75 kDA % | 0.1 | 0 | 0 | 0 | 0.1 | 0 | 0.1 | 0 | 0.1 |
| Fragment 80 kDA % | 0.2 | 0.4 | 0.4 | 0.3 | 0.2 | 0.4 | 0.3 | 0.3 | 0.2 |
| Fragment 100 kDa % | 6.3 | 6.0 | 6.7 | 6.0 | 6.5 | 6.3 | 6.6 | 6.2 | 6.4 |
| BEAT' % | 4.2 | 3.4 | 4.4 | 3.4 | 4.7 | 3.4 | 4.2 | 3.6 | 4.7 |
| BEAT % | 82.2 | 84.0 | 80.3 | 84.4 | 80.7 | 84.6 | 81.4 | 84.6 | 81.7 |
| BEAT" % | 4.0 | 4.4 | 4.1 | 4.2 | 4.4 | 4.0 | 4.6 | 3.9 | 3.9 |
| IgG % | 0.8 | 1.2 | 1.9 | 1.1 | 1.1 | 0.5 | 0.6 | 0.5 | 0.6 |

No important degradation was noticed in CGE and HPLC-HIC. As per SE-HPLC results, BEAT®2 is not stable after 30 minutes even at lower acid caprylic concentration (0.2%). Nevertheless, considering the toxicity of caprylic acid and the need of the DE filtration to remove the reagent, this alternative was discarded and not selected as viral inactivation alternative.

Arginine Treatment of PA Eluate

The use of Arginine is known to effectively inactivate enveloped model virus. In this study, PA eluate from clone 1 was used as starting material. The pH of the PA eluate was adjusted to pH 4.0, pH 4.75, pH 4.79 and pH 5.5. Different amounts of Arginine (in 30 mM acetate) were added to target the final concentrations of 0.38 M, 0.4 M and 0.8 M of Arginine. The experiment was performed with different incubation times: no incubation time, 60 or 120 minutes (see Table 12). To stop the reaction, PD10 was used for a buffer exchange in PBS buffer.

TABLE 12

| Arginine treatment conditions | |
|---|---|
| pH target | 4.0-4.75-4.79-5.5 |
| Incubation time (min) | 0-60-120 |
| Arginine (M) | 0-0.4-0.8 |

In Table 13, the results of this experiments are presented.

TABLE 13

Arginine treatment results

|  |  | PA eluate pH4.3 | PA eluate pH4.0 | | | | PA eluate pH4.75 | PA eluate pH4.79 | PA eluate pH5.5 | | |
| --- | --- | --- | --- | --- | --- | --- | --- | --- | --- | --- | --- |
|  | Arginine concentration (M) | n/a | 0 | 0.4 | 0.8 | | 0.8 | 0.38 | 0 | 0.8 | |
|  | Incubation time (min) |  | 0 | 60 | 0 | 120 | 60 | 120 | 0 | 0 | 120 |
| HPLC-SEC | Aggregates % | 4.1 | 5.9 | 18.6 | 7.5 | 13.3 | 4.6 | 3.2 | 5.0 | 4.3 | 4.5 |
|  | Monomer % | 94.2 | 92.7 | 79.3 | 90.9 | 82.5 | 94.2 | 95.3 | 93.7 | 94.4 | 94.2 |
|  | Fragments % | 1.7 | 1.3 | 2.1 | 1.6 | 4.2 | 1.2 | 1.6 | 1.3 | 1.3 | 1.3 |
| HPLC-HIC | Before main % | 1.7 | 1.9 | 1.6 | 1.7 | 1.5 | 1.9 | 1.9 | 1.9 | 1.9 | 2.0 |
|  | Main peak % | 90.9 | 89.5 | 73.7 | 85.2 | 66.5 | 90.6 | 91.2 | 91.2 | 91.1 | 91.3 |
|  | After main % | 7.4 | 8.7 | 24.7 | 13.0 | 32.1 | 7.5 | 6.9 | 7.0 | 7.1 | 6.7 |
| CGE non reduced | LC % | 0.6 | n/a | | | | 0.6 | 0.6 | n/a | 0.9 | 0.6 |
|  | Unknown after LC % | 0.1 | | | | | 0.5 | 0.1 | | 0.6 | 0.1 |
|  | HC % | 0.8 | | | | | 0.7 | 0.6 | | 0.2 | 0.7 |
|  | Unknown after HC % | 0.7 | | | | | 0.6 | 0.5 | | 0.0 | 0.5 |
|  | Fragment 75 kDA % | 0.1 | | | | | 0.0 | 0.0 | | 0.2 | 0.1 |
|  | Fragment 80 kDA % | 0.2 | | | | | 0.7 | 0.4 | | 0.6 | 0.5 |
|  | Fragment 100 kDa % | 6.3 | | | | | 9.6 | 7.7 | | 16.1 | 6.5 |
|  | BEAT' % | 4.2 | | | | | 5.1 | 4.5 | | 1.5 | 4.4 |
|  | BEAT % | 82.2 | | | | | 77.2 | 80.4 | | 75.1 | 81.4 |
|  | BEAT" % | 4.0 | | | | | 3.8 | 4.4 | | 3.2 | 4.3 |
|  | IgG % | 0.8 | | | | | 0.3 | 0.8 | | 0.8 | 0.9 |
|  | Aggregates % | 0 | | | | | 0.9 | 0 | | 0 | 0 |

It was observed that the PA eluate at pH 4.0 was not stable when incubated with Arginine, indeed, there were 13% monomer losses by HPLC-SE only after 60 minutes of incubation using 0.4 M Arginine (92.7 to 79.3%) and 8% when incubated for 120 minutes with 0.8 M Arginine (90.9 to 82.5%). For the conditions superior or equal to pH 4.75, no degradation was observed even when using 0.8 M Arginine at pH 5.5 up to 120 minutes. Arginine treatment using pH higher or equal to 4.75 was considered as a potential alternative to low pH treatment.

Solvent Detergent Treatment of PA Eluate

Solvent and detergents can be used for viral inactivation because of their ability to dissolve lipid of the envelope of enveloped viruses.

PA eluate from clone 1 was used as starting material. First (study 1), TnBP treatment was tested at different concentrations: 0.1%, 0.3%, 0.5% and 1%. Next (study 2), the treatment with a combination of TnBP with Tween 80 and other detergents like Triton X-100 and Tween 20 was tested (the S/D mix was prepared and agitated 15 minutes prior to incubation with the product). The buffer exchange using PD10 was not efficient to remove the S/D, one dilution from 4 g/L to 0.3 g/L using PBS was used to try to stop the reaction. In Table 14 the summary of the 14 different conditions tested using the S/D on the PA eluate is reported.

TABLE 14

S/D treatment of PA eluate conditions

| Run | Solvent/detergent conditions |
| --- | --- |
| 1 | 0.1% TnBP |
| 2 | 0.3% TnBP |
| 3 | 0.5% TnBP |
| 4 | 1% TnBP |
| 5 | 0.3% TnBP + 1% Tween 80 |
| 6 | 0.3% TnBP + 0.2% Triton X-100 |
| 7 | 0.3% TnBP + 0.5% Triton X-100 |
| 8 | 0.3% TnBP + 1% Triton X-100 |
| 9 | 0.3% TnBP + 0.2% Tween 80 |
| 10 | 0.3% TnBP + 0.5% Tween 80 |
| 11 | 0.3% TnBP + 1% Tween 80 |
| 12 | 0.3% TnBP + 0.2% Tween 20 |
| 13 | 0.3% TnBP + 0.5% Tween 20 |
| 14 | 0.3% TnBP + 1% Tween 20 |

The results of the first part of the study (study 1) are reported in Table 15. In this experiment, at each time point, one PD-10 buffer exchange was performed.

TABLE 15

S/D treatment of PA eluate results, study 1

|  |  | PA eluate | 0.1% TnBP | | | | 0.3% TnBP | | | | 0.5% TnBP | | | |
| --- | --- | --- | --- | --- | --- | --- | --- | --- | --- | --- | --- | --- | --- | --- |
|  | Incubation time (min) | n/a | 0 | 60 | 90 | 120 | 0 | 60 | 90 | 120 | 0 | 60 | 90 | 120 |
| HPLC-SEC | Aggregates % | 4.1 | 4.5 | 5.6 | 5.6 | 5.7 | 5.5 | 5.5 | 5.5 | 5.6 | 5.3 | 5.2 | 5.3 | 5.3 |

TABLE 15-continued

S/D treatment of PA eluate results, study 1

|  |  |  |  |  |  |  |  |  |  |  |  |  |  |  |
|---|---|---|---|---|---|---|---|---|---|---|---|---|---|---|
|  | Monomer % | 94.2 | 88.5 | 93.2 | 93.2 | 93.1 | 93.3 | 93.3 | 93.3 | 93.2 | 93.4 | 93.6 | 93.6 | 93.6 |
|  | Fragments % | 1.7 | 7.0 | 1.2 | 1.2 | 1.2 | 1.2 | 1.2 | 1.2 | 1.1 | 1.3 | 1.2 | 1.1 | 1.1 |
| HPLC-HIC | Before main % | 1.7 | 4.6 | 2.1 | 2.1 | 2.0 | 2.1 | 2.2 | 2.0 | 1.9 | 2.5 | 2.2 | 2.0 | 1.9 |
|  | Main peak % | 90.9 | 90.1 | 91.6 | 91.5 | 91.5 | 91.5 | 91.6 | 91.4 | 91.5 | 91.4 | 91.5 | 91.7 | 91.7 |
|  | After main % | 7.4 | 5.3 | 6.3 | 6.5 | 6.6 | 6.4 | 6.3 | 6.6 | 6.5 | 6.0 | 6.4 | 6.3 | 6.4 |
| CGE Red | LC % | 0.6 | 0.6 | n/a | n/a | 0.5 | 0.6 | n/a | n/a | 0.5 | 0.5 | n/a | n/a | 0.5 |
|  | Unknown % | 0.1 | 2.1 |  |  | 0.1 | 0.1 |  |  | 0.1 | 0.3 |  |  | 0.1 |
|  | HC % | 0.8 | 0.2 |  |  | 0.3 | 0.3 |  |  | 0.3 | 0.3 |  |  | 0.4 |
|  | Unknown % | 0.7 | 0 |  |  | 0 | 0 |  |  | 0 | 0 |  |  | 0 |
|  | 75 kDA % | 0.1 | 0 |  |  | 0.1 | 0.1 |  |  | 0 | 0 |  |  | 0 |
|  | 80 kDA % | 0.2 | 0.4 |  |  | 0.6 | 0.5 |  |  | 0.4 | 0.9 |  |  | 0.4 |
|  | 100 kDa % | 6.3 | 13.8 |  |  | 5.5 | 5.8 |  |  | 5.8 | 6.6 |  |  | 5.9 |
|  | BEAT' % | 4.2 | 3.0 |  |  | 3.8 | 4.1 |  |  | 3.6 | 4.9 |  |  | 3.4 |
|  | BEAT % | 82.2 | 77.8 |  |  | 84.2 | 84.0 |  |  | 85.1 | 82.6 |  |  | 84.7 |
|  | BEAT" % | 4.0 | 2.0 |  |  | 3.5 | 3.9 |  |  | 3.6 | 3.4 |  |  | 3.3 |
|  | IgG % | 0.8 | 0.2 |  |  | 0.5 | 0.7 |  |  | 0.5 | 0.6 |  |  | 0.4 |
|  | Aggregate % | 0 | 0 |  |  | 0.9 | 0 |  |  | 0 | 0 |  |  | 0.9 |

|  |  |  | 1% TnBP [1] | | | 0.3% TnBP + 1% Tween 80 | | | |
|---|---|---|---|---|---|---|---|---|---|
|  |  | Incubation time (min) | 0 | 60 | 90 | 0 | 60 | 90 | 120 |
| HPLC-SEC | Aggregates % |  | 5.3 | 5.3 | 5.4 | 12.6 | 13.2 | 13.4 | 13.5 |
|  | Monomer % |  | 93.4 | 93.5 | 93.6 | 86.0 | 85.5 | 85.3 | 85.3 |
|  | Fragments % |  | 1.2 | 1.2 | 1.1 | 1.4 | 1.4 | 1.3 | 1.2 |
| HPLC-HIC | Before main % |  | 2.3 | 2.2 | 1.9 | 2.3 | 2.1 | 1.9 | 1.9 |
|  | Main peak % |  | 91.3 | 91.6 | 91.6 | 92.6 | 92.1 | 92.0 | 92.2 |
|  | After main % |  | 6.4 | 6.3 | 6.4 | 5.1 | 5.8 | 6.0 | 5.9 |
| CGE Red | LC % |  | 0.5 | n/a | n/a | 0.5 | n/a | n/a | 0.6 |
|  | Unknown % |  | 0.2 |  |  | 0.7 |  |  | 0.1 |
|  | HC % |  | 0.2 |  |  | 0 |  |  | 0.4 |
|  | Unknown % |  | 0 |  |  | 0 |  |  | 0 |
|  | 75 kDA % |  | 0 |  |  | 0.0 |  |  | 0 |
|  | 80 kDA % |  | 0.5 |  |  | 1.1 |  |  | 0.5 |
|  | 100 kDa % |  | 6.0 |  |  | 8.7 |  |  | 6.1 |
|  | BEAT' % |  | 4.1 |  |  | 8.7 |  |  | 3.3 |
|  | BEAT % |  | 83.1 |  |  | 74.4 |  |  | 82.6 |
|  | BEAT" % |  | 4.2 |  |  | 4.8 |  |  | 5.1 |
|  | IgG % |  | 1.1 |  |  | 1.1 |  |  | 1.3 |
|  | Aggregate % |  | 0 |  |  | 0 |  |  | 0 |

[1] The condition 1% TnBP incubation for 120 minutes was completely precipitated and was not analyzed These results show that BEAT®2 is stable for all TnBP conditions except 1% TnBP during 120 minutes of incubation where a precipitation was observed and no analytical results were provided. A degradation was noticed with the condition 0.3% TnBP+1% Tween 80 since the t0 by HPLC-SE, but not confirmed by CGE and HPLC-HIC. After analysis of the HPLC-SE raw data, the aggregates percentage are increase because of the Tween 80 remaining in the sample post treatment, Tween 80 is interfering with the method, indeed the retention time of the Tween 80 is very close to the aggregates retention time. Therefore, no degradation of the sample with the condition 0.3% TnBP+1% Tween 80 was observed. This first experiment was not optimum because the reaction was not stopped with the PD-10 buffer exchange, and Tween 80 was still present in the sample during the HPLC-SE analysis. Next, two others detergents were tested, Tween 20 and Triton X-100, a dilution to 0.3 g/L using PBS buffer was applied to each sample at each time point to stop the reaction (study 2). In Table 16 results analysis of HPLC-SE and HPLC-HIC are illustrated.

TABLE 16

S/D treatment of PA eluate results, study 2

A

| | | Standard BEAT®2-04 | PA eluate diluted to 0.3 g/L | 0.3% TnBP + 0.2% Triton X-100 | | 0.3% TnBP + 0.5% Triton X-100 | | 0.3% TnBP + 1% Triton X-100 | |
|---|---|---|---|---|---|---|---|---|---|
| | Incubation time (min) | | N/A | 0 | 90 | 0 | 90 | 0 | 90 |
| HPLC SE | Aggregates % | 2.2 | 2.6 | 4.6 | 4.5 | 8.3 | 5.7 | 15.4 | 7.6 |
| | Monomer % | 97.5 | 96.5 | 94.2 | 94.3 | 91.1 | 93.6 | 76.1 | 83.7 |
| | Fragments % | 0.2 | 0.9 | 1.2 | 1.0 | 0.6 | 0.7 | 8.4 | 8.6 |
| HPLC HIC | Before main % | 1.3 | 1.7 | 1.3 | 1.4 | 1.1 | 1.1 | 0.8 | 0.8 |
| | Main peak % | 95.6 | 76.8 | 67.0 | 67.1 | 58.6 | 60.0 | 44.7 | 45.1 |
| | Shoulder after main % | 0 | 15.8 | 14.1 | 14.1 | 9.8 | 8.8 | 7.3 | 7.2 |
| | Main + shoulder % | 95.6 | 92.6 | 81.1 | 81.2 | 68.4 | 68.8 | 52.0 | 52.3 |
| | After Main % | 3 | 5.7 | 17.6 | 17.5 | 30.4 | 30.0 | 47.1 | 46.9 |

B

| | | 0.3% TnBP + 0.2% Tween 80 [1] | | 0.3% TnBP + 0.5% Tween 80 | | 0.3% TnBP + 1% Tween 80 | | 0.3% TnBP + 0.2% Tween 20 | | 0.3% TnBP + 0.5% Tween 20 | | 0.3% TnBP + 1% Tween 20 | |
|---|---|---|---|---|---|---|---|---|---|---|---|---|---|
| | Incubation time (min) | 0 | 90 | 0 | 90 | 0 | 90 | 0 | 90 | 0 | 90 | 0 | 90 |
| HPLC SE | Aggregates % | 33.7 | 30.3 | 4.6 | 4.5 | 4.7 | 5.4 | 4.6 | 4.8 | 4.9 | 4.7 | 5.2 | 5.0 |
| | Monomer % | 59.3 | 62.5 | 94.3 | 94.3 | 94.0 | 93.5 | 94.2 | 94.1 | 94.0 | 94.2 | 93.6 | 93.9 |
| | Fragments % | 7.0 | 7.3 | 1.1 | 1.1 | 1.3 | 1.1 | 1.2 | 1.1 | 1.1 | 1.1 | 1.3 | 1.2 |
| HPLC- HIC | Before main % | 1.6 | 1.6 | 1.7 | 1.6 | 1.6 | 1.6 | 1.7 | 1.6 | 1.7 | 1.7 | 1.6 | 1.6 |
| | Main peak % | 75.6 | 75.7 | 75.6 | 76.9 | 76.8 | 75.2 | 76.0 | 76.3 | 75.6 | 77.0 | 74.1 | 77.3 |
| | Shoulder after main % | 15.7 | 15.9 | 15.7 | 15.0 | 14.2 | 16.6 | 15.1 | 15.0 | 15.4 | 14.4 | 17.4 | 14.8 |
| | Main + shoulder % | 91.3 | 91.6 | 91.3 | 91.9 | 91.0 | 91.8 | 91.1 | 91.3 | 91.0 | 91.4 | 91.5 | 92.1 |
| | After Main % | 6.9 | 6.7 | 7.1 | 6.5 | 7.5 | 6.5 | 7.0 | 7.0 | 7.2 | 6.9 | 6.8 | 6.3 |

Table 16 shows that: for samples treated with 0.3% TnBP in combination with Triton X-100, degradation was appearing for the higher concentration of Triton X-100 (1%), with around 15% of aggregates and 8% of fragments by HPLC-SE. In samples treated with 0.3% TnBP in combination with Tween 80 and Tween 20, except condition with 0.2% Tween 80, no signs of degradation were noticed by HPLC-SE and HPLC-HIC compared to the PA Eluate diluted. No difference was observed between t=0 and t=90 minutes on all samples conditions.

Overall these results show that BEAT®2 is stable in most of the S/D treatment conditions up to 120 minutes, and that therefore S/D treatment is a valuable option of the viral inactivation of a BEAT® 2-containing solution.

S/D Treatment of Clarified Harvest (PA Load)

Based on the results obtained from the studies on S/D treatment of the PA eluate, the decision of testing S/D treatment on clarified harvest was taken to ensure better solvent and detergent removal and therefore to increase safety.

The first two purification steps were viral inactivation and PA chromatography instead of PA chromatography followed by viral inactivation.

TABLE 17

S/D treatment of clarified harvest conditions

| | Solvent/detergent conditions |
|---|---|
| Clarified Harvest S/D Run 1 | 0.3% TnBP + 1% Tween 80 |
| Clarified Harvest S/D Run 2 | 0.3% TnBP + 1% Tween 20 |
| Clarified Harvest S/D Run 3 | 0.3% TnBP + 1% Triton X-100 |

For this step, different conditions were tested using TnBP in combination with Tween 20, Tween 80 and Triton X-100. The mix of solvent and detergent was added to PA load, incubated for around 20 minutes and loaded into a Kaneka KanCapA resin column. All results are reported in Table 18.

TABLE 18

S/D treatment of clarified harvest results

| | | Run 1 | Run 2 | Run 3 | Run 4 |
|---|---|---|---|---|---|
| S/D mix preparation | Conditions | No treatment | 0.3% TnBP + 1% Tween 80 | 0.3% TnBP + 1% Tween 20 | 0.3% TnBP + 1% Triton X-100 |
| S/D mix addition | PA loading duration (h) | | 3 h10 | 3 h20 | 3 h12 |
| | Incubation time (min) | | 19 | 12 | 22 |
| | Contact time (incubation + PA loading) | | 3 h29 | 3 h32 | 3 h34 |

TABLE 18-continued

S/D treatment of clarified harvest results

| | | Run 1 | Run 2 | Run 3 | Run 4 |
|---|---|---|---|---|---|
| Loading Factor g/L | | 35 | 35 | 35 | 35 |
| PA Eluate Parameters | pH | 4.3 | 4.3 | 4.3 | 4.3 |
| | Conductivity (mS/cm) | 1.25 | 1.28 | 1.26 | 1.32 |
| | Volume (CV) | 3.5 | 4.5 | 5.0 | 4.9 |
| | Titer Nanodrop (g/L) | 7.0 | 5.2 | 4.7 | 4.7 |
| | PA Yield | 70% | 67% | 66% | 66% |
| PA Eluate HPLC-SE | Aggregate % | 4.0 | 4.7 | 3.3 | 4.3 |
| | Monomer % | 89.3 | 89.2 | 90.4 | 89.8 |
| | Tailing % | 6.1 | 5.4 | 5.5 | 5.1 |
| | Fragment % | 0.6 | 0.8 | 0.9 | 0.8 |
| PA Eluate HPLC-HIC | Before main % | 4.4 | 4.5 | 4.4 | 4.6 |
| | Main peak % | 89.5 | 89.1 | 89.1 | 88.8 |
| | After main % | 6.1 | 6.4 | 6.5 | 6.6 |
| PA Eluate CGE non-reduced | LC % | 0.6 | 0.6 | 0.6 | 0.6 |
| | Unknown % | 0.1 | 0.1 | 0.2 | 0.1 |
| | HC % | 0.6 | 0.6 | 0.7 | 0.6 |
| | Unknown % | 0 | 0 | 0 | 0 |
| | 75 kDA % | 0 | 0 | 0 | 0 |
| | 80 kDA % | 0.6 | 0.6 | 0.7 | 0.6 |
| | unknown % | 0 | 0 | 0 | 0 |
| | 100 kDa % | 8.1 | 8.1 | 8.4 | 8.1 |
| | BEAT' % | 3.1 | 3.1 | 3.5 | 3.6 |
| | BEAT % | 83.8 | 83.8 | 82.5 | 82.2 |
| | Unknown after BEAT % | 2.5 | 2.5 | 2.8 | 3.5 |
| | IgG % | 0.6 | 0.6 | 0.6 | 0.7 |
| | Aggregates % | 0.1 | 0.1 | 0 | 0.1 |
| PA Eluate iCE3 | Main % | 39.5 | 40.2 | 43.6 | 41.6 |
| | Acidic % | 60.5 | 59.8 | 56.4 | 58.4 |
| Tween 80 | Tween 80 contain % (w/v) | n/a | 0.00027 | n/a | n/a |

Similar performances were obtained with all the S/D conditions, results of PA eluate treated (run 2, 3 and 4) are comparable to run 1 (without S/D incubation) on yield and all analytical data, but they have slightly higher CV elution (from 3.5 to around 5) and lower concentrations values (from 7.0 g/L to around 5 g/L). The removal of the Tween 80 was efficient, only some traces of Tween 80 were present after the PA purification.

S/D treatment carried out before the PA step demonstrated to have a potential to be used for viral inactivation since the reaction was stopped by the PA purification and the purity was not impacted. Furthermore, the subsequent CEX chromatography additionally removes remaining traces of S/D present after PA chromatography.

Since the results obtained with the different detergents were similar, Tween 80 was selected for subsequent analyses since already used for other process steps. Thus, the condition combining 0.3% TnBP+1% Tween 80 was selected for the S/D treatment of the clarified harvest, and the treatment considered for the viral inactivation of BEAT® 2-containing solution.

High pH Treatment of PA Eluate

A small volume (20 mL) of PA eluate from clone 1 was used to test the stability of BEAT®2 under high pH incubation. Firstly, several buffers were tested to reach the targeted pH 11.0, 0.5 M acetate pH 12.0, 0.5 M citrate pH 12.0, 1 M Tris pH 12.0, 0.25 M Histidine pH 12.0, 0.5 M L-Arginine pH12.0, 0.25 M phosphate pH12.0, 0.1 M NaOH and finally 0.5 M NaOH, as shown in Table 19.

TABLE 19

Buffers and ratio for high pH treatment

| | Ratio (mL/L) | pH reached |
|---|---|---|
| Acetate 0.5M pH 12.0 | 820 | 5.8 |
| Citrate 0.5M pH 12.0 | 1300 | 6.8 |

TABLE 19-continued

Buffers and ratio for high pH treatment

| | Ratio (mL/L) | pH reached |
|---|---|---|
| Tris 1M pH 12.0 | 1500 | 10.4 |
| Histidine 0.25M pH 12.0 | 1200 | 10.2 |
| L-Arginine 0.5M pH 12.0 | 1400 | 10.8 |
| Phosphate 0.25M pH 12.0 | 230 | 11.0 |
| NaOH 0.1M | 440 | 11.0 |
| NaOH 0.5M | 85 | 11.0 |

The target pH 11.0 was not reached with all buffers, for instance with acetate and citrate 0.5 M pH 12.0 and Tris 1 M pH 12.0. The ratio volume for the pH adjustment was one criteria for the buffer selection, the aim was to have the minimum ratio to avoid large volumes for next step.

After this first screening, 0.25 M phosphate pH 12.0, 0.1 M NaOH and 0.5 M NaOH were selected to perform further studies.

Incubation at pH 11.2 was performed for 30, 45 and 60 minutes with the selected buffers, see Table 20. For all the experiments, after the treatment, the product was analyzed by HPLC-SE, HPLC-HIC, CGE (non-reduced) and by iCE3. The results are shown in Table 21.

TABLE 20

High pH treatment conditions

| pH target | | | 11.2 | |
|---|---|---|---|---|
| Incubation time (min) | 0 | 30 | 45 | 60 |

TABLE 21

High pH treatment results

| | | PA eluate | Phosphate 0.25M pH 12.0 | | | | NaOH 0.1M | | | | NaOH 0.5M | | | |
|---|---|---|---|---|---|---|---|---|---|---|---|---|---|---|
| | Ratio (mL/L) after N+ | | 270 | | | | 460 | | | | 92 | | | |
| | pH reached | | 11.2 | | | | 11.2 | | | | 11.2 | | | |
| | Conductivity (mS/cm) | 1.21 | 11.10 | | | | 3.95 | | | | 3.10 | | | |
| | Yield % | | 96.8 | | | | 92.5 | | | | 95.1 | | | |
| | Incubation time (min) | | 0 | 30 | 45 | 60 | 0 | 30 | 45 | 60 | 0 | 30 | 45 | 60 |
| HPLC-SE | Aggregates % | 4.1 | 8.0 | 8.4 | 8.8 | 9.2 | 6.5 | 6.0 | 6.4 | 6.0 | 4.8 | 4.9 | 5.2 | 5.1 |
| | Monomer % | 94.2 | 90.9 | 90.4 | 90.1 | 89.7 | 92.4 | 93.0 | 92.6 | 93.0 | 94.1 | 94.1 | 93.7 | 93.9 |
| | Fragments % | 1.7 | 1.2 | 1.2 | 1.2 | 1.2 | 1.1 | 1.0 | 1.0 | 1.0 | 1.1 | 1.0 | 1.1 | 1.0 |
| HPLC-HIC | HPLC-HIC: before main % | 1.7 | 1.6 | 1.6 | 1.6 | 1.6 | 1.6 | 1.6 | 1.6 | 1.7 | 1.6 | 1.6 | 1.7 | 1.6 |
| | HPLC-HIC: Main peak % | 90.9 | 91.8 | 91.4 | 91.0 | 91.1 | 92.1 | 92.7 | 92.3 | 92.5 | 93.0 | 92.9 | 92.9 | 92.9 |
| | HPLC-HIC: After main % | 7.4 | 6.7 | 7.0 | 7.5 | 7.3 | 6.3 | 5.7 | 6.1 | 5.9 | 5.3 | 5.5 | 5.5 | 5.5 |
| CGE non-re-duced | CGE LC % | 0.6 | 0.6 | n/a | | 0.5 | 0.6 | n/a | | 0.6 | 0.6 | n/a | | 0.5 |
| | Unknown after LC % | 0.1 | 0.1 | | | 0.1 | 0.1 | | | 0.1 | 0.1 | | | 0.1 |
| | HC % | 0.8 | 0.4 | | | 0.5 | 0.7 | | | 0.7 | 0.6 | | | 0.6 |
| | Unknown after HC % | 0.7 | 0.0 | | | 0.2 | 0.5 | | | 0.4 | 0.3 | | | 0.4 |
| | Fragment 75 kDA % | 0.1 | 0.0 | | | 0.1 | 0.1 | | | 0.1 | 0.1 | | | 0.1 |
| | Fragment 80 kDA % | 0.2 | 0.3 | | | 0.3 | 0.3 | | | 0.2 | 0.3 | | | 0.3 |
| | Fragment 100 kDa % | 6.3 | 5.5 | | | 5.6 | 6.0 | | | 5.4 | 5.8 | | | 5.5 |
| | BEAT' % | 4.2 | 3.2 | | | 3.6 | 3.9 | | | 3.2 | 3.4 | | | 3.4 |
| | BEAT % | 82.2 | 85.5 | | | 85.0 | 83.4 | | | 84.0 | 84.7 | | | 84.8 |
| | BEAT" % | 4.0 | 3.9 | | | 3.3 | 3.8 | | | 3.9 | 3.7 | | | 3.6 |
| | IgG % | 0.8 | 0.5 | | | 0.5 | 0.7 | | | 1.1 | 0.5 | | | 0.5 |
| | Aggregates % | 0.0 | 0.0 | | | 0.2 | 0.1 | | | 0.2 | 0.0 | | | 0.0 |
| iCE3 | Acidic % | n/a | 59.5 | | | 60.7 | 59.4 | | | 61.6 | 60.1 | | | 61.4 |
| | Main % | | 40.5 | | | 39.3 | 40.6 | | | 38.4 | 39.9 | | | 38.6 |

During all the experiments, precipitation was observed around pH 6.0 and disappeared at pH 11.0. Yields runs were around 95%, it was assumed that is was precipitation of impurities even if no analysis were performed on impurities, the same phenomenon was also observed for other projects, for neutralization after low pH incubation with no loss of product. BEAT®2 was stable at pH 11.2 for incubation up to 60 minutes. Indeed with NaOH 0.5 M buffer, the monomer percentage by HPLC-SE was stable after 60 minutes at pH 11.2, equivalent results by CGE (only last time points were tested), iCE3 and HPLC-HIC, no degradation was observed compared to the starting material. This experiment was repeated and results were confirmed. Based on these results, pH treatment using 0.5 M NaOH buffer was considered as a potential alternative to the low pH viral inactivation.

d. Testing the Activity of BEAT®2
Material, Methods and Equipment

To investigate the impact of solvent/detergent, Arginine and high pH treatments, binding affinity assays were performed on different samples treated by solvent detergent (0.3% TnBP+1% Tween 80); after incubation with 0.8 M Arginine at pH 4.0 and at pH 5.5, and after high pH treatment (NaOH O,5M, pH11.2). Two antigens targets were tested, the CD38 and CD3.

Results and Conclusions

No significant difference was observed for all samples, indeed Kd values are comparable. So there was no effect of all these treatments on the antibody activity. The results of this analysis are reported in Table 22.

TABLE 22

Binding affinity assays results

A. hsCD38

| Sample | Treatment | Ka (1/Ms) | Kd (1/s) | KD (pM) | Relative KD (% RS) | EC50 | % deviation EC50 |
|---|---|---|---|---|---|---|---|
| RS | — | 1.034e6 | 4.568e−4 | 442 | 100 | 1.914 | 0 |
| 1 | S/D | 1.106e6 | 3.755e−4 | 341 | 77.1 | 1.620 | −15.4 |
| 2 | 0.8M Arg, pH4.0 | 1.027e6 | 5.205e−4 | 507 | 114.7 | 1.981 | +3.5 |
| 3 | 0.8M Arg, pH5.5 | 1.047e6 | 4.594e−4 | 439 | 99.3 | 1.927 | +0.7 |
| 4 | High pH | 1.037e6 | 4.826e−4 | 467 | 105.6 | 1.947 | +1.7 |

TABLE 22-continued

Binding affinity assays results

B. hsCD3e 1-26Fc

| Sample | Treatment | Ka (1/Ms) | Kd (1/s) | KD (nM) | Relative KD (% RS) | EC50 | % deviation EC50 |
|---|---|---|---|---|---|---|---|
| RS | — | 2.2e5 | 1.31e−2 | 59.4 | 100 | 8.24 | 0 |
| 1 | S/D | 2.12e5 | 8.22e−3 | 38.7 | 65.1 | 5.41 | −34.4 |
| 2 | 0.8M Arg, pH4.0 | 1.93e5 | 4.75e−3 | 24.8 | 41.7 | 4.00 | −51.5 |
| 3 | 0.8M Arg, pH5.5 | 2.22e5 | 7.38e−3 | 33.3 | 56.0 | 4.34 | −47.3 |
| 4 | High pH | 2.12e5 | 7.07e−3 | 33.4 | 56.2 | 4.50 | −45.4 |

EXAMPLE 2: ARGININE TREATMENT OF PA ELUATE CONTAINING LOW pH-LIABLE ANTIBODIES, LEADS TO AN EFFECTIVE VIRAL INACTIVATION ONLY AT pH LEVELS THAT IMPAIR THE STABILITY OF THE ANTIBODY

Based on the stability and activity studies reported in Example 1, the most promising viral inactivation methods were further tested for their ability to inactivate viruses. The effectiveness of the viral inactivation was evaluated by doing a spiking study at Bioreliance. Test samples were taken before and after each treatment and analyzed for viral titre. First, VRV study on Arginine treatment was carried out.

Materials, Methods and Equipment

Only one virus, MLV, which is a typical model virus used for biological products derived from CHO cell lines such as monoclonal antibody, was used for this study. A total of 7 runs were performed. PA eluate from development runs was used as starting material. Different stock buffers of Arginine at the different pH (pH 4.0, pH 4.75, pH 4.79 and pH 5.5) were used to reach the target pH and concentration. The samples were neutralized using 250 mM Histidine pH 12.0 buffer around pH 6.0 to stop the reaction. Table 23 summarizes the conditions tested during the VRV study.

TABLE 23

| Conditions for VRV study on Arginine treatment | | | |
|---|---|---|---|
| Run | Arginine concentration (mM) | pH | Time points (min) |
| 1 | 0 | 4.0 | 0, 120 |
| 2 | 0.40 | 4.0 | 0, 60 |
| 3 | 0.80 | 4.0 | 0, 120 |
| 4 | 0.80 | 4.75 | 0, 60 |
| 5 | 0.38 | 4.79 | 0, 120 |
| 6 | 0 | 5.5 | 0, 60, 120 |
| 7 | 0.80 | 5.5 | 0, 120 |

Log reduction values was calculated with respect to the neutralized load sample, a 5 plate large volume plating as well as a standard titration was performed on the t=60 min sample. The neutralized load hold sample was held at 16.0° C. to 20.0° C. for 60 minutes (runs 2, 4 and 6) or 120 minutes (runs 1, 3, 5 and 7).

Results and Conclusions

The results of VRV study on Arginine treatment are presented in Table 24.

TABLE 24

| Results of VRV study on Arginine treatment Arginine | | | | |
|---|---|---|---|---|
| Run | Arginine concentration (mM) | pH | Time points | $log_{10}$ reduction factor |
| 1 | 0 | 4 | L, H, 0-1, 120 min | 1.14 +/0.46 |
| 2 | 0.4 | 4 | L, H, 0-1, 60 min | 4.16 +/− 0.32 |
| 3 | 0.8 | 4 | L, H, 0-1, 120 min | 4.10 +/− 0.35 |
| 4 | 0.8 | 4.75 | L, H, 0-1, 60 min | 2.82 +/− 0.4 |
| 5 | 0.38 | 4.79 | L, H, 0-1, 120 min | no reduction |
| 6 | 0 | 5.5 | L, H, 0-1, 60, 120 min | 0.35 +/− 0.4 |
| 7 | 0.8 | 5.5 | L, H, 0-1, 120 min | no reduction |

Since only treatment at pH 4.0 gives an effective virus clearance, and at this pH condition BEAT®2 was shown to be degraded (Example 1), Arginine treatment was discarded from the potential options of viral inactivation treatment of BEAT® 2-containing solutions.

EXAMPLE 3: S/D TREATMENT OF PA ELUATE CONTAINING LOW pH-LIABLE ANTIBODIES, LEADS TO AN EFFECTIVE VIRAL INACTIVATION

Next, the ability of solvent detergent treatment of BEAT® 2-containing PA eluate to inactivate viruses, was tested.

Materials, Methods and Equipment

The effectiveness of the viral inactivation using S/D treatment of the PA eluate was evaluated by doing a spiking study at Bioreliance. Only one virus, MLV, which is a typical model virus used for biological products derived from CHO cell lines such as monoclonal antibody, was used for this study. The target concentrations was 0.3% of TnBP and 1% of Tween 80. The study was performed for PA eluate (around pH 4.2) and neutralized PA eluate (pH 6.0). The operating conditions for temperature were 15° C.+/−2° C. which is a worst scenario for chemical inactivation (lower temperature leading to a slower inactivation). The process operation conditions are typically 18 to 25° C. depending on the manufacturing facility. A kinetic was performed with time points 0, 10, 30 and 60 min. A summary of the conditions tested for BEAT®2 is presented in Table 25.

TABLE 25

Conditions for VRV study on S/D treatment of PA eluate

| Conditions | Sample type | TnBP % spike | Tween 80 % spike |
|---|---|---|---|
| 1 | Protein A eluate | 0.3 | 1 |
| 2 | Protein A eluate neutralized (pH 6.0) | | |

The results of the VRV studies, in Table 26 show that S/D treatment of PA eluate leads to an efficient viral inactivation when PA eluate is not neutralized and to a moderate inactivation when PA eluate is neutralized after 60 minutes of incubation, confirming S/D treatment of PA eluate a valid VI method for BEAT®2 purification process

TABLE 26

Results of VRV study on S/D treatment of PA eluate
S/D treatment, 0.3% TnBP + 1% Tween 80

| Starting material | CL (95%) | Neutralized load Titre/ml | t0 Titre/ml | t10 min Titre/ml | t30 min Titre/ml | t60 min Titre/ml | $\log_{10}$ reduction factor |
|---|---|---|---|---|---|---|---|
| PA eluate, pH 4.2 | Lower | 6.52 | 3.66 | | | | ≥5.54 ± 0.38 |
| | Mean | 6.89 | 3.83 | 3.13 | 3.13 | 1.35 | |
| | Upper | 7.27 | 4.01 | | | | |
| PA eluate, neutralized to pH 6.0 | Lower | 6.39 | 4.57 | 3.87 | 3.44 | 3.24 | ≥3.42 ± 0.34 |
| | Mean | 6.72 | 4.88 | 4.18 | 3.74 | 3.30 | |
| | Upper | 7.05 | 5.19 | 4.49 | 4.05 | 3.36 | |

EXAMPLE 4: S/D TREATMENT OF CLARIFIED HARVEST CONTAINING LOW pH-LIABLE ANTIBODIES, LEADS TO AN EFFECTIVE VIRAL INACTIVATION

Additionally, VRV studies were performed on treatment of the BEAT® 2-containing clarified harvest by solvent and detergents.

VRV Study 1

Materials, Methods and Equipment

Only one virus, MLV, which is a typical model virus used for biological products derived from CHO cell lines such as monoclonal antibody, was used for this study. A total of 3 runs were performed using a mix of TnBP with Tween 80. Same percentage of TnBP (0.3%) and different percentages of Tween 80 were tested (0.25, 0.5 and 1.0%). After the spiking with S/D, the product was agitated until the end of incubation. Once each time point was collected it was quenched immediately by diluting 1/25 and neutralizing to pH 6.00-8.00. Table 27 reports the conditions tested at BioReliance during the VRV study for S/D treatment:

TABLE 27

Conditions for VRV study of S/D treatment of clarified harvest

| Run | TnBP % | Tween 80 % | Time points (min) |
|---|---|---|---|
| 1 | 0.3 | 0.25 | 0, 10, 30 and 60 |
| 2 | 0.3 | 0.5 | 0, 10, 30 and 60 |
| 3 | 0.3 | 1.0 | 0, 10, 30 and 60 |

Log reduction values was calculated with respect to the quenched load sample, a 5 plate large volume plating as well as a standard titration was performed on the t=60 min sample. The Quenched Load Hold sample was held at 16.0° C. to 20.0° C. for 60 minutes.

Results and Conclusions

In Table 28, a summary of VRV study results are presented.

TABLE 28

Results of VRV study on S/D treatment of clarified harvest
S/D treatment

| Run | Tween 80% | TnBP % | $\log_{10}$ reduction factor |
|---|---|---|---|
| 1 | 0.25 | 0.3 | ≥4.93 +/− 0.25 |
| 2 | 0.5 | 0.3 | ≥4.50 +/− 0.00 |
| 3 | 1 | 0.3 | ≥4.88 +/− 0.44 |

S/D treatment of clarified harvest result to be effective in the inactivation of MLV virus at all the tested conditions, even when lower concentration of Tween 80 (0.25%) is used.

VRV Study 2

Additionally the capability of solvent detergent treatment of the clarified harvest to inactivate MLV and PRV viruses was evaluated under worse case conditions.

Materials, Methods and Equipment

Process load samples were spiked with viral stocks and analyzed at Bioreliance.

This was performed under "worst case" conditions as shown in Table 29. The lowest clearance factor was reported for each duplicate.

TABLE 29

"Worst case" conditions for VRV validation studies

| Virus Reducing Process Step | Worst case | Temperature [° C.] |
|---|---|---|
| Viral Inactivation S/D | Tween 80: 0.75%/1.25% TnBP 0.2%/0.4% | 15° C. ± 2° C. |

Results and Conclusions

The chemical viral inactivation step developed for BEAT®2 was evaluated for its efficiency on MLV and PRV inactivation with a S/D mix of 0.2% TnBP+0.75% Tween 80 and 0.4% TnBP+1.25% Tween 80 using harvest lot 1 and lot 2.

For both virus experiments, same protocol was applied, a comparison from scaled-down process to clinical scale process is shown in Table 30.

TABLE 30

Chemical Inactivation scale down model

| Parameters | Scale Down VRV Study | Manufacturing Scale Lot 1 Lot 2 |
|---|---|---|
| Viral Inactivation | Solvent detergent (TnBP + Tween 80) | |
| TnBP % | 0.2% and 0.4% | 0.3% |
| Tween 80% | 0.75% and 1.25% | 1.0% |
| Inactivation duration | 1 hour | 6.5 hours |
| Protein Concentration | 0.4 g/L | 0.4 g/L |
| Temperature | 15.0 ± 2.0° C. | 22.5 ± 2.5° C. |

Table 31 shows, for the MLV, the Log Reduction Factor calculated for each run.

TABLE 31

$\log_{10}$ virus reduction value for MLV for Chemical Virus inactivation (standard assay)

| | $\log_{10}$ total virus | | | |
|---|---|---|---|---|
| | 0.75% Tween 80/0.2% TnBP | | 1.25% Tween 80/0.4% TnBP | |
| Sample | Run 1 | Run 2 | Run 3 | Run 4 |
| Load | 6.19 | 6.46 | 6.72 | 6.37 |
| 5 min | 4.88 | 5.41 | 3.13 | 3.21 |
| 10 min | 3.75 | 4.36 | 3.13 | 3.13 |
| 30 min | 3.31 | 3.83 | 3.13 | 3.13 |
| 60 min | 2.16 | 2.67 | 1.35 | 1.35 |
| $\log_{10}$ reduction factor | 4.03 | 3.79 | ≥5.37 | ≥5.02 |
| Load Hold | 6.37 | 6.46 | 6.46 | 6.63 |

These results show that the viral inactivation is effective during the S/D treatment, the total $\log_{10}$ virus is decreasing over the time, less 1.31 $\log_{10}$, 2.44 $\log_{10}$, 2.88 $\log_{10}$ and 4.03 $\log_{10}$ respectively after 5, 10, 30 and 60 min of incubation.

Additionally, aliquots were collected during the S/D runs, were frozen and analysed on Tween 80 and on TnBP percentage content, results are illustrated below in Table 32.

TABLE 32

Tween 80 and TnBP results for MLV for Chemical Virus Inactivation

| | 0.75% Tween 80/0.2% TnBP | | 1.25% Tween 80/0.4% TnBP | |
|---|---|---|---|---|
| Sample | Run 1 | Run 2 | Run 3 | Run 4 |
| Tween 80% (w/w) - t0 | 0.71 | 0.52 | 0.91 | 0.89 |
| Tween 80% (w/w) - t60 min | 0.70 | 0.54 | 0.92 | 0.88 |
| TnBP % (w/w) - t0 | 0.21 | 0.15 | 0.47 | 0.45 |
| TnBP % (w/w) - t60 min | 0.21 | 0.16 | 0.48 | 0.42 |

These Results Indicate that:

Chemical inactivation at low concentration (0.75% Tween 80/0.2% TnBP) showed reduction factors of 4.03 and 3.79 $\log_{10}$ for run 1 and run 2 respectively, which means that low S/D concentration was moderately effective for inactivation of MLV. Results presented in Table 31 demonstrate however, that the variation between run 1 and 2 (0.71% and 0.52%) was significant regarding the Tween 80 percentage. Only 0.52% of Tween 80 and 0.15% of TnBP were measured for run 2 but this is a worst case as these are low concentrations. It can be concluded that targets of 0.75% Tween 80 and 0.2% TnBP were not reached. The reduction was lower for the run performed with the lower concentrations of Tween 80 and TnBP, 0.52% Tween 80 and 0.15% TnBP (run 2), which is considered as worst case.

Chemical inactivation at high concentration (1.25% Tween 80/0.4% TnBP) showed reduction factors of ≥5.37 and ≥5.02 $\log_{10}$ for run 3 and run 4 respectively, which means that as expected an higher S/D concentration was more effective for inactivation of MLV. Results presented in Table 31 demonstrate, that the variation between run 3 and 4 (0.91 and 0.89) was not significant different regarding the Tween 80 percentage. But again the target of 1.25% Tween 80 was not reached for both runs, indeed only 0.91% and 0.89% were measured for respectively run 3 and run 4. Concerning the TnBP data, the runs were performed with 0.48% instead of 0.40% (run 3 t60 min). Again the results on virus inactivation are very logical, the run 3 with higher Tween 80 and TnBP % allow to obtain a best virus inactivation. To conclude, even in the worst case scenario on MLV virus inactivation (run 2, 0.52% Tween 80 and 0.15% TnBP) it was obtained a moderately effective reduction of 3.79 $\log_{10}$.

Table 33 shows for the PRV the % Tween 80 and TnBP measured and $\log_{10}$ values obtained for the different Chemical viral inactivation samples and the Log Reduction Factor calculated for each run:

TABLE 33

$\log_{10}$ virus reduction value for PRV for Chemical Virus inactivation (standard assay)

| | $\log_{10}$ total virus | | | |
|---|---|---|---|---|
| | 0.75% Tween 80/0.2% TnBP | | 1.25% Tween 80/0.4% TnBP | |
| Sample | Run 1 | Run 2 | Run 3 | Run 4 |
| Load | 6.11 | 5.84 | 5.84 | 6.37 |
| 5 min | 2.43 | 3.38 | 2.43 | 3.21 |
| 10 min | 2.43 | 2.43 | 2.43 | 3.13 |
| 30 min | 2.43 | 2.43 | 2.43 | 3.13 |
| 60 min | 0.62 | 0.65 | 0.65 | 1.35 |
| $\log_{10}$ reduction factor | ≥5.46 | ≥5.19 | ≥5.19 | ≥5.46 |
| Load Hold | 6.37 | 6.46 | 5.84 | 5.93 |

The viral inactivation is effective during the incubation, the total $\log_{10}$ virus is decreasing over the time, less 3.68 $\log_{10}$ directly after 5 of treatment and 5.49 $\log_{10}$ 60 min of incubation. Aliquots were collected during the S/D runs, were frozen and analysed on Tween 80 and on TnBP percentage content, results are illustrated below in Table 34.

TABLE 34

Tween 80 and TnBP results for PRV for Chemical Virus Inactivation

| | 0.75% Tween 80/0.2% TnBP | | 1.25% Tween 80/0.4% TnBP | |
|---|---|---|---|---|
| Sample | Run 1 | Run 2 | Run 3 [6] | Run 4 [6] |
| Tween 80% (w/w) - t0 | 0.74 | 0.57 | 0.80 | 1.17 |
| Tween 80% (w/w) - t60 min | 0.70 | 0.57 | 1.01 | 0.88 |

TABLE 34-continued

Tween 80 and TnBP results for PRV for Chemical Virus Inactivation

| | 0.75% Tween 80/0.2% TnBP | | 1.25% Tween 80/0.4% TnBP | |
|---|---|---|---|---|
| Sample | Run 1 | Run 2 | Run 3 [6] | Run 4 [6] |
| TnBP % (w/w) - t0 | 0.15 | <0.15 | 0.27 | 0.37 |
| TnBP % (w/w) - t60 min | <0.15 | <0.15 | 0.33 | 0.29 |

PRV Results Show that:

Chemical inactivation at low concentration (0.75% Tween 80/0.2% TnBP) showed reduction factors of ≥5.46 and ≥5.19 $\log_{10}$ for run 1 and run 2 respectively, which means that low S/D concentration was effective for inactivation of PRV. Results presented in Table 33 demonstrate however, that the variation between run 1 and run 2 was significant regarding the Tween 80 percentage results (0.74% and 0.57%). The target of 0.75% Tween 80 was not reached for run 2, indeed only 0.57% was measured, this is a worst case scenario, because of the low detergent concentration. For TnBP, both runs show comparable values lower than the target, 0.15% instead of 0.20%. As expected, with less Tween 80 percentage, run 2 presented a lower virus reduction compared to run 1 with ≥5.19 $\log_{10}$.

Chemical inactivation at high concentration (1.25% Tween 80/0.4% TnBP) showed reduction factors of ≥5.19 and ≥5.46 $\log_{10}$ for run 3 and run 4 respectively, which means that, as expected, an higher S/D concentration was more effective for inactivation of PRV. Results presented in Table 33 demonstrate, that there was a variation for Tween 80 and TnBP values between time point t0 and time point t60 minutes for both runs, effectively for run 3, Tween 80 content at t0 is 0.80% and at t60 min is 1.01%, same for TnBP t0 0.27% and t60 min 0.33%. Again the target of 1.25% Tween 80 was to reached for both runs, but despite of this as the worst case on virus inactivation is a low concentration of S/D. Concerning the TnBP data, the runs were performed to 0.48% instead of 0.40% (run 3 t60 min). Again the results on virus reduction are very logical, the run 3 with higher Tween 80 and TnBP % presented better virus clearance.

The higher virus inactivation obtained with the PRV virus compared to the MLV, using identical chemical inactivation, is expected indeed the PRV has a lower physico-chemical resistance.

To conclude all the data, in the worst case scenario (run 2) there is an effective PRV virus inactivation with 5.19 $\log_{10}$.

Taken together, the results of Study 1 and Study 2 demonstrate that VI is achieved using S/D treatment of PA load.

EXAMPLE 5: HIGH pH TREATMENT OF PA ELUATE, CONTAINING LOW pH-LIABLE ANTIBODIES, LEADS TO A MODERATELY EFFECTIVE VIRAL INACTIVATION AT pH THAT PRESERVE THE STABILITY OF THE ANTIBODY

Materials, Methods and Equipment

VRV studies on high pH treatment of PA eluate containing BEAT®2 were conducted. Only one virus, MLV, was used for this study. The experiment was carried out in a single run at pH 10.8 (based on process target of pH 11.0, worst case condition with a lower pH). A PA eluate from development runs was used for this study, the pH was increased using the selected buffer 0.5 M NaOH. Upon collection, all samples were neutralized to pH 6-8 with 3.7% HCl.

Log reduction values was calculated with respect to the Neutralized Load sample, a 5 plate large volume plating as well as a standard titration was performed on t=60 min sample. The neutralized load hold sample was held at 16.0° C. to 20.0° C. for 60 minutes.

Results and Conclusions

In Table 35 the VRV results obtained during this study are presented.

TABLE 35

VRV results for high pH treatment

| CL (95%) | Neutralized Load Titre/ml | 0-1 min Titre/ml | 10 min Titre/ml | 30 min Titre/ml | 60 min Titre/ml | $\log_{10}$ Reduction Factor |
|---|---|---|---|---|---|---|
| lower | 5.16 | 2.28 | 2.43 | 1.07 | 2.14 | 3.18 ± 0.26 |
| mean | 5.41 | 2.51 | 2.85 | 1.98 | 2.23 | |
| upper | 5.66 | 2.75 | 3.27 | 2.89 | 2.31 | |

Incubation of BEAT® 2-containing PA eluate at high pH is moderately effective in the inactivation of MLV viruses after 1 min of incubation till 60 min of incubation, when the reduction factor is 3.18 $\log_{10}$. High pH treatment can therefore be considered as a valid alternative of low pH treatment in the process of purification BEAT® 2.

EXAMPLE 6: HIGH pH TREATMENT OF PA ELUATE IS AN EFFICIENT INACTIVATION STEP IN THE PURIFICATION PROCESS OF THE LOW pH-LIABLE ANTIBODY BEAT®2

To further investigate the possibility to use high pH treatment as viral inactivation step in the manufacturing process of BEAT® 2, additional stability and activity studies have been carried. The hold time impact has been evaluated at different time points including worse case scenarios, such as at 24 h of incubation.

Materials, Methods and Equipment

The starting material used in this study was representative PA eluate.

All chemicals were pharmacopoeia grade (US or EP). In-process 0.2 μm filtration steps were typically performed for all buffers and process intermediates. In addition, magnetic stirrer, pH and conductivity meter were used.

The time points tested were 1 hour, 2 hours and 4 hours at RT and beyond this point, the product was put at 5±3° C. up to 24 hours of incubation. About 100 mL of PA eluate was basified under agitation using a magnetic stirrer to pH 11.2 in a Nalgene bottle using NaOH 0.5 M. This pH was selected as a worst case scenario for product quality, in order to validate the target pH 11.0 of the process. The product at high pH was incubated except for time point t0 which was immediately neutralized as described below. At each time point, about 10 mL of high pH product was transferred into a 50 mL TPP tube and neutralized by decreasing the pH up to pH 6.0 using HCl 3.7% (neutralization step) in order to stop the VI reaction, before being frozen.

The product quality was analysed by HPLC-SE, iCE and CGE for all time points. PA eluate not neutralized and without any VI treatment was also analysed and used as reference.

TABLE 36

High pH testing conditions

| Incubation time (h) | Time points | | | | |
|---|---|---|---|---|---|
| | 0 | 1 | 2 | 4 | 24 |
| +5 ± 3° C. | NA | NA | NA | NA | X |
| Room Temperature | X | X | X | X | NA |

Some samples of the ones described above, were selected to be tested by surface plasmon resonance (Table 37). The aim was to verify if the high pH treatment had an impact on the binding affinities of BEAT®2 molecule to its targets CD3ε 1-26-Fc and CD38 and thus, indirectly, on its activity. In addition, cell based functional assay were also performed to directly verify the impact of high pH on BEAT®2 molecule activity.

TABLE 37

Samples tested for binding affinity and cell based functional assays

| Incubation time (h) | Time points | | |
|---|---|---|---|
| | 0 | 1 | 2 |
| +5 ± 3° C. | X | NA | NA |
| Room Temperature | | X | X |

Results and Conclusions

Figure 10:
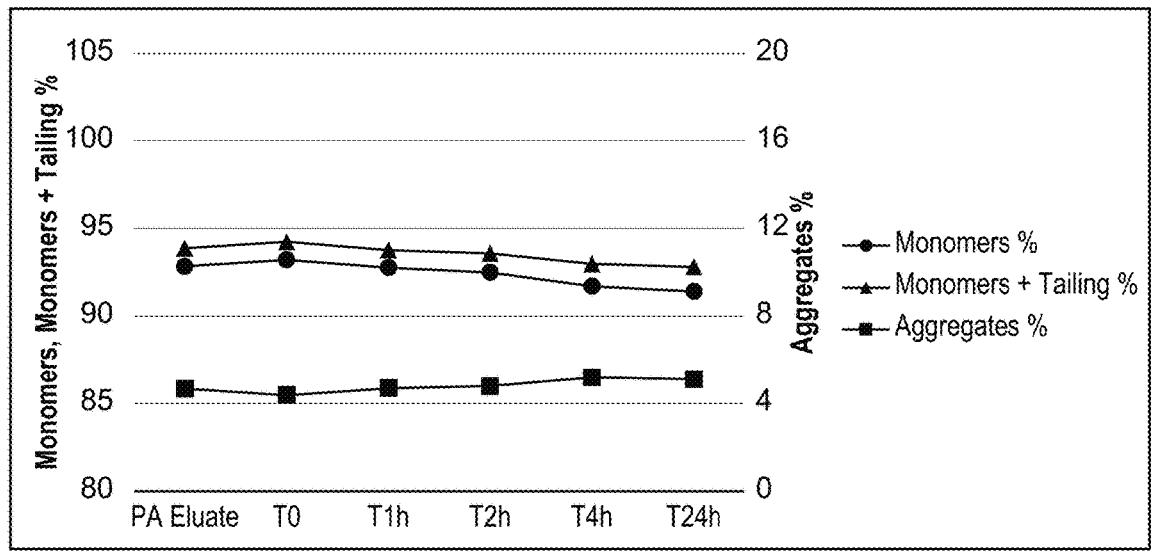
Figure 10:
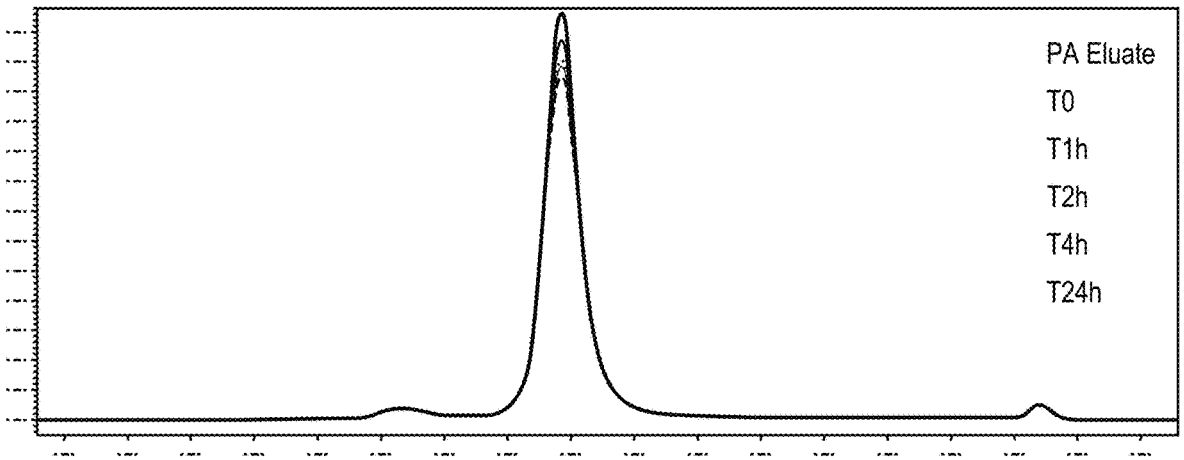
Figure 10:
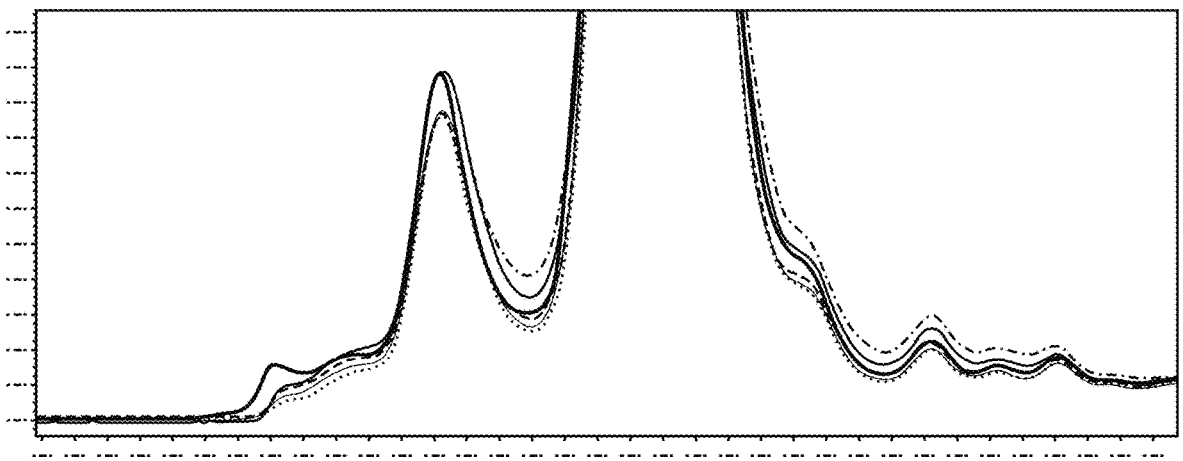

The impact of hold time at high pH on BEAT®2 has been analysed by SE-HPLC to establish the purity of the sample following the incubation at different time points as shown in Table 38 and FIG. 10.

TABLE 38

HPLC-SE results

| Intermediate | | PA Eluate | VI Neutralized | | | | |
|---|---|---|---|---|---|---|---|
| Time point | | PA Eluate | t0 | t1 h | t2 h | t4 h | t24 h |
| HPLC-SE | Aggregates % | 4.7 | 4.4 | 4.7 | 4.8 | 5.2 | 5.1 |
| | Monomers % | 92.9 | 93.2 | 92.8 | 92.5 | 91.7 | 91.4 |
| | Monomers + Tailing % | 93.9 | 94.2 | 93.8 | 93.6 | 93.0 | 92.8 |

As shown in Table 38, the monomers percentage was comparable between conditions, and no significant aggregation appears with high pH treatment up to 24 hours, in fact the observed variations fall within the method variability.

These results suggest that BEAT®2 is stable up to 24 hours covering with a safety margin the process time which is usually ≥60-≤90 minutes.

Figure 11:
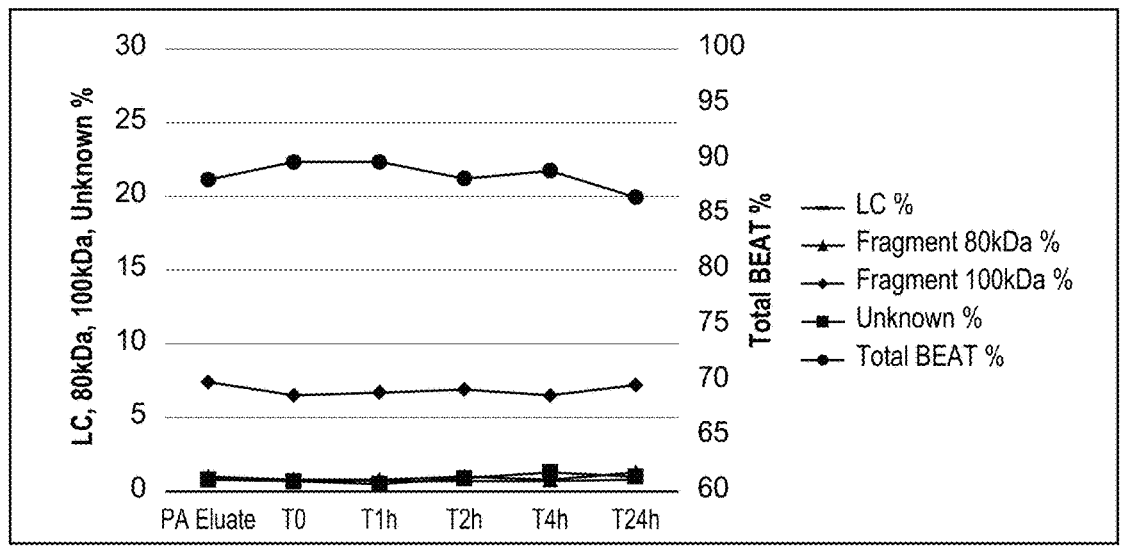
Figure 11:
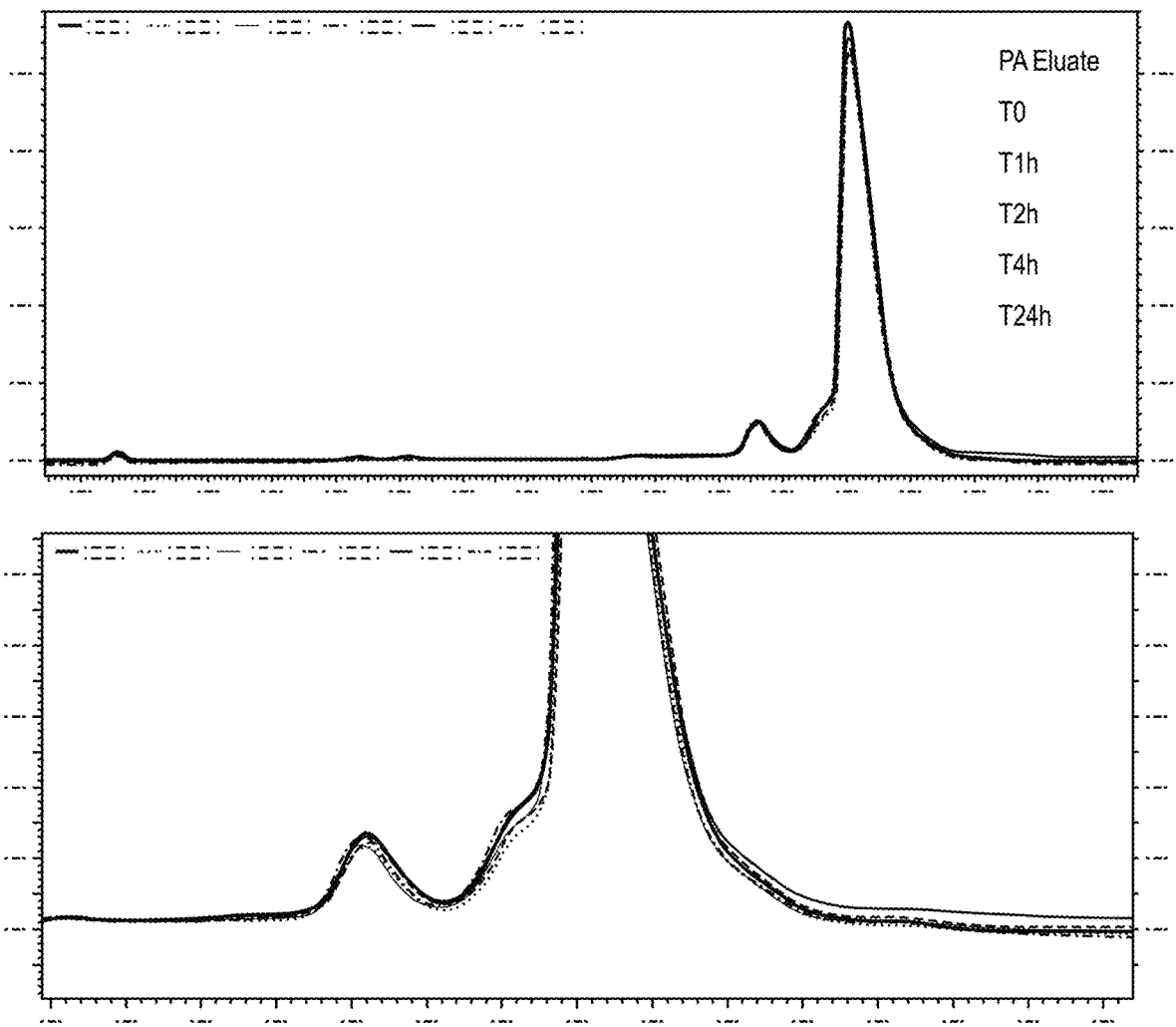

Additionally, non-reduced CGE has been run, further confirming the stability of BEAT® 2, as shown in Table 39 and FIG. 11.

TABLE 39 non-reduced CGE results

| Intermediate | | PA Eluate | VI Neutralized | | | | |
|---|---|---|---|---|---|---|---|
| Time point | | PA Eluate | t0 | t1 h | t2 h | t4 h | t24 h |
| CGE non-reduced | LC % | 0.9 | 0.8 | 0.7 | 0.7 | 0.7 | 0.8 |
| | Fragment 80 kDa % | 1.0 | 0.8 | 0.8 | 1.0 | 0.8 | 1.3 |

TABLE 39-continued non-reduced CGE results

| Intermediate | PA Eluate | VI Neutralized | | | | |
|---|---|---|---|---|---|---|
| Time point | PA Eluate | t0 | t1 h | t2 h | t4 h | t24 h |
| Fragment 100 kDa % | 7.4 | 6.5 | 6.7 | 6.9 | 6.5 | 7.2 |
| Total BEAT % | 88.2 | 89.8 | 89.8 | 88.3 | 89.0 | 86.6 |
| Unknown % | 0.8 | 0.7 | 0.5 | 0.9 | 1.3 | 1.0 |

BEAT % is comparable to reference sample (PA Eluate) and no significant fragmentation is showed until 4 hours. BEAT®2 is stable up to 2 hours covering with a safety margin the process time which is usually ≥60-≤90 minutes.

Figure 12:
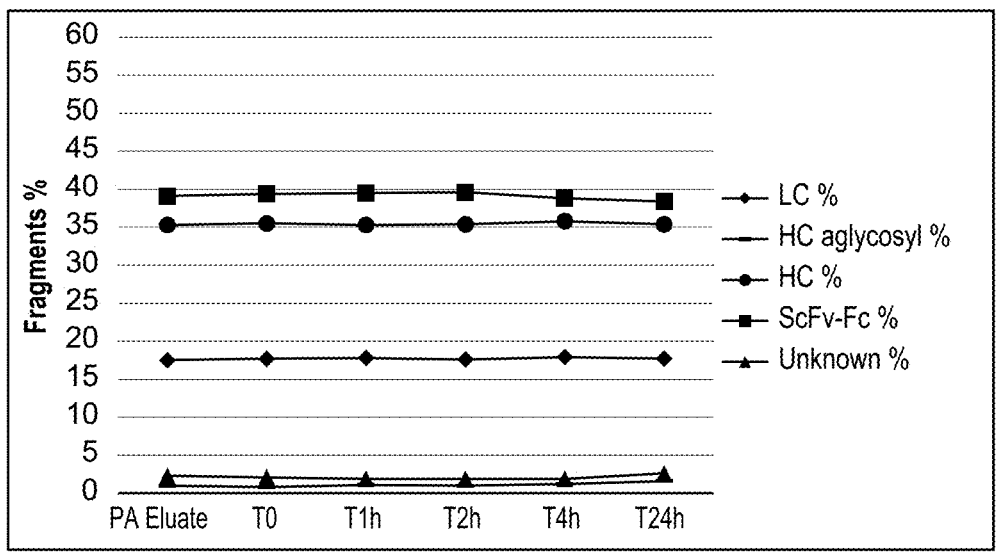
Figure 12:
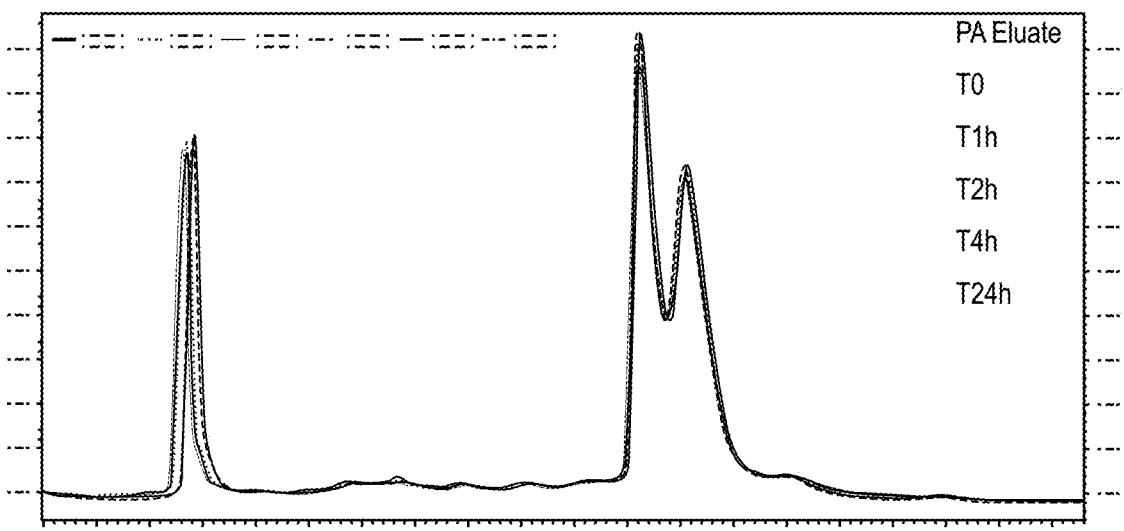
Figure 12:
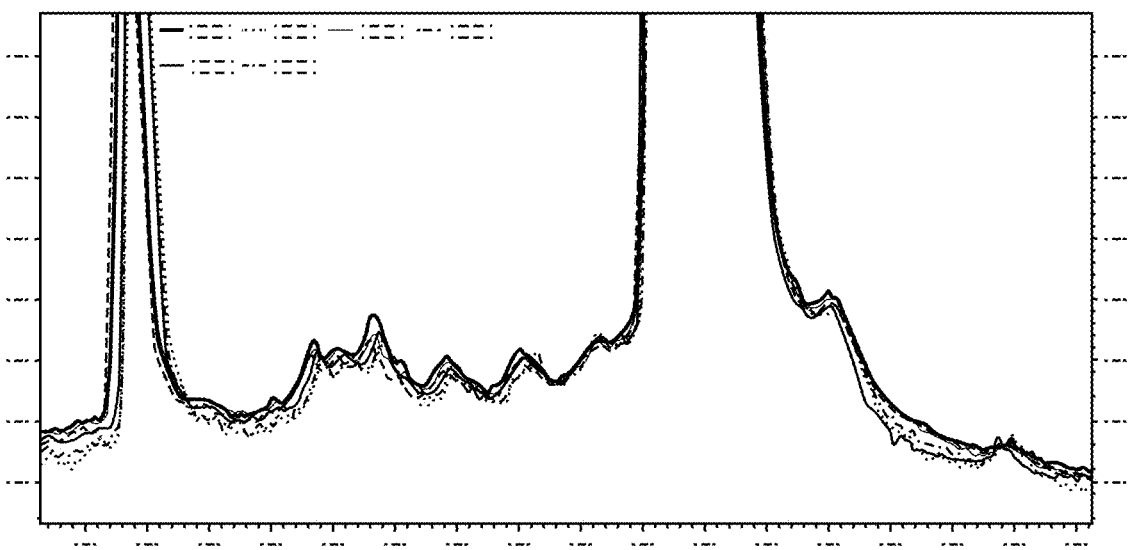

Furthermore, reduced CGE shows that BEAT®2 is stable up to 24 hours covering with a safety margin the process time which is usually ≥60-≤90 minutes (see Table 40 and FIG. 12).

TABLE 40

Reduced CGE results

| Intermediate | | PA Eluate | VI Neutralized | | | | |
|---|---|---|---|---|---|---|---|
| Time point | | PA Eluate | t0 | t1 h | t2 h | t4 h | t24 h |
| CGE reduced | LC % | 17.5 | 17.7 | 17.8 | 17.6 | 17.9 | 17.7 |
| | HC aglycosyl % | 1.0 | 0.8 | 1.1 | 1.0 | 1.2 | 1.6 |
| | HC % | 35.3 | 35.5 | 35.3 | 35.4 | 35.8 | 35.4 |
| | ScFv-Fc % | 39.1 | 39.4 | 39.5 | 39.6 | 38.8 | 38.4 |
| | Unknown % | 2.3 | 2.1 | 1.9 | 1.9 | 1.9 | 2.6 |

To evaluate variations on charge variants, iCE was performed (FIG. 13 and Table 41).

TABLE 41

Results iCE

| Intermediate Time point | | PA Eluate | VI Neutralized | | | | |
|---|---|---|---|---|---|---|---|
| | | PA Eluate | t0 | t1 h | t2 h | t4 h | t24 h |
| ICE | Acidic % | 67.0 | 67.0 | 68.0 | 70.0 | 72.6 | 76.2 |
| | Main % | 33.0 | 33.0 | 32.0 | 30.0 | 27.4 | 23.8 |

An increase of acidic species is observed overtime. Nevertheless, the method variability is ≤10%, therefore the differences observed until 2 hours are within method variability and could be considered as acceptable and statistically not significant. The acidic % increase observed is an expected trend but the 2 hours safety margin are covering the process time (and above) which is usually ≥60-≤90 minutes.

Figure 14:
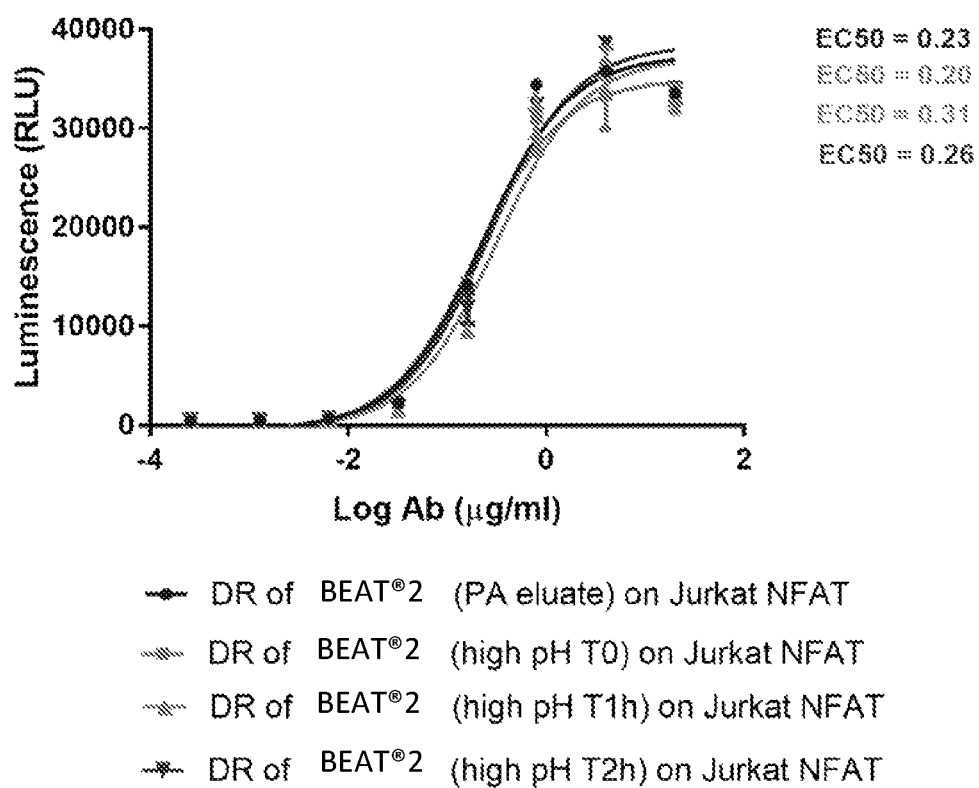

Cell based functional assay results are presented in FIG. 14 and in Table 42. The half maximal effective concentration (EC50) were determined based on the dose-response curves. The EC50 values obtained allowed to determine the relative potency of each sample tacking as reference the sample with high pH incubation time equal to zero.

TABLE 42

Relative potencies according to high pH treatment duration.

| | Relative potency (%) |
|---|---|
| BEAT ®2 PA Eluate (reference) | 100 |
| BEAT ®2 t0 | 114 |
| BEAT ®2 t1 h | 71.7 |
| BEAT ®2 t2 h | 88.5 |

No tendency is observed overtime in relative potency values. High pH treatment at t1 h and t2 h give highly similar potency compared to PA Eluate used as reference. Given the method variability ≤25%, high pH treatment does not significantly alter BEAT®2 functionality even after 2 hours of incubation, covering the process time which is usually ≥60-≤90 minutes.

The binding affinities of BEAT®2 antibody to its targets CD3 and CD38, evaluated at different time points, are listed in Table 43.

TABLE 43

Relative affinities of BEAT ®2 to its targets

| Sample | Affinity measurement | Mean KD (nM) | StdDev (nM) | % CV | Relative KD (% RS) |
|---|---|---|---|---|---|
| PA eluate | human CD3ε 1-26 Nterm | 42.2 | 2.14 | 5.1 | 100 |
| t0 | human CD3ε 1-26 Nterm | 28.5 | 0.85 | 3.0 | 68 |
| t1 | human CD3ε 1-26 Nterm | 39.1 | 0.76 | 2.0 | 93 |
| t2 | human CD3ε 1-26 Nterm | 41.1 | 0.52 | 1.3 | 97 |
| PA eluate | human CD38 | 0.483 | 0.006 | 1.2 | 100 |
| t0 | human CD38 | 0.504 | 0.013 | 2.7 | 104 |
| t1 | human CD38 | 0.547 | 0.008 | 1.4 | 113 |
| t2 | human CD38 | 0.485 | 0.019 | 3.9 | 100 |

No difference in binding activity to human CD38 is observed between the protein A eluate and all samples incubated at high pH. Also, no difference of functional significance in binding activity to human CD3ε is observed between the protein A eluate and all samples incubated at high pH. A small difference in affinity to human CD3ε was observed between t0 sample and all other samples, but the affinity is still in the same range (low nanomolar, 32% higher than PA eluate) and is probably due to small difference in concentrations injected.

In conclusion, high pH incubation does not have an impact on the stability and activity of BEAT®2 and can be used in the manufacturing process of BEAT® 2.

EXAMPLE 7: HIGH pH TREATMENT OF PA ELUATE IS AN EFFICIENT INACTIVATION STEP IN THE PURIFICATION PROCESS OF THE LOW pH-LIABLE ANTIBODY BEAT®3

In order to assess the most appropriate viral inactivation method for a third BEAT antibody, BEAT® 3, stability, activity and VRV studies have been performed to investigate the effect of low and high pH treatment of PA eluate as well as solvent/detergent treatment of clarified harvest.

Materials, Methods and Equipment

The starting materials used in this study were clarified harvest and PA eluate after affinity chromatography using the KanCapA resin from Kaneka.

Cell cultures were typically terminated when viability was lower than 80% and cells' debris were removed by dead-end depth filtration followed by a filtration on a 0.2 µm filter. The cell culture supernatants were from CHO cells. Initial development testing were performed using non-representative material coming from a parental clone of the final selected clone. Late assays of the development were performed using a representative material, coming from the final selected clone.

In-process 0.2 µm filtration steps were typically performed for all buffers and process intermediates. For VI studies, only magnetic stirrer, pH and conductivity meter were used.

PA Eluate—Low pH Viral Inactivation

About 25 mL of PA eluate was acidified to pH 3.7 in a 50 mL TPP tube using HCl 3.7%. The product at low pH was incubated under agitation using magnetic stirrer except for time point t0 which was immediately neutralized as described below. The time points tested were 1 hour, 2 hours, 4 hours and 6 hours at RT and beyond this point, the product was put at 5±3° C. up to 24 and 48 hours of incubation. At each time point, about 3 mL of low pH product was transferred into a 15 mL TPP tube and neutralized by increasing pH up to pH 5.0 using 250 mM Histidine pH 12.0 (neutralization step) in order to stop the VI reaction, before being frozen.

High throughput HPLC-SE analysis was used to characterize all time points. Caliper CGE (non-reduced) and iCE analysis were only performed on t0 and T48 hours. The results were analysed by comparing the different time point to time point t0 (sample incubated at low pH and immediately neutralized at pH 5.0). PA eluate not neutralized and without any VI treatment was also analysed and used as reference to be compared with t0.

TABLE 44

Low pH testing conditions

| | Time points | | | | | | |
|---|---|---|---|---|---|---|---|
| Incubation time (h) | 0 | 1 | 2 | 4 | 6 | 24 | 48 |
| +5 ± 3° C. | X | NA | NA | NA | NA | X | X |
| Room Temperature | | X | X | X | X | NA | NA |

Clarified Harvest—Solvent-Detergent Treatment

A mix of 0.3% TnBP and 1% Tween 80 was prepared and agitated 15 minutes prior to incubation in order to ensure mixture homogeneity. The mix was incubated and mixed with clarified harvest using a magnetic stirrer during minimum 60 minutes before the PA loading step in order to have a sufficient viral inactivation as observed on previous project. The material treated was immediately purified in order to stop the VI reaction using a 1.1 cm diameter column of Kaneka KanCap A resin. The PA eluate, kept at 5±3° C., was subsequently analyzed by HPLC-SE, CGE (reduced and non-reduced) and iCE.

PA Eluate—High pH Viral Inactivation

The time points tested were 1 hour, 2 hours, 4 hours and 6 hours at RT and beyond this point, the product was put at 5±3° C. up to 24 and 48 hours of incubation. About 25 mL of PA eluate was basified to pH 11.2 in a 50 mL TPP tube using NaOH 0.5 M. This pH was selected as a worst case scenario for product quality, in order to validate the target pH 11.0 of the process. The product at high pH was incubated under agitation using magnetic stirrer except for time point t0 which was immediately neutralized as described below. At each time point, about 3 mL of high pH product was transferred into a 15 mL TPP tube and neutralized by decreasing the pH up to pH 6.0 using HCl 3.7% (neutralization step) in order to stop the VI reaction, before being frozen.

The product quality was analysed by HPLC-SE, iCE and CGE for all time points. The analytical results were analysed by comparing the different time point to time point t0 (sample incubated at high pH and immediately neutralized at pH6.0). PA eluate not neutralized and without any VI treatment was also analysed and used as reference to be compared with to.

TABLE 45

High pH testing conditions

| Incubation time (h) | Time points | | | | | | |
|---|---|---|---|---|---|---|---|
|  | 0 | 1 | 2 | 4 | 6 | 24 | 48 |
| +5 ± 3° C. | X | NA | NA | NA | NA | X | X |
| Room Temperature |  | X | X | X | X | NA | NA |

Binding Affinity Assays

Some samples from high pH treatment development runs (see Table 46), were selected to be tested by surface plasmon resonance. The aim was to verify if the high pH treatment had an impact on the binding affinities of BEAT®3 molecule to its targets CD3ε 1-26-Fc and EGFR and thus, indirectly, on its activity.

The first assay, aims to determine the binding affinity to human CD3ε 1-26-Fc antigen. It was performed with a Series S Sensor Chip CM5 (GE Healthcare). The human CD3ε 1-26-Fc was prepared at a concentration of 25 nM in Acetate pH 4.5 buffer. BEAT®3 samples were prepared from 1000 nM to 1.37 nM, in final volumes of 200 µl per dilution. The run was performed using a Biacore T200 processing unit (GE Healthcare).

The second assay, aims to determine the binding affinity to Human EGFR-his antigen. It was performed with a Serie S Sensor Chip Protein G (GE Healthcare). BEAT®3 samples were diluted at 25 nM each in HBS-EP+ (GE Healthcare) buffer. EGFR were prepared from 100 nM to 0.13 nM, in final volumes of 250 µl per dilution were realized.

TABLE 46

Samples tested for binding affinity assays

| Incubation time (h) | Time points | | | |
|---|---|---|---|---|
|  | 0 | 2 | 4 | 24 |
| +5 ± 3° C. | X | NA | NA | X |
| Room Temperature |  | X | X | NA |

Cell Based Functional Assays

The aim of the cell based functional assay was to verify if the high pH treatment had an impact on the BEAT®3 molecule activity. Selected samples from high pH treatment development were tested as described in Table 47:

TABLE 47

Samples tested for cell based functional assays

| Incubation time (h) | Time points | | | |
|---|---|---|---|---|
|  | 0 | 2 | 4 | 24 |
| +5 ± 3° C. | X | NA | NA | X |
| Room Temperature |  | X | X | NA |

The cell based potency assay used an engineered Jurkat T cell line commercially available at Promega. These cells were stably transfected with a reporter construct in which the luciferase cDNA sequence was under the control of an NFAT response element (RE). The production of luciferase was directly dependent upon signals which activate the NFAT transcription factor, such as signals derived from the CD3ε (and T cell receptor complex). The assay was setup by co-incubating the Jurkat-NFAT cells (responder cells) (CD3ε+, EGFR−) with SK-BR-3 target cells (EGFR+ CD3ε−) and BEAT®3 or control antibodies. The activation of the responder cells was quantified by the luminescence response. Jurkat NFAT cell line had 6 weeks of culture (P6) and SK-BR-3 cell line had 3 weeks of culture (P3).

The assay was performed in a 96 well ELISA plate U-bottom (TPP). SK-BR-3 expressing EGFR cell line (ATCC) were resuspended at $3 \times 10^5$ cells/ml and 100 µl was distributed in each well of the 96 well plate. The assay plate was incubated overnight at 37° C. and 5% $CO_2$. The day after, 25 µl of SK-BR-3 expressing EGFR cell line were kept in assays plate and 25 µl of the different BEAT®3 samples diluted at 6 µg/mL (2 µg/mL final) were transferred in different wells. Jurkat NFAT Cells (Promega) were resuspended at $1.2 \times 10^6$ cells/ml and 25 µl was distributed in each well of the assay plate. The plate was covered and incubate 5 h at 37° C., 5% $CO_2$. At the end of the incubation, 75 µl of Bio-Glo™ Luciferase Assay Substrate (Promega) were added to the wells and the plate were acquired in a microplate reader. Luminescence was measured using the following settings: read tape—endpoint; integration time—1 minute; emission—hole; optics position—top; gain 135; read height—1.00 mm. Data were then plotted and analyzed using Prism (GraphPad) software. A non-linear regression fitting was applied after X=Log(X) transformation and sigmoidal dose-response fitting was applied to all data-sets to determine the $EC_{50}$ values. The relative potency for each sample was calculated using the following calculation: Relative potency %=EC50reference/EC50sample×100.

Residual DNA and HCP Assays

The main objective of a VI step is to efficiency inactivate viruses while ensuring product quality. Nevertheless, in a downstream process, each step can have an impact on impurities levels. The aim of the assays described below was to assess the impact of the high pH treatment on the residual DNA and HCP levels from CHO cells.

For HCP quantification, two different assays were used: a 3G HCP Elisa kit from Cygnus technologies and an Anti-CHO HCP Detection Kit from ForteBio-Cygnus with the use of Octet Red 96 instrument from Pall ForteBio for data processing. Both techniques were used firstly to assess HCP removal by High pH treatment and also, to compare both techniques, namely high throughput octet known to be more sensitive, and ELISA.

Sample preparation for ELISA was performed with 3G Elisa HCP kit (Cygnus technologies) and using a 1/100 dilution. The samples were reacted with an affinity purified horseradish peroxidase labelled antibody, in microtiter wells coated with an anti-CHO HCP capture antibody. Following wash, the substrate tetramethyl benzidine (TMB) was reacted. The amount of hydrolysed substrate was directly proportional to the concentration of CHO proteins present. The quantification was achieved by comparing the signal of samples to HCP standards assayed at the same time. Data were processed using PRISM software.

Regarding Octet, two sample dilutions were tested (1/200 and 1/400) using the Anti-CHO HCP Detection Kit (ForteBio-Cygnus). The measurement involved a sandwich-type assay on the Anti-CHO HCP Biosensor which was pre-coated with the gold-standard 3G Anti-CHO HCP antibody from Cygnus Technologies. The 96 well plate prepared was directly read with Octet Red 96 instrument from Pall ForteBio. Data were processed through Octet system data acquisition software.

Regarding the quantification of residual DNA, the assays involved a treatment of samples by a proteinase K to remove proteins. Then, DNA is extracted using magnetic beads, wash and finally elute. After that, DNA is quantified by real-time PCR (polymerase Chain reaction) using Fast 5000 PCR equipment (Applied Biosystem). Samples preparation were performed with resDNASEQ™ Quantitative CHO DNA kit V3.0 (Applied Biosystems).

Some samples coming from high pH development, listed in Table 48, were selected to be tested by residual DNA and HCP assays described above. 0.2 μm filtration after VI was also tested.

TABLE 48

Samples tested for residual DNA and HCP assays

| Testing material | Production scale | Viral inactivation | VI incubation time | 0.2 μm filtrated material after VI |
|---|---|---|---|---|
| PA eluate | Pilot | — | — | — |
| VI neutralized | | High pH | 90 min | No |
| VI neutralized | | High pH | 90 min | Yes |

All PA eluates were also filtrated at 0.2 μm before VI step.

VRV NRT Study

The data from VI experiments were analysed and the high pH treatment was selected for VRV NRT study regarding the product quality obtained. The purpose of this viral clearance study, performed by BioReliance, was to evaluate the ability of this treatment to effectively inactivate viruses. This study was performed on Xenotropic Murine leukaemia virus (MLV) which is a typical model virus used for biological products derived from CHO cell lines such as monoclonal antibody. MLV is also known to be sensitive to physico chemical treatment (see Table 49).

TABLE 49

MLV physico chemical characteristics

| Virus | Strain | Genome | Envelope | Family | Size (nm) | Resistance To Physical/ Chemical Reagents |
|---|---|---|---|---|---|---|
| MLV | pNFS Th-1 | ssRNA | Yes | Retro | 80-110 | Low |

A single run was performed at pH 10.8+/−0.05 which is a worst case of the process setpoint of pH11.0 (i.e. low limit of the pH range is supposed to inactivate less viruses). The temperature specification for high pH treatment was ≥20-≤25° C., nevertheless MLV was spiked at 16° C.±1° C. to have a worst case scenario data in the event of an Out Of Specification (OOS). A PA eluate from development runs was used as starting material. The pH was increased using 0.5 M NaOH and samples were incubated at high pH during different hold points described in Table 50, in order to follow a VI kinetic. To stop the reaction, samples were neutralized to pH 6.0-8.0 with 3.7% HCl.

TABLE 50

Samples conditions during VRV study

| | Time points | | | |
|---|---|---|---|---|
| Incubation time (min) | t0-1 | t10 | t30 | t60 |
| 16° C. ± 1° C. | X | X | X | X |

VRV Studies to Test High pH as a Step of the Purification Process of BEAT®3

Further, the ability of the different step of BEAT®3 purification process to inactivate or remove viruses was investigated in independent duplicate runs. Among these it was assessed the capacity of high pH treatment on the PA eluate. The experiments were performed at BioReliance. Log reduction factors is calculated with respect to the Neutralized Load sample; samples are drawn after different incubation time (t) points, 5, 10, 30, and 60 minutes and subsequently neutralized.

Results and Conclusions a. PA Eluate—Low pH Viral Inactivation

Figure 15:
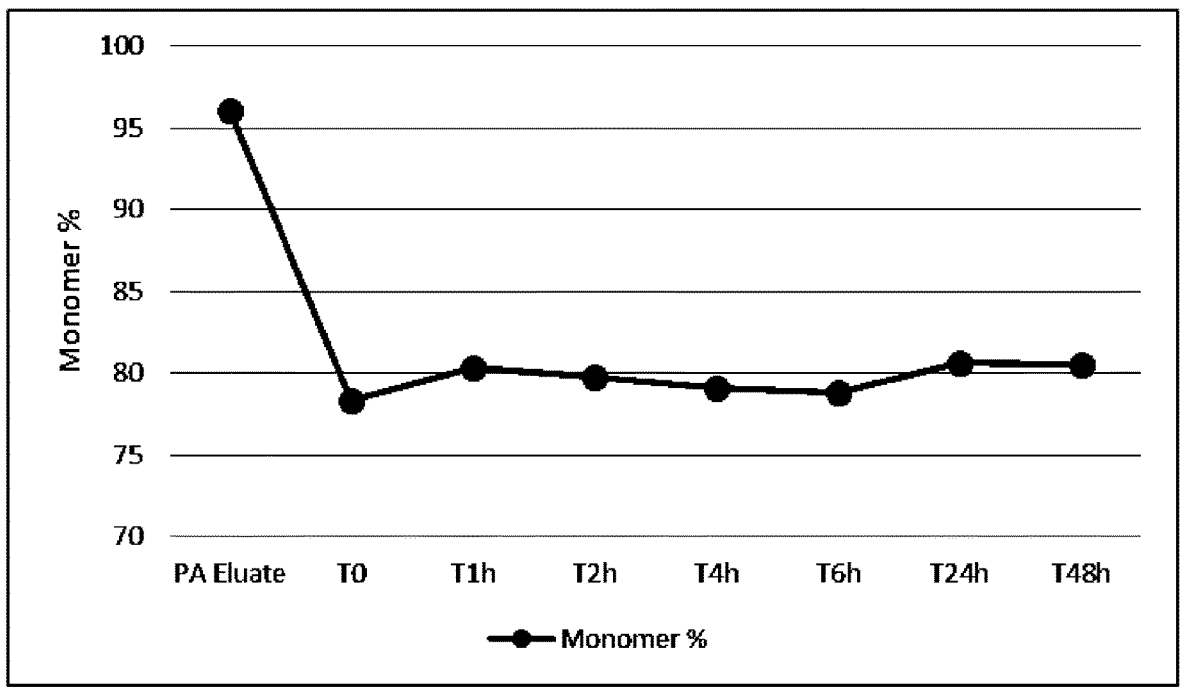
Figure 16:
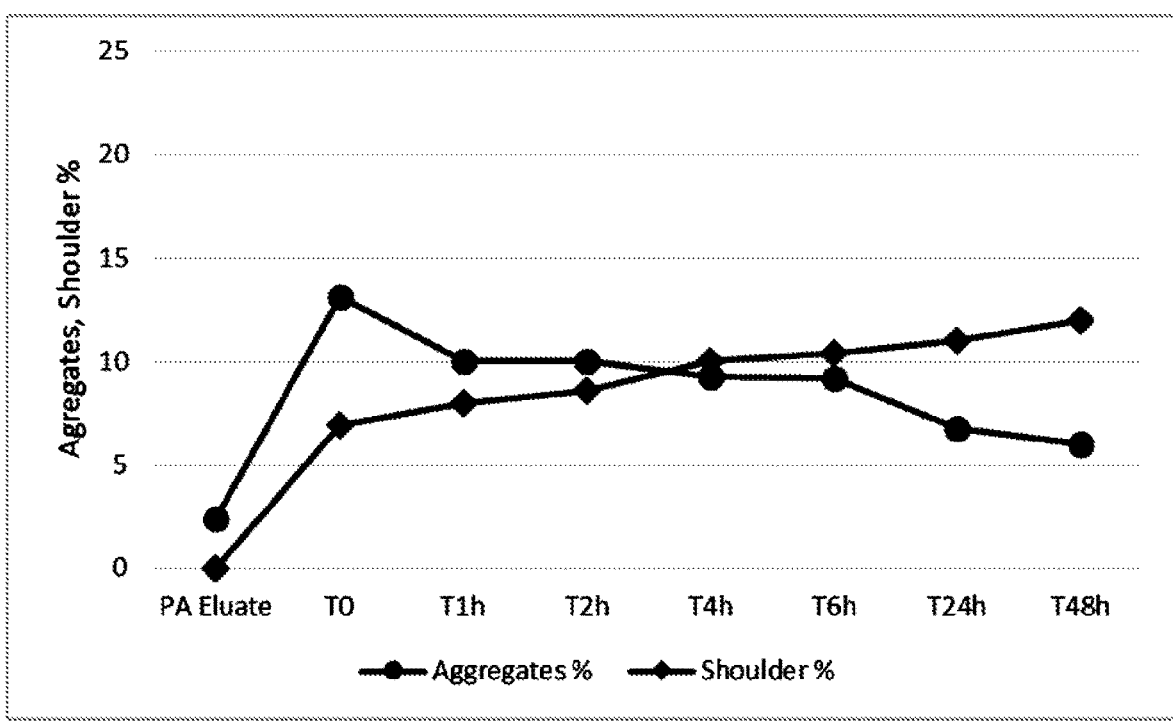

HPLC-SE results at the different time points tested are showed in Table 51 and illustrated in FIG. 15 and FIG. 16.

TABLE 51

HPLC-SE results for VI low pH

| Intermediate | | PA eluate | VI neutralized | | | | | | |
|---|---|---|---|---|---|---|---|---|---|
| Time Point | | NA | t0 | t1 h | t2 h | t4 h | t6 h | t24 h | t48 h |
| Temperature | | NA | NA | RT | RT | RT | RT | 5 ± 3° C. | 5 ± 3° C. |
| HPLC-SE | Aggregate % | 2.4 | 13.1 | 10.0 | 10.0 | 9.3 | 9.2 | 6.8 | 6.0 |
| | Shoulder % | 0.0 | 6.9 | 8.0 | 8.6 | 10.0 | 10.4 | 11.0 | 12.0 |
| | Monomer % | 96.1 | 78.3 | 80.3 | 79.8 | 79.1 | 78.8 | 80.6 | 80.5 |
| | Fragment % | 1.5 | 1.7 | 1.7 | 1.7 | 1.6 | 1.7 | 1.7 | 1.6 |

Figure 17:
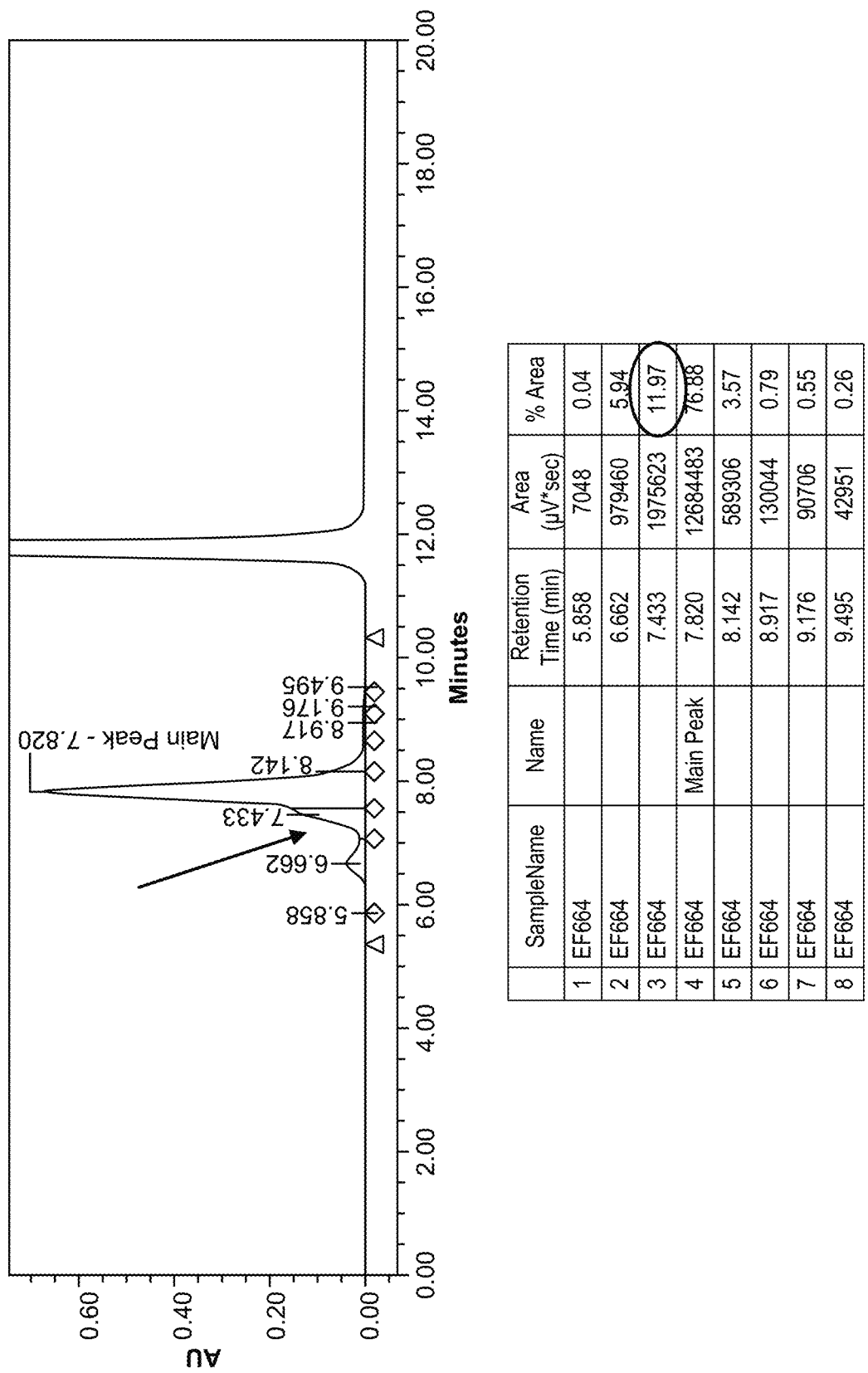

HPLC-SE results showed a significant decrease of monomer % for all samples treated at low pH including the time point t0, showing a high degradation of the product immediately after low pH incubation and neutralization. This degradation is directly related to aggregates and "shoulder" species increase. In fact, the low pH treatment impacted immediately aggregates percentage, increasing from 2.4% for PA Eluate to 13.1% for time point t0. Moreover, an increase of "shoulder" species was observed overtime ranging from 6.9% for t0 to 12.0% for T48 h. This "shoulder" species appeared in front of the main peak of monomer. In FIG. 17, one example of analytical HPLC-SE profile containing an important amount (12%) of "shoulder" species.

In addition, Caliper non-reduced results, allowing to identify and assess the percentage of different fragments, are listed in Table 52. In light of important and critical degradation observed in HPLC-SE results, only the time point t0 and t24 hours were analysed.

TABLE 52

Caliper non-reduced results for Low pH VI

| Intermediate | | PA Eluate | VI neutralized | |
|---|---|---|---|---|
| Time point | | N/A | t0 | t48 h |
| Temperature | | NA | NA | 5 ± 3° C. |
| Caliper CGE | LC % | 0.4 | 0.4 | 0.4 |
| | Unknown fragments % | 2.0 | 1.6 | 1.7 |
| | 100 kDa fragments % | 4.0 | 3.6 | 3.7 |
| | BEAT' % | 3.1 | 12.4 | 3.8 |
| | BEAT % | 88.2 | 80.1 | 88.9 |
| | BEAT" % | 1.9 | 1.5 | 1.2 |
| | Total BEAT % | 93.2 | 94.0 | 93.9 |
| | Aggregates % | 0.5 | 0.3 | 0.3 |

The low pH incubation showed a fragmentation of the product leading to an increase of BEAT' % from 3.1% in PA Eluate to 12.4% for VI neutralized at t0. These CGE data seem to correlate with HPLC-SE data discussed above where the "shoulder species" observed in HPLC-SE could be equivalent to BEAT' species. Nevertheless, the time point at 48 hours showed a percentage of BEAT' lower than t0, at about 3.8%. This result was surprising and not consistent. This data could be explain by the analytical method employed. In fact, after discussion with analytical development group, Caliper CGE could be considered only as a screening method where detection and quantitation are not accurate enough or even comparable to CGE. For information, the analysis profiles for t0 and t24 h are presented in FIG. 18 and FIG. 19. Any definitive conclusion was able to be made with these results and Caliper analysis was definitively replaced by classic CGE for the pursuit of the VI step development.

The charge variants results by ICE3 analysis are described in Table 53. As for Caliper analysis, only the time point t0 and t24 hours were analysed.

TABLE 53

ICE3 results for Low pH VI

| Intermediate | | PA Eluate | VI neutralized | |
|---|---|---|---|---|
| Time point | | NA | t0 | t48 h |
| Temperature | | NA | NA | 5 ± 3° C. |
| ICE | Acidic % | 50.0 | 48.7 | 49.4 |
| | Main % | 41.2 | 42.3 | 41.2 |
| | Basic % | 8.8 | 9.0 | 9.3 |

No variation on charge variants percentage was observed after low pH treatment. The percentage of acidic species stayed at about 49-50%, basic species at about 9% and main peak at about 41%. The low pH treatment had no impact on charge variants of the BEAT®3 molecule until 48 hours of incubation.

To conclude, the low pH VI strategy was definitively invalidate as a suitable alternative for VI process in light of high product degradation observed in HPLC-SE data.

b. Clarified Harvest—Solvent/Detergent Treatment

S/D treatment of clarified harvest was performed twice, using representative material. The S/D treatment was followed by PA step to stop the reaction and the product quality was verified directly in the resulting PA eluates. They were compared with 2 reference runs witch were not previously treated by S/D, coming from PA step development. These two reference runs were performed with the same starting material and at comparable loading factors. Only the pH of elution buffer was different, pH 4.3 and pH 4.25 for reference and S/D runs respectively.

Table 54 shows a summary of the data obtained on these runs:

TABLE 54

PA step with clarified harvest + S/D, process parameters, recoveries and product quality results

| | | | | Reference 1 | Reference 2 |
|---|---|---|---|---|---|
| | Run number | 1 | 2 | 1 | 2 |
| Clarified Harvest (+S/D) | PA titer [g/L] | 0.9 | 0.9 | 0.9 | 0.9 |
| | pH (20-25° C.) | 7.1 | 7.1 | 7.0 | 7.0 |
| | Conductivity [mS/cm] (24-26° C.) | 15.1 | 15.1 | 14.9 | 14.9 |
| | Tween 80 concentration [%] | 1.1 | 1.1 | | |
| | TnBP concentration [%] | 0.3 | 0.3 | | |
| | S/D incubation duration [min] | 61.0 | 65.0 | | |
| | Loading factor [g/L] | 10.0 | 34.0 | 10 | 29 |
| PA Eluate | pH (20-25° C.) | 4.3 | 4.4 | 4.4 | 4.4 |
| | Conductivity [mS/cm] (24-26° C.) | 1.3 | 1.6 | 1.4 | 1.6 |
| | Volume [CV] | 3.8 | 4.2 | 5.1 | 5.2 |
| | Concentration [g/L] | 1.5 | 5.5 | 1.1 | 3.7 |
| | Tween 80 concentration [%] | 0.001 | 0.001 | | |
| | TnBP concentration [mg/L] | <1 | <1 | | |
| HPLC-SE | Aggregates % | 1.4 | 4.3 | 0.8 | 2.6 |
| | Monomer % | 98.0 | 94.9 | 99.2 | 96.9 |
| | Fragments % | 0.6 | 0.9 | 0.0 | 0.5 |
| NR CGE | LC % | 0.7 | 0.6 | 0.6 | 0.6 |
| | Fc % | 0.1 | 0.2 | 0.1 | 0.2 |
| | HC-ScFv % | 1.4 | 0.7 | 0.2 | 0.5 |
| | Unknown fragments % | 0.1 | 0.0 | 0.2 | 0.1 |
| | 100 kDa fragments % | 2.7 | 3.1 | 3.2 | 2.7 |
| | BEAT' % | 2.6 | 2.7 | 2.5 | 2.4 |
| | BEAT % | 87.5 | 87.8 | 88.6 | 91.0 |
| | BEAT" % | 4.3 | 4.6 | 4.5 | 2.3 |
| | Total BEAT % | 94.4 | 95.1 | 95.6 | 95.7 |
| R CGE | LC % | 17.3 | 17.5 | 17.7 | 17.5 |
| | Fc % | 23.1 | 23.3 | 22.7 | 22.5 |
| | HC-ScFv % | 51.7 | 51.8 | 53.2 | 53.5 |
| | Unknown after HC-ScFv % | 3.6 | 3.1 | 3.6 | 3.4 |
| iCE | Acidic [%] | 54.2 | 52.4 | 47.9 | 50.3 |
| | Main [%] | 37.8 | 39.8 | 38.6 | 38.3 |
| | Basic [%] | 8.0 | 7.7 | 13.6 | 11.0 |
| Step recovery [%] | | 58 | 67 | 58 | 66 |

Runs 1 and 2 corresponding to runs previously treated with S/D, were respectively performed at minimum and maximum loading factor (i.e. 10 and 34 g/L). This difference had an impact on step recoveries with 58% and 67% for respectively minimum and maximal loading factor. These results were comparable to those of reference runs without S/D.

Regarding quality, HPLC-SE analysis showed a monomer % for PA eluate varying between 94.9% and 99.2% and related to aggregates percentage ranging from 0.8% to 4.3%. The percentage of fragment remained below 1% for all runs. The variation of monomers and aggregates percentage was directly related to PA eluate concentrations. In fact, higher was the concentration and higher was the percentage of aggregates. Nevertheless, the monomer percentage was still acceptable with values beyond 95%. In addition, regarding reduced CGE results, no difference was observed between runs (e.g. Total BEAT % between 94.4% and 95.7% for all runs) and no fragmentation of the product appeared due to S/D use. Finally, the charge variants profiles showed a main peak percentage between 37.8% and 39.8% and any apparition of acidic or basic species was observed. No degradation of the product occurred after S/D treatment.

Furthermore, Tween 80 and TnBP concentrations were measured before and after PA step in order to evaluate the capacity of PA step to remove S/D. The Tween 80 concentration in the harvest was 1.1% (w/w) against 0.001% (w/w) in PA eluate and the TnBP measured was 0.3% (w/w) in harvest and 1 mg/L in PA eluate (which correspond at about 0.01% (w/w)). Consequently, the Protein A step efficiently removed S/D.

In conclusion, the S/D treatment before the PA step was a suitable option for the BEAT®3 viral inactivation.

c. PA Eluate—High pH Viral Inactivation

Small Scale Development

The product quality data obtained at small scale for the high pH treatment are presented in this section. HPLC-SE results are summarized in Table 55 followed by the CGE non-reduced and the charge variants results respectively in Table 56 and Table 57.

TABLE 55

| | | HPLC-SE results for High pH treatment | | | | | | |
|---|---|---|---|---|---|---|---|---|
| | Intermediate | PA Eluate | VI Neutralized | | | | | |
| | Time point | NA | t0 | t1 h | t2 h | t4 h | t6 h | t24 h | t48 h |
| | Temperature | NA | NA | RT | RT | RT | RT | 5 ± 3° C. | 5 ± 3° C. |
| HPLC-SE | Aggregates % | 2.4 | 3.7 | 3.5 | 3.6 | 3.3 | 3.3 | 3.2 | 3.2 |
| | Monomers % | 96.1 | 95.0 | 94.8 | 94.6 | 94.9 | 94.9 | 94.9 | 94.9 |
| | Fragments % | 1.5 | 1.3 | 1.7 | 1.8 | 1.8 | 1.9 | 1.9 | 2.0 |

The percentage of monomers was comparable between conditions (e.g. 95.0% for T0 and 94.9% for T48 h), and allowed to confirm that no aggregation occurred with high pH treatment up to 48 h of incubation. Nevertheless, there was 1% difference between the PA eluate sample and the high pH treated samples. This was due to a slight increase in aggregates % which could be the result of the high pH incubation. However, 1% difference is within method variability and is likely not statistically significant. Moreover samples were not stored the same way, PA eluate without treatment was stored at 5±3° C. and high pH treated samples were frozen, thus, leading to more reversible aggregate in the frozen samples.

Non reduced CGE results are shown in Table 56:

TABLE 56

| | | CGE non-reduced results for High pH VI | | | | | | |
|---|---|---|---|---|---|---|---|---|
| | Intermediate | VI Neutralized | | | | | | |
| | Time point | t0 | t1 h | t2 h | t4 h | t6 h | t24 h | t48 h |
| | Temperature | NA | RT | RT | RT | RT | 5 ± 3° C. | 5 ± 3° C. |
| CGE non-reduced | LC % | 0.5 | 0.5 | 0.5 | 0.7 | 0.5 | 0.6 | 0.5 |
| | Fc % | 0.3 | 0.6 | 0.6 | 0.7 | 0.6 | 0.7 | 1.1 |
| | HC-ScFv % | 1.3 | 1.3 | 1.2 | 1.1 | 1.4 | 1.1 | 1.3 |
| | Unknown fragments % | 0.1 | 0.2 | 0.2 | 0.4 | 0.3 | 0.4 | 0.5 |
| | 100 kDa fragments % | 2.3 | 2.1 | 2.2 | 2.2 | 2.4 | 2.1 | 2.4 |
| | BEAT' % | 3.0 | 2.8 | 2.7 | 2.9 | 3.0 | 2.6 | 3.0 |
| | BEAT % | 87.1 | 87.8 | 88.8 | 87.3 | 87.4 | 88.4 | 87.2 |
| | BEAT" % | 4.8 | 3.6 | 3.0 | 4.5 | 3.9 | 3.2 | 3.4 |
| | Total BEAT % | 94.9 | 94.2 | 94.5 | 94.7 | 94.3 | 94.2 | 93.6 |
| | Unknown species % | 0.0 | 0.8 | 0.0 | 0.0 | 0.0 | 0.4 | 0.6 |
| | Aggregates % | 0.4 | 0.3 | 0.7 | 0.4 | 0.5 | 0.6 | 0.2 |

The BEAT percentage given by CGE non-reduced remained the same for all samples tested in comparison to t0 (e.g. BEAT % was 87.1% at t0 and 87.2% at T48 h). Moreover, no fragment increase up to 48 h was able to be observed. These data were confirmed by the comparable CGE profile overlays illustrated in FIG. 20.

Charge variants by ICE3 results are showed in Table 57 below:

TABLE 57

| | | | | ICE3 results for high pH viral inactivation | | | | |
|---|---|---|---|---|---|---|---|---|
| Intermediate | | PA Eluate | | | VI Neutralized | | | |
| | Time point | NA | t0 | t1 h | t2 h | t4 h | t6 h | t24 h | t48 h |
| | Temperature | NA | NA | RT | RT | RT | RT | 5 ± 3° C. | 5 ± 3° C. |
| ICE | Acidic % | 50.0 | 49.2 | 50.2 | 50.9 | 54.0 | 54.1 | 56.6 | 59.6 |
| | Main % | 41.2 | 42.8 | 42.5 | 41.8 | 39.1 | 38.5 | 35.8 | 33.7 |
| | Basic % | 8.8 | 8.0 | 7.4 | 7.4 | 6.9 | 7.4 | 7.5 | 6.6 |

Figure 21:
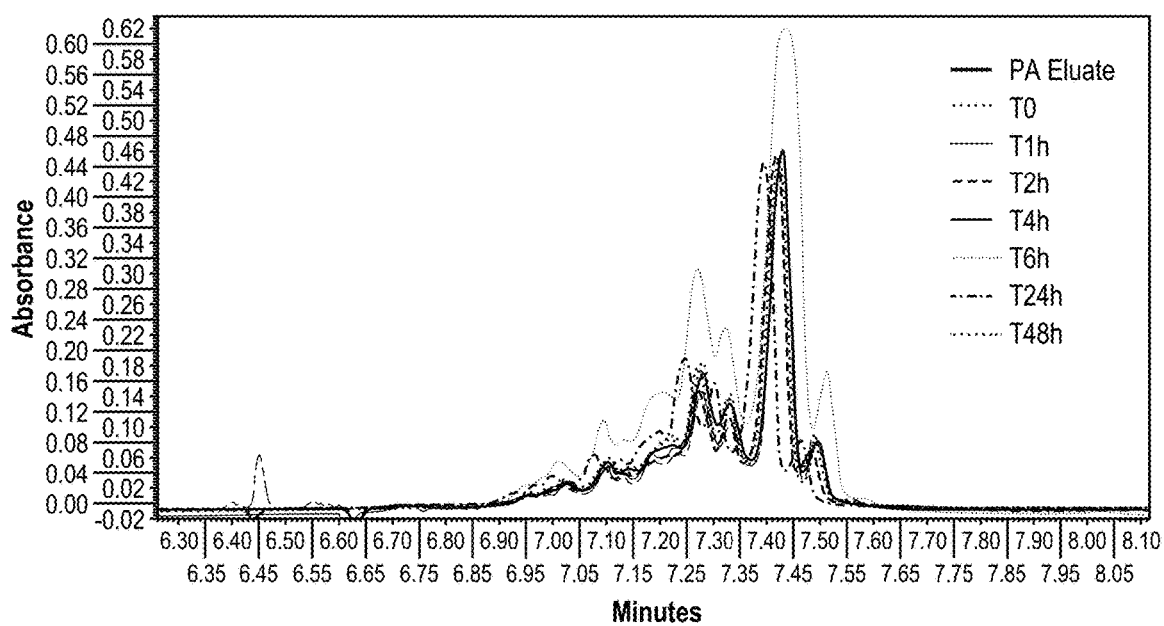

ICE3 results showed main peak % at about 42.8% for T0, 42.5% for 1 h and 41.8% for 2 h. Respectively for these same time point, the acidic % was at 49.2%, 50.2% and 50.9%. The charge variants are comparable up to 2 hours. After 2 hours of incubation, the acidic variant % are increasing, with 54.0% at 4 hours and 59.6% at 48 hours. Nevertheless, the method variability is 10% and the differences observed in main peak % for 4 hours and 6 hours could be statistically not significant with value within method variability (e.g. main peak at 42.8% at t0 and 39.1% at T4 h). However, the acidic % increase observed is an expected trend but the 2 hours safety margin are covering the process time (and above) which is usually ≥60-≤90 minutes. Profile overlays for each high pH incubation time point are illustrated in FIG. 21.

To conclude, data showed no impact of high pH treatment on product quality up to 2 hours. Going beyond 2 hours would not lead to any aggregation or fragmentation. However, a 7% increase of acidic species was observed after 24 hours and 10% after 48 hours. This provided confidence high pH incubation is a suitable alternative to low pH.

In light of data presented for S/D treatment and high pH above, high pH strategy was chosen as the preferred option. In fact, comparable product quality data were obtained for the two VI strategies. Nevertheless other parameters need to be taken into account as scalability, cost for industrialization, safety or viral clearance.

Scale Up Development

The process developed at small scale, was scaled up at pilot scale. These runs allowed to confirm the results determined previously and to generate process data at higher scale. The process parameters and the results for the two runs are described in Table 58.

TABLE 58

| | High pH pilot scale runs process parameters, recoveries and product stability results | | | |
|---|---|---|---|---|
| | Run | | 1 | 2 |
| | Protein A step loading factor [g/L] | | 11 | 22 |
| | PA eluate pH | | 4.3 | 4.4 |
| VI | VI pH after basification | | 11.2 | 11.2 |
| High pH | Ratio vol. base added/Volume [mL/L] | | 77.9 | 83.4 |
| VI | Ratio Vol. neut. added/Volume [mL/L] | | 4.1 | 5.6 |

TABLE 58-continued

| | High pH pilot scale runs process parameters, recoveries and product stability results | | | |
|---|---|---|---|---|
| | Run | | 1 | 2 |
| Neutralized | pH (20-25° C.) | | 6.0 | 6.1 |
| | Conductivity [mS/cm] (24-26° C.) | | 4.0 | 4.4 |
| | Concentration [g/L] | | 1.7 | 3.3 |
| | High pH incubation duration [min] | | 108 | 94 |
| | Total VI duration [min] | | 146 | 139 |
| | HPLC-SE | Aggregates % | 5.1 | 5.0 |
| | | Monomer % | 94.3 | 94.3 |
| | | Fragments % | 0.7 | 0.7 |
| | NR CGE | LC % | 0.7 | 0.8 |
| | | HC-ScFv % | 0.2 | 0.2 |
| | | 100 kDa fragments % | 3.0 | 3.3 |
| | | Beat' % | 2.3 | 2.2 |
| | | Beat % | 89.9 | 87.6 |
| | | Beat" % | 2.8 | 4.1 |
| | | Total BEAT % | 95.0 | 93.9 |
| | | Unknown fragments % | 1.0 | 1.7 |
| | ICE | Acidic % | 51.3 | 53.1 |
| | | Main % | 40.0 | 36.0 |
| | | Basic % | 8.8 | 10.9 |
| VI step yield [%] | | | 94 | 94 |

The two runs were performed after a PA step at pilot scale with a loading factor at 11 g/L for run 1 and 22 g/L for run 2. The targeted pH was pH 11.2 and the incubation time was performed beyond 90 minutes in order to mimic a worst case scenario. Some input operating ranges were obtained with basification ratio between 77.9 and 83.4 mL/L and neutralization ratio between 4.1 and 5.6 mL/L. In comparison, during non-representative small scale runs, ratios were within these ranges, with 81.5 mL/L for basification and 4.7 mL/L for neutralization. In addition, output operating ranges showed a pH revolving at about 6.0, a conductivity ranging from 4.0 and 4.4 mS/cm and a PA eluate concentration between 1.7 and 3.3 g/L, directly related to the loading factor. Finally, the step yield at 94% is usual for a low/high pH inactivation step.

Regarding the product quality results, HPLC-SE showed similar results between the two runs with 94.3% of monomers and comparable to small scale data where 94.8% for 1 hour of incubation and 94.6% for 2 hours have been observed. In addition, the CGE non-reduced results with a BEAT % at 89.9% for run 1 and 87.6% for run 2 were closed to small scale data which showed a BEAT % at about 88%. The slight difference observed on BEAT % was directly linked to BEAT" % variation. In fact, BEAT" % was 2.8% for run 1 and 4.1% for run 2. The method variability ≤10% and analytical peak integrations could explain these variations. The profile overlay presented in FIG. 22, does not show any significant fragmentation.

Finally, a difference of 4% in main peak of charge variants appeared with 40% for run 1 and 36% for run 2. This variation is directly related to the 2% increase of acidic species between run 1 and run 2 and same for basic species, leading to a non-relevant 4% decrease because within method variability. For comparison, a profile overlay is presented in FIG. 23. Closed values were observed at small scale with main peak at about 42%.

In conclusion, high pH scale up showed good product quality results, comparable to small scale data. Other assays as cell based functional assays and binding affinity assays were done to collect additional data.

Binding Affinity Assays

The relative affinities to CD3ε 1-26-Fc and EGFR are respectively listed in Table 59 and Table 60.

TABLE 59

Relative affinities of BEAT ®3 to CDε3 1-26-Fc target.
hsCD3ε relative KD (nM)

| Sample | Relative KD R1 | Relative KD R2 | Nb replicates | Average rel KD | Std dev rel KD | % CV rel KD |
|---|---|---|---|---|---|---|
| Reference #1 t0 | 0.972 | 0.955 | 4 | 1.00 | 0.04 | 4.4 |
| Reference #2 t0 | 1.028 | 1.045 | | | | |
| High pH t0 | 0.951 | 0.975 | 2 | 0.96 | 0.02 | 1.8 |
| High pH t2 h | 0.996 | 0.989 | 2 | 0.99 | 0.01 | 0.5 |
| High pH t4 h | 1.035 | 1.017 | 2 | 1.03 | 0.01 | 1.2 |
| High pH t24 h | 1.030 | 1.100 | 2 | 1.07 | 0.05 | 4.7 |

TABLE 60

Relative affinities of BEAT ®3 to EGFR target.
hsEGFR relative KD (pM)

| Sample | Relative KD R1 | Relative KD R2 | Nb replicates | Average rel KD | Std dev rel KD | % CV rel KD |
|---|---|---|---|---|---|---|
| Reference #1 t0 | 0.949 | 1.046 | 4 | 1.00 | 0.06 | 5.6 |
| Reference #2 t0 | 1.051 | 0.954 | | | | |
| High pH t0 | 0.988 | 0.967 | 2 | 0.98 | 0.01 | 1.5 |
| High pH t2 h | 1.025 | 1.020 | 2 | 1.02 | 0.01 | 0.4 |
| High pH t4 h | 1.106 | 1.073 | 2 | 1.09 | 0.02 | 2.1 |
| High pH t24 h | 1.166 | 1.133 | 2 | 1.15 | 0.02 | 2.1 |

No difference in affinity to CD3ε 1-26-Fc target was observed between samples treated at high pH. The relative dissociation constant average was 1.0 for reference and respectively 1.07 after 24 hours of high pH incubation.

Regarding EGFR target, only a slight increase appeared after more than 2 hours of incubation. The average of relative dissociation constants was 1.02 after 2 hours, 1.09 after 4 hours and 1.15 after 24 hours.

In conclusion, no difference in affinity of BEAT®3 to EGFR and CD3ε 1-26-Fc was observed for high pH until 2 hours of incubation covering the process time which is usually ≥60-≤90 minutes.

Cell Based Functional Assays

Figure 24:
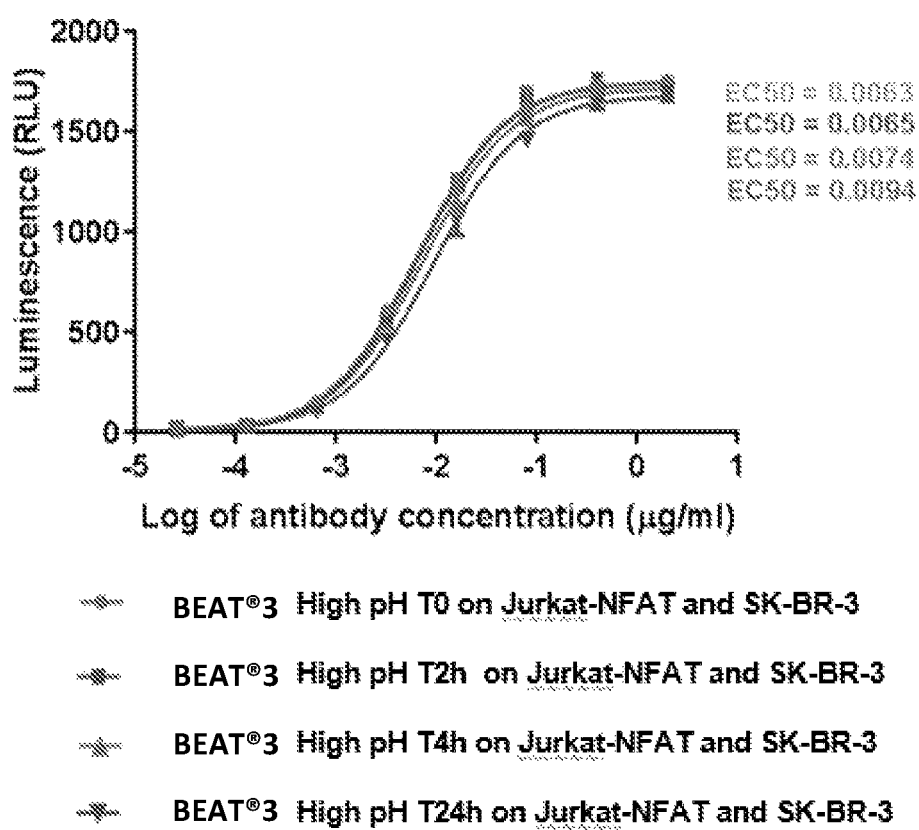

Cell based functional assay results are presented in FIG. 24. The half maximal effective concentrations (EC50) were determined based on the dose-response curves. The comparison of the different dose-response curves showed slight variations between high pH conditions. In fact, a small shift to the right is observed on the x axis when the incubation time increase. This shift reveals a decrease of product potency which is directly related to EC50 values increase (e.g. EC50=0.0063 at t0 and 0.0094 at t24 h).

The EC50 values obtained allowed to determine the relative potency of each sample taking as reference the sample with a high pH incubation time equal to zero. The results are presented in Table 61.

TABLE 61

Relative potencies according to high pH treatment duration.

| | Relative potency (%) |
|---|---|
| Reference BEAT ®3 High pH t0 | — |
| BEAT ®3 High pH t2 h | 97% |
| BEAT ®3 High pH t4 h | 85% |
| BEAT ®3 High pH t24 h | 67% |

The results showed a relative potency at 97% after 2 hours of incubation, 85% after 4 hours and 67% after 24 hours. With a method variability ≤25%, the relative potency was found to be stable until 2 hours of incubation and afterwards the decrease observed seems to show an alteration of BEAT®3 activity. In fact, for example, after 24 hours of incubation, the concentration of BEAT®3 should be higher than the concentration of reference sample (i.e. incubation time equal to zero) to obtain the same activity level. This decrease of relative potency percentage could be related to a potential oxidation of molecule involving a decrease in the activation of the responder cells and consequently a decrease of luminescence response. This hypothesis seemed in correlation with ICE results described previously, where an increase of acidic species was observed overtime. In fact, an oxidation could involve a loss of electrons negatively charged and consequently indirectly involve an increase of acidic species positively charged.

In conclusion, a decrease in BEAT®3 activity seems to be found when high pH incubation time increase. Nevertheless, BEAT®3 activity was not altered until 2 hours of incubation, covering the process time which is usually ≥60-≤90 minutes. The high pH treatment was once again validated as suitable.

Residual DNA and HCP Assays

The residual DNA assays performed on pilot scale high pH samples are presented in Table 62.

TABLE 62

Residual DNA assays results

| Testing material | Viral inactivation | VI incubation time | 0.2 μm filtrated after VI step | Concentration (pg DNA/ mg protein) | Removal % |
|---|---|---|---|---|---|
| PA eluate | — | — | — | 182 | — |
| VI neutralized | High pH | 90 min | No | 159 | 13 |
| VI neutralized | High pH | 90 min | Yes | 30 | 84 |

All PA eluates were filtrated at 0.2 μm before VI step.

The residual DNA concentrations were expressed in pictogram of DNA per milligram of protein allowing to compare all the samples between them whatever the protein concentration of each sample. After treatment at high pH, DNA concentration was 159 pg/mg (against 182 pg/mg in the load=PA eluate) and 30 pg/mg after filtration. Precipitations were observed during high pH incubation, probably due to impurity precipitations including DNA and host cell proteins (HCP). Consequently, high pH step removes DNA by precipitating and the precipitates are then removed by 0.2 μm filtration. The global removal step percentage was at about 84%.

The impact of high pH step on HCP contaminant level was assessed and results are presented in Table 63.

TABLE 63

HCP assay results with Octet and ELISA method.

| Testing material | Viral Inactivation | VI incubation time | 0.2 μm filtrated after VI | HCP (Octet) Concentration [ng HCP / mg protein] | Removal % | HCP (ELISA) Concentration [ng HCP / mg protein] | Removal % |
|---|---|---|---|---|---|---|---|
| PA eluate | — | — | — | 1425 | — | 2803 | — |
| VI neutralized | High pH | 90 min | No | 1154 | 19 | 1348 | 52 |
| VI neutralized | High pH | 90 min | Yes | 185 | 87 | 726 | 74 |

All PA eluates were filtrated at 0.2 μm before VI step.

The residual HCP concentrations were expressed in nanogram of HCP per milligram of protein in order to compare all the samples between them whatever the protein concentration of each sample. First sample has a concentration of residual HCP at 1425 ng/mg as per Octet instrument and 2803 ng/mg as per ELISA method. These results were not expected because the assay with the use of Octet was described by the supplier as more sensitive compared to a classical ELISA assays. These two non-treated samples were independently used as reference for each method.

Regarding the Octet results, after high pH treatment, HCP concentration was 1154 ng/mg against 1425 ng/mg on PA eluate without treatment. After filtration, concentration was 185 ng/mg. As observed for residual DNA assays, high pH treatment showed a potential to remove HCP probably precipitating during high pH incubation and removed by 0.2 μm filtration. For ELISA assay, a better sensitivity was showed (i.e. higher concentration measured), nevertheless the HCP removal percentages were comparable between both methods with about 80% removal for both VI.

In conclusion, high pH treatment showed an interesting potential to remove DNA and HCP impurities. The 0.2 μm filtration performed at the end of the step was essential with the aim of physically remove HCP and DNA precipitated during high pH incubation.

VRV NRT Study

High pH treatment was tested for its ability to efficiently inactivate viruses. A non-regulatory trial was performed at Bioreliance and the viral clearance results are summarized in the Table 64

TABLE 64

Summary of viral clearance of MLV after high pH treatment.

| Sample | High pH treatment | CL (95%) | Neutralized load (Titre/ml) | t0-1 min (Titre/ml) | t10 min (Titre/ml) | t30 min (Titre/ml) | t60 min (Titre/ml) | $\log_{10}$ Reduction Factor |
|---|---|---|---|---|---|---|---|---|
| PA Eluate | pH 10.8 (+/−0.05) | Lower | 6.58 | 4.83 | 1.93 | 1.30 | 1.13 | 5.65 ± 0.34 |
| | | Mean | 6.89 | 5.15 | 2.23 | 1.83 | 1.24 | |
| | | Upper | 7.21 | 5.46 | 2.53 | 2.36 | 1.36 | |

The viral clearance performed on Xenotropic Murine leukaemia virus (MLV) showed a 5.65 $\log_{10}$ reduction factor after 60 minutes of high pH treatment at pH 10.8 (+/−0.05). Therefore, high pH treatment appeared to be very effective in terms of viral clearance.

Figure 25:
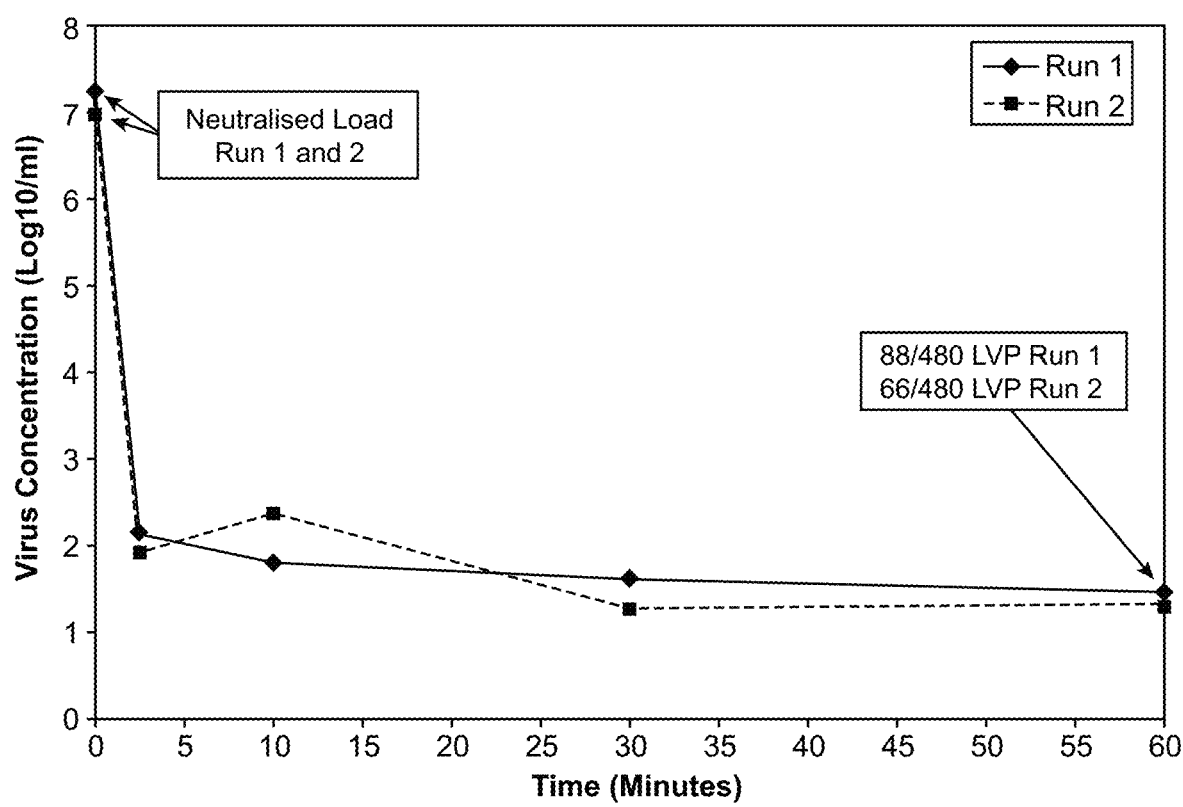

Also when testing virus clearance using the incubation of BEAT®3 at high pH as viral inactivation step of BEAT®3 purification process, the clearance results to be effective as shown by the high pH treatment kinetics in FIG. 25.

Virus titers and calculated log reduction factors are summarized in Table 66 below:

TABLE 65 / TABLE 66

High pH treatment viral log reduction

| Sample | Run | Neutralized load hold [log$_{10}$/mL] | Neutralized load [log$_{10}$/mL] | Neutralized load at different incubation time [log$_{10}$/mL] | | | | log$_{10}$ reduction factor |
|---|---|---|---|---|---|---|---|---|
| | | | | 0-5 min | 10 min | 30 min | 60 min | |
| Neutralized load [log$_{10}$/mL] | 1 | 6.72 | 7.24 | 2.15 | 1.81 | 1.62 | 1.47 | 5.77 |
| | 2 | 7.07 | 6.98 | 1.92 | 2.38 | 1.28 | 1.33 | 5.65 |

Both duplicate runs showed similar kinetic of inactivation with a significant and rapid decrease over time (e.g. 2.15 log$_{10}$, 1.81 log$_{10}$, 1.62 log$_{10}$ and 1.47 log$_{10}$ after 5, 10, 30 and 60 min of incubation) and a huge drop was systematically observed after 5 minutes of incubation. MLV reduction factors of 5.77 log$_{10}$ and 5.65 log$_{10}$ (i.e. run 1 and run 2 respectively) obtained for high pH treatment allowed to conclude that VI was effective for MLV virus's inactivation (i.e. all LRF>4.00 log$_{10}$).

In summary, different VI strategies were considered in order to select the most appropriate treatment for the antibody BEAT® 3. The selection criteria for the VI condition were firstly the stability of the molecule after the treatment, secondly the efficiency of the method to inactivate the viruses with an acceptable log reduction and finally the easiness to implement the manufacture process into the GMP area.

The low pH incubation on the PA eluate showed an important product degradation with an increase of high molecular weight species. This strategy was considered as not suitable for this project.

The solvent/detergent (S/D) treatment on bulk harvest and high pH on PA eluate were both found to be suitable showing similar results in terms of product quality regarding only the physicochemical properties. In addition, and considered as a new treatment, high pH VI was successfully validated as suitable with other assays based on product activity or viral clearance.

In conclusion, and considering all the parameters discussed in this report, the high pH treatment was selected as the most suitable VI strategy for BEAT®3 project and was implemented in process between PA and CEX step. The S/D treatment was considered as a backup option.

Also when testing virus removal upon incubation of BEAT®3 at high pH as viral inactivation step of BEAT®3 purification process, the removal results to be effective as shown by the high pH treatment kinetics in FIG. 25.

Virus titers and calculated log reduction factors are summarized in Table 66.

Both duplicate runs showed similar kinetic of inactivation with a significant and rapid decrease over time (e.g. 2.15 log$_{10}$, 1.81 log$_{10}$, 1.62 log$_{10}$ and 1.47 log$_{10}$ after 5, 10, 30 and 60 min of incubation) and a huge drop was systematically observed after 5 minutes of incubation. MLV reduction factors of 5.77 log$_{10}$ and 5.65 log$_{10}$ (i.e. run 1 and run 2 respectively) obtained for high pH treatment allowed to conclude that VI was effective for MLV virus's inactivation (i.e. all LRF>4.00 log$_{10}$).

EXAMPLE 8: HIGH pH IS A VALID ALTERNATIVE TO LOW pH TREATMENT ALSO IN THE PURIFICATION PROCESS OF NON LOW pH-LIABLE ANTIBODIES

To test the possibility of using high pH as alternative at the low pH incubation in the purification process of a non pH-liable antibody, the effects of high pH incubation in the stability and activity of a humanized IgG1 (here referred as Ab1) have been investigated.

Materials, Methods and Equipment

The starting material used in this study was representative PA eluate.

All chemicals were pharmacopoeia grade (US or EP). In-process 0.2 μm filtration steps were typically performed for all buffers and process intermediates. In addition, magnetic stirrer, pH and conductivity meter were used.

The time points tested were 1 hour, 2 hours and 4 hours at RT and beyond this point, the product was put at 5±3° C. up to 24 hours of incubation. About 100 mL of PA eluate was basified under agitation using a magnetic stirrer to pH 11.2 in a Nalgene bottle using NaOH 0.5 M. This pH was selected as a worst case scenario for product quality, in order to validate the target pH 11.0 of the process. The product at high pH was incubated except for time point t0 which was immediately neutralized as described below. At each time point, about 10 mL of high pH product was transferred into a 50 mL TPP tube and neutralized by decreasing the pH up to pH 5.2 using HCl 3.7% (neutralization step) in order to stop the VI reaction, before being frozen.

The product quality was analysed by HPLC-SE, iCE and CGE for all time points. PA eluate no neutralized and without any VI treatment was also analysed and used as reference.

TABLE 67

High pH testing conditions

| | Time points | | | | |
|---|---|---|---|---|---|
| Incubation time (h) | 0 | 1 | 2 | 4 | 24 |
| +5 ± 3° C. | NA | NA | NA | NA | X |
| Room Temperature | X | X | X | X | NA |

Some samples from testing described above, were selected to be tested by surface plasmon resonance (Table 37). The aim was to verify if the high pH treatment had an impact on the binding affinities of Ab1 molecule to its targets OX40R and FcgR3a and thus, indirectly, on its activity. In addition, cell based functional assay were also perform to directly verify the impact of high pH on Ab1 molecule activity.

TABLE 68

Samples tested for binding affinity and cell based functional assays

| | Time points | | |
|---|---|---|---|
| Incubation time (h) | 0 | 1 | 2 |
| +5 ± 3° C. | X | NA | NA |
| Room Temperature | | X | X |

Results and Conclusion

Figure 26:
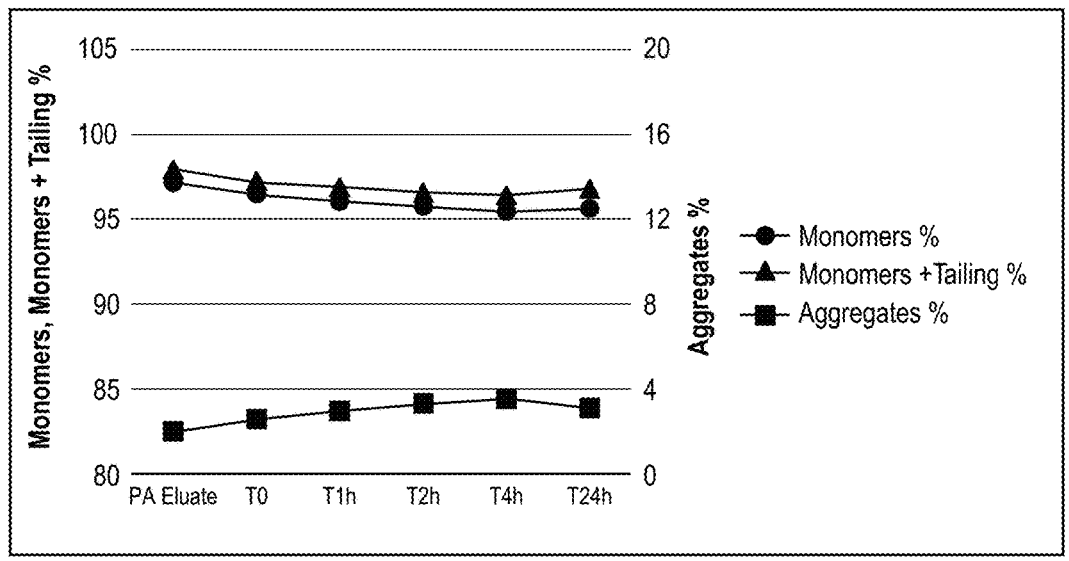
Figure 26:
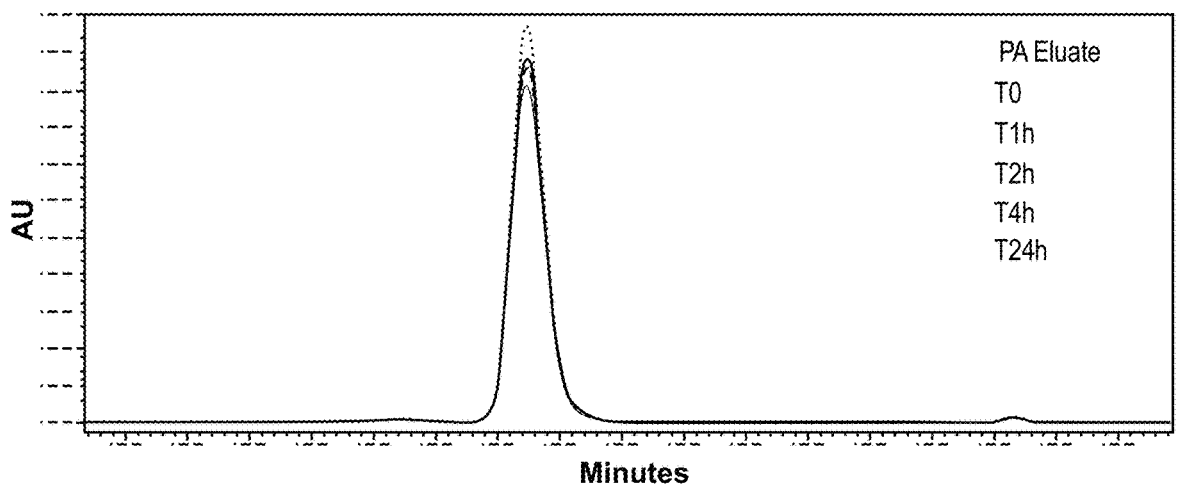
Figure 26:
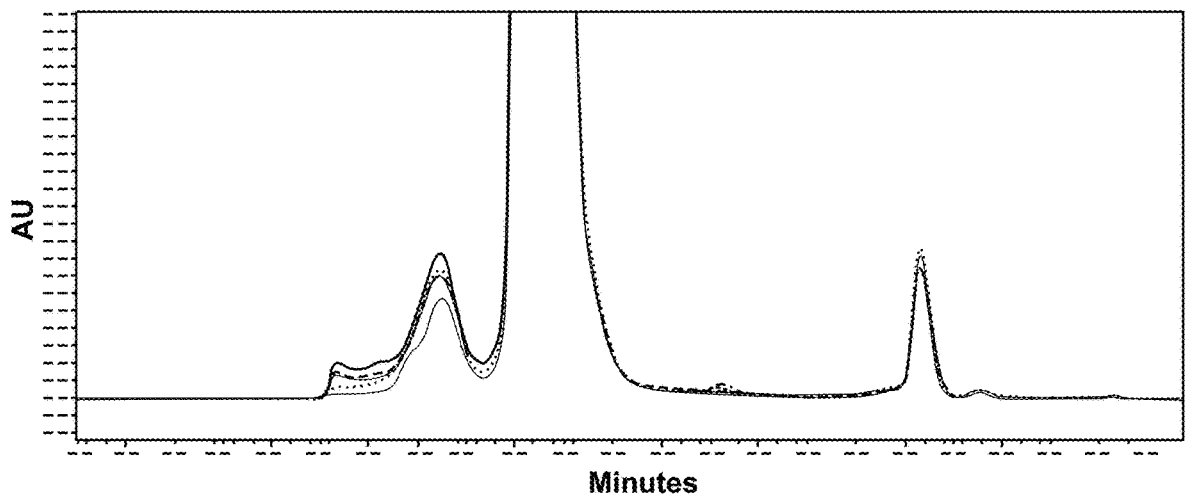

The hold time impact of high pH incubation of Ab1 has been analysed by SE-HPLC, the results are shown in FIG. 26, and in Table 69.

TABLE 69

HPLC-SE results

| | | Intermediate | PA Eluate | VI Neutralized | | | | |
|---|---|---|---|---|---|---|---|---|
| | | Time point | PA Eluate | t0 | t1 h | t2 h | t4 h | t24 h |
| HPLC-SE | Aggregates % | | 2.0 | 2.6 | 3.0 | 3.2 | 3.5 | 3.0 |
| | Monomers + Tailing % | | 97.9 | 97.3 | 96.9 | 96.7 | 96.4 | 96.8 |
| | Monomers % | | 97.1 | 96.5 | 96.0 | 95.7 | 95.5 | 95.6 |

The study shows that the percentage of monomers is comparable between conditions, additionally, no aggregation appears with high pH treatment up to 24 hours. The observed variations are included within method variability and are not statistically significant. Therefore, according to these results Ab1 is stable up to 24 hours covering with a safety margin the process time which is usually ≥60-≤90 minutes.

Figure 27:
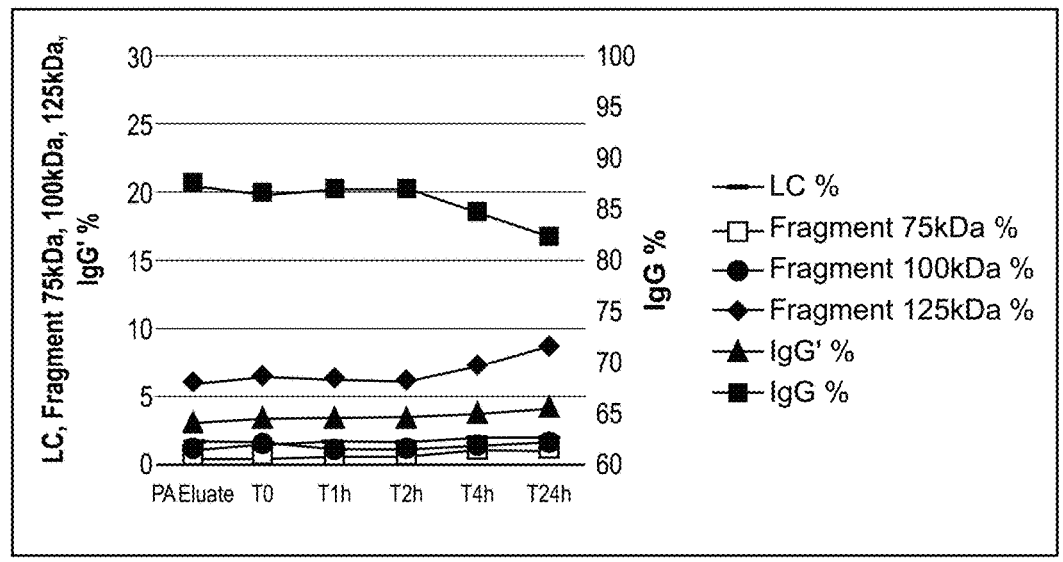
Figure 27:
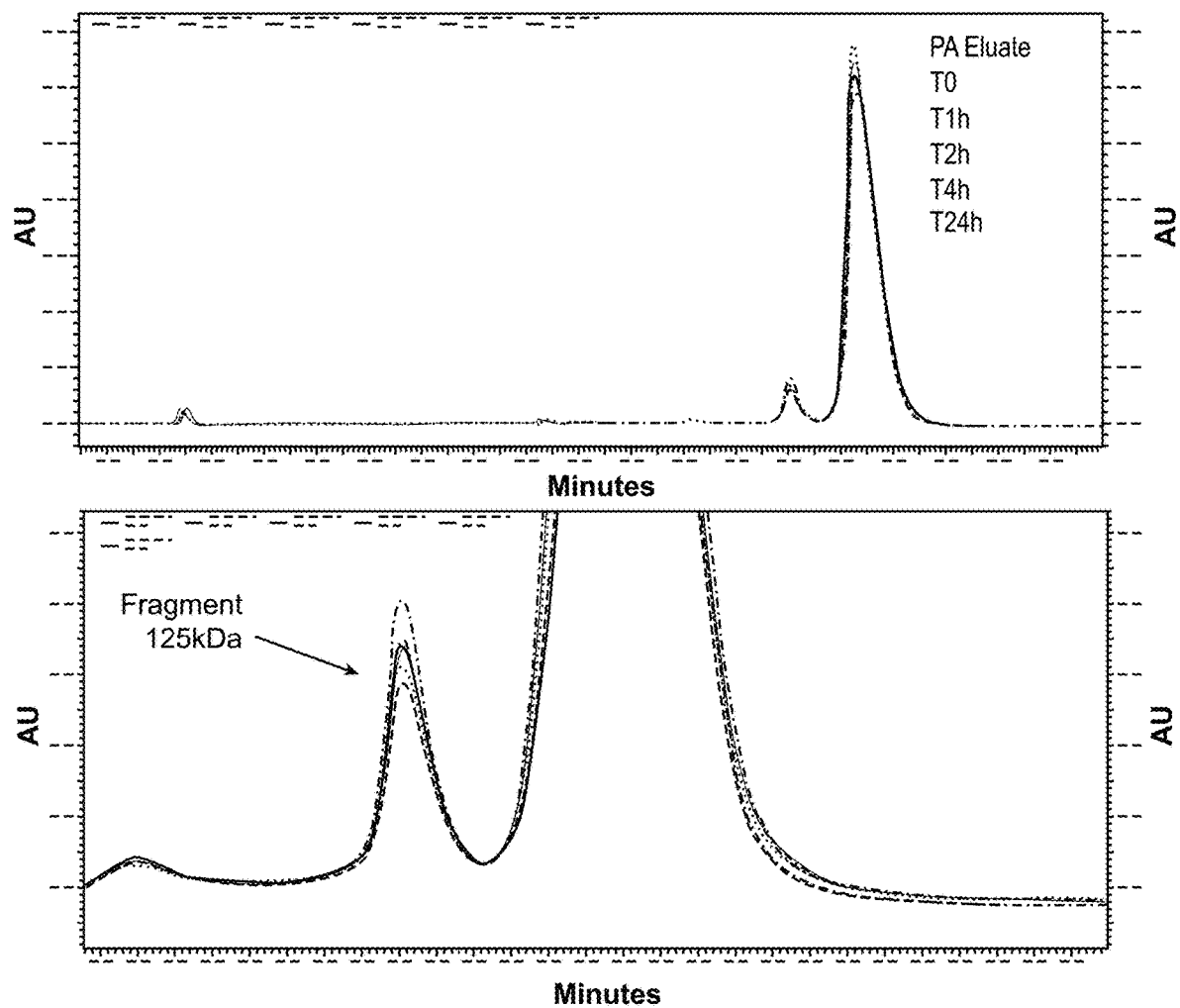
Figure 28:
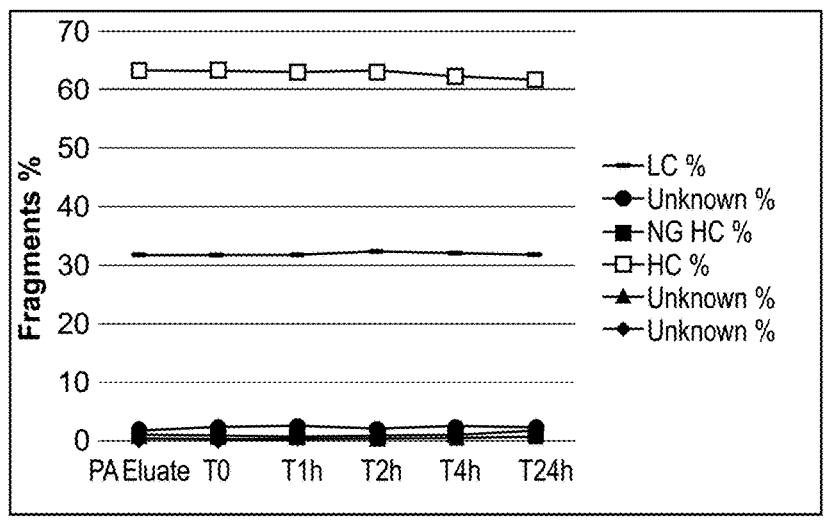
Figure 28:
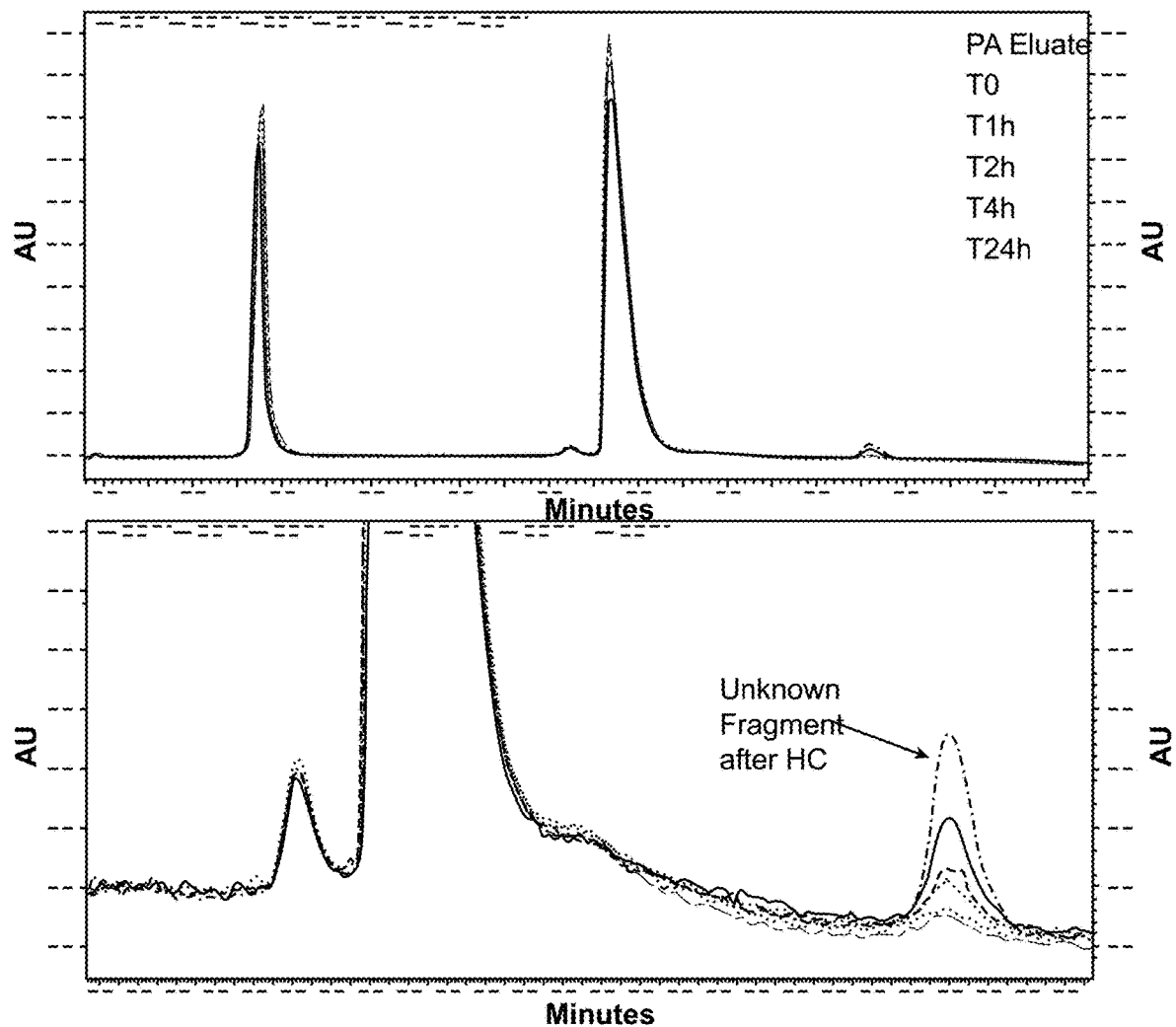

To further investigate the purity and identity of the sample upon high pH treatment, the hold time impact has been analysed by non-reduced CGE, Table 70 and FIG. 27. Also these experiments show that the intermediate percentages are comparable to reference sample (PA Eluate) and no significant fragmentation occurs until 2 hours. A slight increase of 125 kDa fragment percentage appears after 2 hours, and is correlated with IgG percentage decrease.

Taken together these results show that Ab1 is stable up to 2 hours covering with a safety margin the process time which is usually ≥60-≤90 minutes.

TABLE 70 non-reduced CGE results

| | Intermediate | PA Eluate | VI Neutralized | | | | |
|---|---|---|---|---|---|---|---|
| | Time point | PA Eluate | t0 | t1 h | t2 h | t4 h | t24 h |
| CGE-non-reduced | LC % | 1.7 | 1.5 | 1.7 | 1.7 | 1.9 | 2.0 |
| | Fragment 75 kDa % | 0.5 | 0.5 | 0.6 | 0.7 | 1.0 | 1.0 |
| | Fragment 100 kDa % | 1.2 | 1.5 | 1.1 | 1.2 | 1.4 | 1.7 |
| | Fragment 125 kDa % | 6.0 | 6.5 | 6.2 | 6.1 | 7.2 | 8.7 |
| | IgG' % | 3.1 | 3.4 | 3.5 | 3.5 | 3.8 | 4.2 |
| | IgG % | 87.5 | 86.4 | 86.9 | 86.9 | 84.7 | 82.3 |

Reduced CGE (in FIG. 28 and Table 71) also indicates that there is not significant fragment increase until 2 hours, while after 2 hours a slight increase of an "unknown fragment" percentages occurs and is correlated with HC % decrease.

These results confirm that Ab1 is stable up to 2 hours covering with a safety margin the process time which is usually ≥60-≤90 minutes.

TABLE 71 reduced CGE results

| | Intermediate | PA Eluate | VI Neutralized | | | | |
|---|---|---|---|---|---|---|---|
| | Time point | PA Eluate | t0 | t1 h | t2 h | t4 h | t24 h |
| CGE reduced | LC % | 31.7 | 31.6 | 31.7 | 32.3 | 32.0 | 31.7 |
| | Unknown % | 2.0 | 2.4 | 2.5 | 2.0 | 2.4 | 2.2 |
| | NG HC % | 1.0 | 0.9 | 0.8 | 0.8 | 0.9 | 0.9 |
| | HC % | 63.2 | 63.2 | 62.9 | 63.0 | 62.2 | 61.7 |
| | Unknown % | 0.8 | 0.7 | 0.6 | 0.4 | 0.5 | 0.7 |
| | Unknown % | 0.2 | 0.1 | 0.4 | 0.5 | 1.1 | 1.8 |

Figure 29:
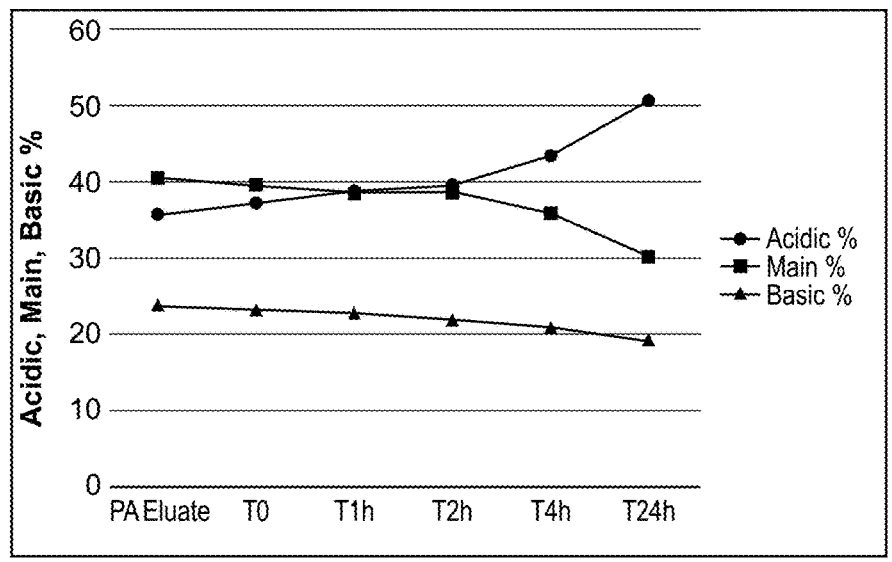
Figure 29:
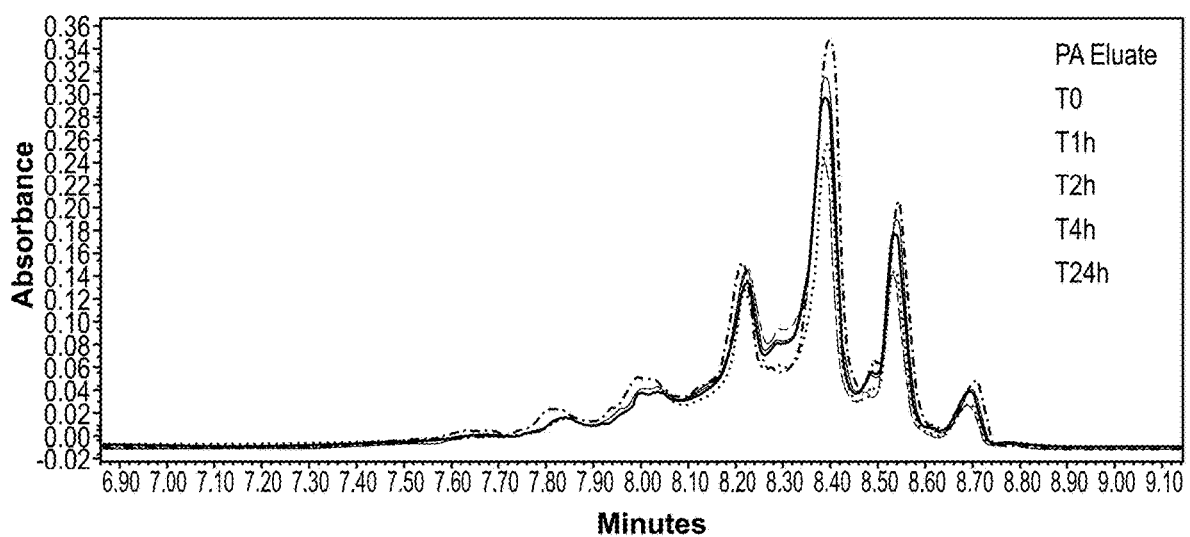
Figure 30:
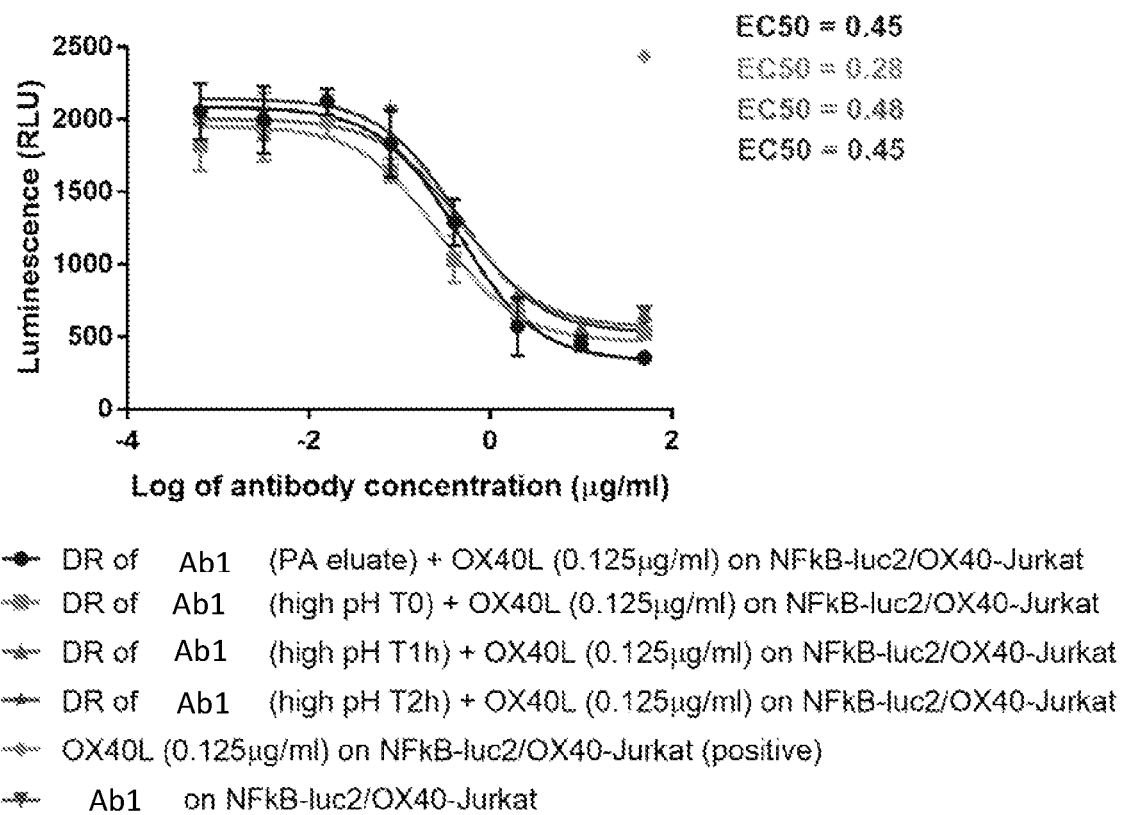

Hold time impact at high pH was additionally analysed by iCE to evaluate charge variants. The results, in Table 72 and FIG. 29, show an increase of acidic species over the time, nevertheless, the method variability is 10%, the differences observed until 2 hours are within method variability and could be considered as acceptable and statistically not significant. In other words, the acidic percentage increase observed is an expected trend and the 2 hours safety margin are covering the process time (and above) which is usually ≥60-≤90 minutes.

TABLE 72 iCE results

| | Intermediate Time point | PA Eluate PA Eluate | VI Neutralized | | | | |
|---|---|---|---|---|---|---|---|
| | | | t0 | t1 h | t2 h | t4 h | t24 h |
| ICE | Acidic % | 35.7 | 37.2 | 38.8 | 39.6 | 43.4 | 50.7 |
| | Main % | 40.5 | 39.6 | 38.5 | 38.6 | 35.8 | 30.2 |
| | Basic % | 23.8 | 23.2 | 22.7 | 21.8 | 20.8 | 19.1 |

A cell based functional assay was performed to evaluate the hold time impact at high pH on the molecule activity. According to the results, in FIG. 30 and Table 73, no tendency is observed overtime in the relative potency values. High pH treatment at t1 h and t2 h give highly similar potency compared to PA Eluate used as reference. Considering that the method variability is ≤25%, high pH treatment does not significantly altered Ab1 activity until 2 hours of incubation, covering the process time which is usually ≥60-≤90 minutes.

TABLE 73

Relative potency according to high pH treatment duration
Relative potency

| PA Eluate (reference) | 100% |
|---|---|
| t0 | 163% |
| t1 h | 94% |
| t2 h | 101% |

To evaluate the impact of high pH incubation on the activity of Ab1, a binding affinity assay (at Biacore) has been performed (Table 74).

TABLE 74

Relative affinities of Ab1 to its target

| Sample | Affinity measurement | Mean KD (nM) | StdDev (nM) | % CV | Relative KD (% PA eluate) |
|---|---|---|---|---|---|
| PA eluate | human OX40 | 198 | 51 | 25.8 | 100 |
| t0 | human OX40 | 229 | 8 | 3.3 | 116 |
| t1 | human OX40 | 207 | 4 | 1.9 | 105 |
| t2 | human OX40 | 224 | 3 | 1.4 | 113 |
| PA eluate | human FcγR3a | 689 | 13 | 1.9 | 100 |
| t0 | human FcγR3a | 760 | 27 | 3.6 | 110 |
| t1 | human FcγR3a | 744 | 9 | 1.2 | 108 |
| t2 | human FcγR3a | 638 | 27 | 4.2 | 93 |

No difference of functional significance in binding activity to human OX40 is observed between the protein A eluate and all samples incubated at high pH. Small differences might be due to slightly different concentrations injected.

No difference of functional significance in binding activity to human FcγR3a is observed between the protein A eluate and all samples incubated at high pH. Small differences might be due to slightly different concentrations injected.

Taken together these results show that high pH treatment of PA eluate is a valid alternative to low pH treatment also in the purification process of non low pH-liable antibodies.

The invention claimed is:

1. A method of production of a bulk drug substance comprising a therapeutic antibody, wherein the method comprises the steps of:
    (a) subjecting a harvested antibody material to Protein A chromatography;
    (b) incubating the resulting Protein A eluate at a high pH;
    (c) neutralizing the resulting viral inactivated solution to pH 5.5, followed by 0.2 um filtration;
    (d) subjecting the neutralized viral inactivated Protein A eluate to cation exchange chromatography, followed by 0.2 um filtration;
    (e) concentrating the cation exchange chromatography eluate by ultrafiltration and continuous diafiltration, followed by 0.2 um filtration;
    (f) purifying the product by anion exchange chromatography in flow through mode, using membrane adsorption, followed by 0.2 um filtration;
    (g) removing virus by nanofiltration;
    (h) concentrating the product by ultrafiltration and continuous diafiltration into pre-formulation buffer, followed by 0.2 um filtration;
    (i) adding excipients to achieve about 6 mg/mL of the product in the final formulation buffer, by mixing about 5 mM L-Histidine, about 150 mM L-Arginine Monohydrochloride, about 15% Sucrose, and about 0.06% Polysorbate 80, at pH of about 6.0, followed by 0.2 um filtration; and
    (j) filling the product into sterile bags, followed by freezing and storage at −80±20° C.

2. The method of claim 1, wherein the Protein A eluate is titrated to the target high pH with NaOH.

3. The method of claim 2, wherein the Protein A eluate is titrated with NaOH 0.5M to pH 11, for an incubation time of about 60 min at temperature between about 18° C. to about 25° C.

4. The method of claim 1, wherein the harvested antibody material is produced in non-human mammalian cells.

5. The method of claim 1, wherein the harvested antibody material comprises a monoclonal antibody.

6. The method of claim 5, wherein the monoclonal antibody is a recombinant antibody.

7. The method of claim 6, wherein the recombinant antibody is multispecific.

8. The method of claim 1, wherein the high pH is at between about 9 and about 12.5.

9. The method of claim 8, wherein the high pH is at least 10.5.

10. The method of claim 8, wherein the high pH is about 11.

11. The method of claim 1, wherein the Protein A eluate is titrated to a target high pH with a buffer selected from the group consisting of: Tris, Histidine L-Arginine phosphate and NaOH.

12. The method of claim 1 further comprising testing a portion of the virus-inactivated antibody solution with a viral inactivation assay.

* * * * *